US008557872B2

(12) United States Patent
Shin et al.

(10) Patent No.: US 8,557,872 B2
(45) Date of Patent: Oct. 15, 2013

(54) COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

(75) Inventors: Song Seok Shin, Yongin-si (KR); Jin Kwan Kim, Suwon-si (KR); Sun-Young Kim, Seoul (KR); Ki-Wha Lee, Seoul (KR); Byoung Young Woo, Yongin-si (KR); Joo-Hyun Moh, Seoul (KR); Yeon Su Jeong, Yongin-si (KR); Kyung Min Lim, Hwaseong-si (KR); Jin Kyu Choi, Suwon-si (KR); Hyun-Ju Koh, Gunpo-si (KR); Young-Ho Park, Seoul (KR)

(73) Assignee: Amorepacific Corporation (KR)

( * ) Notice: Subject to any disclaimer, the term of this patent is extended or adjusted under 35 U.S.C. 154(b) by 362 days.

(21) Appl. No.: 12/865,082

(22) PCT Filed: Jan. 28, 2009

(86) PCT No.: PCT/KR2009/000407
§ 371 (c)(1),
(2), (4) Date: Sep. 14, 2010

(87) PCT Pub. No.: WO2009/096701
PCT Pub. Date: Aug. 6, 2009

(65) Prior Publication Data
US 2011/0015230 A1 Jan. 20, 2011

(30) Foreign Application Priority Data
Jan. 28, 2008 (EP) .................................... 08001555

(51) Int. Cl.
A01N 37/18 (2006.01)
A01N 41/06 (2006.01)
A61K 31/165 (2006.01)
A61K 31/18 (2006.01)
C07C 233/00 (2006.01)
C07C 235/00 (2006.01)
C07C 237/00 (2006.01)
C07C 303/00 (2006.01)
C07C 307/00 (2006.01)
C07C 309/00 (2006.01)
C07C 311/00 (2006.01)

(52) U.S. Cl.
USPC .............. 514/617; 514/605; 564/99; 564/161

(58) Field of Classification Search
USPC .............................. 514/617, 605; 564/161, 99
See application file for complete search history.

(56) References Cited

U.S. PATENT DOCUMENTS

| 7,763,657 B2* | 7/2010 | Kim et al. ..................... 514/595 |
| 7,960,584 B2* | 6/2011 | Suh et al. ......................... 564/56 |
| 2007/0149513 A1 | 6/2007 | Chen et al. |
| 2007/0149517 A1 | 6/2007 | Koga et al. |

FOREIGN PATENT DOCUMENTS

| WO | WO 02/16318 A1 | 2/2002 |
| WO | WO 02/16319 A1 | 2/2002 |
| WO | WO 02/061317 A2 | 8/2002 |
| WO | WO 02/090326 A1 | 11/2002 |
| WO | WO 03/029199 A1 | 4/2003 |
| WO | WO 03/049702 A2 | 6/2003 |
| WO | WO 03/070247 A1 | 8/2003 |
| WO | WO 03/099284 A1 | 12/2003 |
| WO | WO 2004/007495 A1 | 1/2004 |
| WO | WO 2004/014871 A1 | 2/2004 |
| WO | WO 2004/024154 A1 | 3/2004 |
| WO | WO 2004/024710 A1 | 3/2004 |
| WO | WO 2004/029031 A2 | 4/2004 |
| WO | WO 2004/035549 A1 | 4/2004 |
| WO | WO 2004/072068 A1 | 8/2004 |
| WO | WO 2004/072069 A1 | 8/2004 |
| WO | WO 2004/089877 A1 | 10/2004 |
| WO | WO 2004/089881 A1 | 10/2004 |
| WO | WO 2004/111009 A1 | 12/2004 |
| WO | WO 2005/003084 A1 | 1/2005 |
| WO | WO 2005/044786 A1 | 5/2005 |
| WO | WO 2005/044802 A2 | 5/2005 |
| WO | WO 2005/047279 A1 | 5/2005 |
| WO | WO 2005/047280 A1 | 5/2005 |
| WO | WO 2005/049601 A1 | 6/2005 |
| WO | WO 2005/049613 A1 | 6/2005 |
| WO | WO 2005/051390 A1 | 6/2005 |
| WO | WO 2005/073193 A1 | 8/2005 |
| WO | WO 2006/051378 A1 | 5/2006 |

(Continued)

OTHER PUBLICATIONS

Morgan et al., "Vanilloid receptor 1 expression in human tooth pulp in relation to caries and pain," *J. Orofac. Pain* (2005) 19: 248-260.
Dinis et al., "The distribution of sensory fibers immunoreactive for the TRPV1 (Capsaicin) receptor in the human prostate," *European Urology* (2005) 48: 162-167.
Akerman et al., "Anandamide acts as a vasodilator of dural blood vessels in vivo by activating TRPV1 receptors," *British Journal of Pharmacology* (2004) 142: 1354-1360.

(Continued)

*Primary Examiner* — Kendra D Carter
(74) *Attorney, Agent, or Firm* — Merchant & Gould P.C.

(57) ABSTRACT

This present disclosure relates to novel compounds, isomer thereof or pharmaceutically acceptable salts thereof as vanilloid receptor (Vanilloid Receptor 1; VR1; TRPV1) antagonist; and a pharmaceutical composition containing the same. The present disclosure provides a pharmaceutical composition for preventing or treating a disease such as pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, heart disease and so on.

4 Claims, No Drawings

(56) References Cited

FOREIGN PATENT DOCUMENTS

| | | |
|---|---|---|
| WO | WO 2006/095263 A1 | 9/2006 |
| WO | WO 2006/097817 A1 | 9/2006 |
| WO | WO 2006/098554 A1 | 9/2006 |
| WO | WO 2006/100520 A1 | 9/2006 |
| WO | WO 2006/101318 A1 | 9/2006 |
| WO | WO 2006/101321 A1 | 9/2006 |
| WO | WO 2006/102645 A1 | 9/2006 |
| WO | WO 2006/103503 A1 | 10/2006 |
| WO | WO 2006/111346 A1 | 10/2006 |
| WO | WO 2006/113769 A1 | 10/2006 |
| WO | WO 2006/116563 A1 | 11/2006 |
| WO | WO 2006/120481 A2 | 11/2006 |
| WO | WO 2006/122250 A2 | 11/2006 |
| WO | WO 2006/122799 A1 | 11/2006 |
| WO | WO 2006/129164 A1 | 12/2006 |
| WO | WO 2007/042906 A1 | 4/2007 |
| WO | WO 2007/045462 A2 | 4/2007 |
| WO | WO 2007/050732 A1 | 5/2007 |
| WO | WO 2007/054474 A1 | 5/2007 |
| WO | WO 2007/054480 A1 | 5/2007 |
| WO | WO 2007/063925 A1 | 6/2007 |
| WO | WO 2007/065662 A2 | 6/2007 |
| WO | WO 2007/065663 A1 | 6/2007 |
| WO | WO 2007/065888 A1 | 6/2007 |
| WO | WO 2007/067619 A2 | 6/2007 |
| WO | WO 2007/067710 A1 | 6/2007 |
| WO | WO 2007/067711 A2 | 6/2007 |
| WO | WO 2007/067756 A2 | 6/2007 |
| WO | WO 2007/067757 A2 | 6/2007 |
| WO | WO 2007/069773 A1 | 6/2007 |

OTHER PUBLICATIONS

Ghilardi et al., "Selective blockade of the capsaicin receptor TRPV1 attenuates bone cancer pain," *The Journal of Neuroscience* (2005) 25 (12): 3126-3131.

Gopinath et al., "Increased capsaicin receptor TRVP1 in skin nerve fibres and related vanilloid receptors TRPV3 and TRPV4 in keratinocytes in human breast pain," *BMC Women's Health* (2005) 5: 1-9.

Park et al., "Nitric oxide mediates capsaicin-induced cytotoxicity in cultured dorsal root ganglion neurons," *Arch Pharm Res.* (1999) 22 (4): 432-434.

Kim et al., "Transient receptor potential vanilloid sybtype 1 mediates cell death of mesencephalic dopaminergic neurons in vivo and in vitro," *The Journal of Neuroscience* (2005) 25 (3): 662-671.

Kamei et al., "Role of vanilloid VR1 receptor in thermal allodynia and hyperalgesia in diabetic mice," *European Journal of Pharmacology* (2001) 422: 83-86.

Geppetti et al., "The transient receptor potential vanilloid 1: Role in airway inflammation and disease," *European Journal of Pharmacology* (2006) 533: 207-214.

McLeod et al., "TRPV1 antagonists attenuate antigen-provoked cough in ovalbumin sensitized guinea pigs," *Cough* (2006) 2(10): 1-17.

Balaban et al., "Type 1 vanilloid receptor expression by mammalian inner ear ganglion cells," *Hearing Research* (2003) 175: 165-170.

Scotland et al., "Vanilloid receptor TRPV1, sensory C-Fibers, and vascular autoregulation: A novel mechanism involved in myogenic constriction," *Circulation Research* (2004) 95: 1027-1034.

Pan et al., "Sensing tissue ischernia," *Circulation* (2004) 110: 1826-1831.

Akabori et al., "Transient receptor potential vanilloid 1 antagonist, capsazepine, improves survival in a rat hemorrhagic shock model," *Ann. Surg.* (2007) 245: 964-970.

Bodo et al., "Involvement of vanilloid receptor-1 (VR1/TRPV1) signaling in human hair growth control," *American Journal of Pathology* (2005) 166 (4): 985-998.

Biro et al., "Hair cycle control by vanilloid receptor-1 (TRVP1): Evidence from TRPV1 knockout mice," *J. Invest. Dermatol.* (2006): 1-4.

Seki et al., "Expression and localization of TRPV1 in human nasal mucosa," *Rhinology* (2006) 44: 128-134.

Hutter et al., "Transient receptor potential vanilloid (TRPV-1) promotes neurogenic inflammation in the pancrease via activation of the neurokinin-1 receptor (NK-1R)," *Pancreas* (2005) 30 (3): 260-265.

Dinis et al., "Anandamide-evoked activation of vanilloid receptor 1 contributes to the development of bladder hyperreflexia and nociceptive transmission to spinal dorsal horn neurons in cystitis," *The Journal of Neuroscience* (2004) 24 (50): 11263-11253.

Sculptoreanu et al., "Protein kinase C contributes to abnormal capsaicin responses in DRG neurons from cats with feline interstitial cystitis," *Neuroscience Letters* (2005) 381: 42-46.

Tympanidis et al., "Incrased vanilloid receptor VR1 innervation in vulvodynia," *European Journal of Pain* (2004).8: 129-133.

Kunishima et al, "Synthesis and characterization of 4-(4,6-dimethoxy-1,3,5-triazin-2-yl)-4-methylmorpholinium chloride," *Tetrahedron Letters* (1999) 40: 5327-5330.

Wood et al., "Capsaicin-induced ion fluxes in dorsal root ganglion cells in culture," *The Journal of Neuroscience*(1988) 8 (9): 3208-3220.

Caterina et al., "The capsicin receptor: a heat-activated ion channel in the pain pathway," *Nature* (1997) 389: 816-824.

Tominaga et al., "The cloned capsaicin receptor integrates multiple pain-producing stimuli," *Neuron* (1998) 21: 531-543.

Hwang et al., "Direct activation of capsaicin receptors by products of lipoxygenases: Endogenous capsaicin-like substances," *PNAS* (2000) 97 (11): 6155-6160.

Mezey et al., "Distribution of mRNA for vanilloid receptor subtype 1 (VR1), and VR1-like immunoreactivity, in the central nervous system of the rat and human," *PNAS* (2000) 97 (7): 3655-3660.

Stander et al., "Expression of vanilloid receptor subtype 1 in cutaneous sensory nerve fibers, mast cells, and epithelial cells of appendage structures," *Experimental Dermatology* (2004) 13: 129-139.

Cortright et al., "The tissue distribution and functional characterization of human VR1," *Biochemical and Biophysical Research Communications* (2001) 281: 1183-1189.

Caterina et al., "Impaired nociception and pain sensation in mice lacking the capsaicin receptor," *Science* (2000) 288: 306-313.

Davis et al., "Vanilloid receptor-1 is essential for inflammatory thermal hyperalgesia," *Letters to Nature* (2000) 405: 183-187.

Karai et al., "Deletion of vanilloid receptor 1-expressing primary afferent neurons for pain control," *The Journal of Clinical Investigation* (2004) 113 (9): 1344-1352.

Immke et al., "The TRPV1 receptor and nociception," *Seminars in Cell & Developmental Biology* (2006) 17: 582-591.

Ma et al., "Inflammatory mediators modulating the transient receptor potential vanilloid 1 receptor: therapeutic targets to treat inflammatory and neuropathic pain," *Expert Opinion* (2007) 11 (3): 307-320.

Walker et al., "The VR1 antagonist capsazepine reverses mechanical hyperalgesia in models of inflammatory and neuropathic pain," *The Journal of Phannacology and Experimental Therapeutics* (2003) 304 (1): 56-62.

Garcia-Martinez et al., "Attenuation of thermal nociception and hyperalgesia by VR1 blockers," *PNAS* (2002)99 (4): 2374-2379.

Holzer, P., "Capsaicin: Cellular targets, mechanisms of action, and selectivity for thin sensory neurons," *Pharmacolgical Reviews* (1991) 45 (2): 143-201.

Chan et al., "Sensory fibres expressing capsaicin receptor TRPV1 in patients with rectal hypersensitivity and faecal urgency," *The Lancet* (2003) 361: 385-391.

Yiangou et al., "Vanilloid receptor 1 immunoreactivity in inflamed human bowel," *The Lancet* (2001) 357: 1338-1339.

Holzer, P., "TRPV1 and the gut: from a tasty receptor for a painful vanilloid to a key player in hyperalgesia," *European Journal of Pharmacology* (2004) 500: 231-241.

Geppetti et al., "Activation and sensitization of the vanilloid receptor: role in gastrointestinal inflammation and function," *British Journal of Pharmacology* (2004) 141: 1313-1320.

Hwang et al., "Hot channels in airways: pharmacology of the vanilloid receptor," *Current Opinion in Pharmacology* (2002) 2: 235-242.

Spina et al., "Pharmacology of airway irritability," *Current Opinion in Pharmacology* (2002) 2: 264-272.

(56) References Cited

OTHER PUBLICATIONS

Veronesi et al., "Neurogenic inflammation and particulate matter (PM) air pollutants," *NeuroToxicology* (2001) 22: 795-810.

Birder et al., "Vanilloid receptor expression suggests a sensory role for urinary bladder epithelial cells," *PNAS* (2001) 98 (23): 13396-13401.

Birder et al., "Altered urinary bladder function in mice lacking the vanilloid receptor TRPV1," *Nature Neuroscience* (2002) 5 (9): 856-860.

Denda et al., "Immunoreactivity of VR1 on epidermal keratinocyte of human skin," *Biochemical and Biophysical Research Communications* (2001) 285: 1250-1252.

Inoue et al., "Functional vanilloid receptors in cultured normal human epidermal keratinocytes," *Biochemical and Biophysical Research Communications* (2002) 291: 124-129.

Southall et al., "Acivation of epidermal vanilloid receptor-1 induces release of proinflammatory mediators in human keratinocytes," *The Journal of Pharmacology and Experimental Therapeutics* (2003) 304 (1): 217-222.

Inoue et al., "Transient receptor potential channels in cardiovascular function and disease," *Circulation Research* (2006) 99: 119-131.

Razavi et al., "TRPV1 sensory neurons control β cell stress and islet inflammation in autoimmune diabetes," *Cell* (2006) 127: 1123-1135.

Gram et al., "Capsaicin-sensitive sensory fibers in the islets of Langerhans contribute to defective insulin secretion in Zucker diabetic rat, an animal model for some aspects of human type 2 diabetes," *European Journal of Neuroscience* (2007) 25: 213-223.

Marsch et al., "Reduced anxiety, conditioned fear, and hippocampal long-term potentiation in transient receptor potential vanilloid type 1 receptor-deficient mice," *The Journal of Neuroscience* (2007) 27 (4): 832-839.

Szallasi et al., "The vanilloid receptor TRPV1: 10 years from channel cloning to antagonist proof-of-concept," *Nature Reviews* (2007) 6: 357-372.

Appendino et al., "4 clinically useful vanilloid receptor TRPV1 antagonists: Just around the corner (or too early to tell)?" *Progress in Medicinal Chemistry* (2006) 44: 145-180.

Rami et al., "The therapeutic potential of TRPV1 (VR1) antagonists: clinical answers await," *Drug Discovery Today: Therapeutic Strategies* (2004): 97-104.

Correll et al., "Advances in the development of TRPV1 antagonists," *Expert Opinion* (2006) 16: 783-795.

Kyle et al., "TRPV1 antagonists: a survey of the patent literature," *Expert Opinion* (2006) 977-996.

Nagy et al., "The role of the vanilloid (capsaicin) receptor (TRPV1) in physiology and pathology " *European Journal of Pharmacology* (2004) 500: 351-369.

Petersen et al., "Capsaicin evoked pain and allodynia in post-herpetic neuralgia," *Pain* (2000) 88: 125-133.

\* cited by examiner

COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

TECHNICAL FIELD

The present disclosure relates to novel compounds, isomer thereof or pharmaceutically acceptable salts thereof as TRPV1 antagonist; and a pharmaceutical composition containing the same.

BACKGROUND ART

The vanilloid receptor-1 (VR1, or transient receptor potential vanilloid-1, TRPV1) is the receptor for capsaicin (8-methyl-N-vanillyl-6-nonenamide), a pungent ingredient in hot peppers. The molecular cloning of TRPV1 was reported in 1997 (Caterina et al., 1997, Nature, 389, pp 816-824), which belongs to the TRP channel family of non-selective cation channel. TRPV1 is activated or sensitized by stimuli such as capsaicin, resiniferatoxin, heat, acid, anandamide, lipid metabolites or the like; thus it plays a crucial role as a molecular integrator of noxious stimuli in mammals (Tominaga et al., 1998, Neuron, 21 pp 531-543; Hwang et al., 2000, PNAS, 97, pp 6155-6160). The TRPV1 is highly expressed in primary afferent sensory neurons, and also reportedly expressed in various organs and tissues such as bladder, kidney, lung, intestine, skin, central nervous system (CNS), and non-neuronal tissues (Mezey et al., 2000, PNAS, 97, pp 3655-3660; Stander et al., 2004, Exp. Dermatol. 13, pp 129-139; Cortright et al., 2001, BBRC, 281, pp 1183-1189), and besides TRPV1 protein is upregulated in painful disease conditions. Activation of the TRPV1 by endogenous/exogenous stimuli leads to not only transmission of noxious stimuli, but also liberation of neuropeptides such as substance P, CGRP (Calcitonin Gene-Related Peptide) in the neurons, thereby causing neurogenic inflammation. TRPV1 knock-out mice show normal responses in a wide range of behavioural tests including noxious mechanical and acute thermal stimuli, but exhibit little thermal hypersensitivity in inflammation states. (Caterina et al., 2000, Science, 288, pp 306-313; Davis et al., 2000, Nature, 405, pp 183-187; Karai et al., 2004, J. Clin. Invest., 113, pp 1344-1352).

As mentioned above, the TRPV1 knock-out mice exhibit reduced responses to thermal or noxious stimuli, which has been supported by the effects of TRPV1 antagonists in various animal models of pain (Immke et al., 2006, Semin. Cell. Dev. Biol., 17(5), pp 582-91; Ma et al., 2007, Expert Opin. Ther. Targets, 11(3), pp 307-20). The well-known TRPV1 antagonist, capsazepine, decreases hyperalgesia caused by physical stimuli in several models of inflammatory and neuropathic pain (Walker et al., 2003, JPET, 304, pp 56-62; Garcia-Martinez et al., 2002, PNAS, 99, 2374-2379). In addition, treatment of the primary culture of afferent sensory neurons with the TRPV1 agonist, capsaicin etc., results in damage to nerve functions and furthermore death of nerve cells. The TRPV1 antagonist exerts defense actions against such damage to nerve functions and nerve cell death (Holzer P., 1991, Pharmacological Reviews, 43, pp 143-201; Mezey et al., 2000, PNAS, 97, 3655-3660). The TRPV1 is expressed on sensory neurons distributed in all regions of the gastrointestinal tract and is highly expressed in inflammatory disorders such as irritable bowel syndrome and inflammatory bowel disease (Chan et al., 2003, Lancet, 361, pp 385-391; Yiangou et al., 2001, Lancet, 357, pp 1338-1339). In addition, activation of the TRPV1 stimulates sensory nerves, which in turn causes release of neuropeptides which are known to play a critical role in pathogenesis of gastrointestinal disorders such as gastro-esophageal reflux disease (GERD) and stomach duodenal ulcer (Holzer P., 2004, Eur. J. Pharmacol. 500, pp 231-241; Geppetti et al., 2004, Br. J. Pharmacol., 141, pp 1313-1320).

The TRPV1-expressing afferent nerves are abundantly distributed in airway mucosa, and bronchial hypersensitivity is very similar mechanism to hyperalgesia. Protons and lipoxygenase products, known as endogenous ligands for the TRPV1, are well known as crucial factors responsible for development of asthma and chronic obstructive pulmonary diseases (Hwang et al., 2002, Curr. Opin. Pharmacol. pp 235-242; Spina et al., 2002, Curr. Opin. Pharmacol. pp 264-272). Moreover, it has been reported that air-polluting substances which are a kind of asthma-causing substances, i.e., particulate matter specifically acts on the TRPV1 and such action is inhibited by capsazepine (Veronesi et al., 2001, NeuroToxicology, 22, pp 795-810). Urinary bladder hypersensitiveness and urinary incontinence are caused by various central/peripheral nerve disorders or injury, and TRPV1 expressed in afferent nerves and urothelial cells play an important role in bladder inflammation. (Birder et al., 2001, PNAS, 98, pp 13396-13401). Further, TRPV1 knock-out mice are anatomically normal but have higher frequency of low-amplitude, non-voiding bladder contractions and reduced reflex voiding during bladder filling as compared to wild type mice, which is thus indicating that the TRPV1 affects functions of the bladder (Birder et al., 2002, Nat. Neuroscience, 5, pp 856-860). The TRPV1 is distributed in human epidermal keratinocytes as well as in primary afferent sensory nerves (Denda et al., 2001, Biochem. Biophys. Res. Commun, 285, pp 1250-1252; Inoue et al., 2002, Biochem. Biophys. Res. Commun., 291, pp 124-129), and it is then involved in transmission of various noxious stimuli and pains such as skin irritation and pruritus, thereby having close correlation with etiology of dermatological diseases and disorders, such as skin inflammation, due to neurogenic/non-neurogenic factors. This is supported by the report that the TRPV1 antagonist, capsazepine inhibits inflammatory mediators in human skin cells (Southall et al., 2003, J. Pharmacol. Exp. Ther., 304, pp 217-222). Over recent years, evidence has been accumulation on other roles of TRPV1. TRPV1 might be involved in the blood flow/pressure regulation via sensory vasoactive neuropeptide release and in the regulation of plasma glucose levels or in the pathogenesis of type 1 diabetes (Inoue et al., Cir. Res., 2006, 99, pp 119-31; Razavi et al., 2006, Cell, 127, pp 1123-35; Gram et al., 2007, Eur. J. Neurosci., 25, pp 213-23). Further, it is reported that TRPV1 knock-out mice show less anxiety-related behavior than their wild type littermates with no differences in locomotion (Marsch et al., 2007, J. Neurosci., 27(4), pp 832-9).

Based on the above-mentioned information, development of various TRPV1 antagonists is under way, and some patents and patent applications relating to TRPV1 antagonists under development were published. (Szallasi et al., 2007, Nat. Rev. Drug Discov., 6, pp 357-72; Appendino et al., 2006, Progress in Medicinal Chemistry, 44, pp 145-180; Rami et al., 2004, Drug Discovery Today: Therapeutic Strategies, 1, pp 97-104; Correll et al., 2006, Expert Opin. Ther. Patents, 16, pp 783-795; Kyle et al., 2006, Expert Opin. Ther. Patents, 16, pp 977-996)

Compounds of the present disclosure, are useful for prophylaxis and treatment of diseases associated with the activity of TRPV1 (Nagy et al., 2004, Eur. J. Pharmacol. 500, 351-369) including but not limited to, pain such as acute pain, chronic pain, neuropathic pain, post-operative pain, rheumatic arthritic pain, osteoarthritic pain, postherpetic neuralgia, neuralgia, headache, dental pain, pelvic pain, migraine, bone cancer pain, mastalgia and visceral pain (Petersen et al., 2000, Pain 88, pp 125-133; Walker et al., 2003, J. Pharmacol. Exp. Ther., 304, pp 56-62; Morgan et al., 2005, J. Orofac. Pain, 19, pp 248-60; Dinis et al., 2005, Eur. Urol., 48, pp 162-7; Akerman et al., 2004, Br. J. Pharmcol., 142, pp 1354-1360; Ghilardi et al., 2005, J. Neurosci., 25, 3126-31; Gopinath et al., 2005, BMC Womens Health, 5, 2-9); nerve-related diseases such as neuropathies, HIV-related neuropathy, nerve injury, neurodegeneration, and stroke (Park et al., 1999, Arch. Pharm. Res. 22, pp 432-434; Kim et al., 2005, J. Neurosci. 25(3), pp 662-671); diabetic neuropathy (Kamei et al., 2001, Eur. J. Pharmacol. 422, pp 83-86); fecal urgency; irritable bowel syndrome (Chan et al., 2003, Lancet, 361, pp 385-391); inflammatory bowel disease (Yiangou et al., 2001, Lancet 357, pp 1338-1339); gastrointestinal disorders such as gastro-esophageal reflux disease (GERD), stomach duodenal ulcer and Crohn's disease (Holzer P, 2004, Eur. J. Pharm., 500, pp 231-241; Geppetti et al., 2004, Br. J. Pharmacol., 141, pp 1313-1320); respiratory diseases such as asthma, chronic obstructive pulmonary disease, cough (Hwang et al., 2002, Curr. Opin. Pharmacol. pp 235-242; Spina et al., 2002, Curr. Opin. Pharmacol. pp 264-272; Geppetti et al., 2006, Eur. J. Pharmacol., 533, pp 207-214; McLeod et al., 2006, Cough, 2, 10); urinary incontinence (Birder et al., 2002, Nat. Neuroscience 5, pp 856-860); urinary bladder hypersensitiveness (Birder et al., 2001, PNAS, 98, pp 13396-13401); neurotic/allergic/inflammatory skin diseases such as psoriasis, pruritus, prurigo and dermatitis (Southall et al., 2003, J. Pharmacol. Exp. Ther., 304, pp 217-222); irritation of skin, eye or mucous membrane (Tominaga et al., 1998, Neuron 21 pp 531-543); hyperacusis; tinnitus; vestibular hypersensitiveness (Balaban et al., 2003, Hear Res. 175, pp 165-70); cardiac diseases such as myocardial ischemia (Scotland et al., 2004, Circ. Res. 95, pp 1027-1034; Pan et al., 2004, Circulation 110, pp 1826-1831); haemorrhagic shock (Akabori et al., 2007, Ann. Surg., 245(6), pp 964-70); hair growth-related disorders such as hirsutism, effluvium, alopecia (Bodo et al., 2005, Am. J. Patho. 166, pp 985-998; Biro et al., 2006, J. Invest. Dermatol. pp 1-4); rhinitis (Seki et al., 2006, Rhinology, 44, pp 128-34); pancreatitis (Hutter et al., 2005, Pancreas, 30, pp 260-5); cystitis (Dinis et al., 2004, J. Neurosci., 24, pp 11253-63; Sculptoreanu et al., 2005, Neurosci. Lett. 381, pp 42-6); vulvodynia (Tympanidis et al., 2004, Eur. J. Pain, 8, pp 12-33); psychiatric disorders such as anxiety or fear (Marsch et al., 2007, J. Neurosci., 27(4), pp 832-9).

Compounds that are related to VR1 activities are discussed e.g. in WO 02/61317, WO 02/090326, WO 02/16318, WO 02/16319, WO 03/053945, WO 03/099284, WO 03/049702, WO 03/049702, WO 03/029199, WO 03/70247, WO 04/07495, WO 04/72068, WO 04/035549, WO 04/014871, WO 04/024154, WO 04/024710, WO 04/029031, WO 04/089877, WO 04/089881, WO 04/072069, WO 04/111009, WO 05/03084, WO 05/073193, WO 05/051390, WO 05/049613, WO 05/049601, WO 05/047280, WO 05/047279, WO 05/044802, WO 05/044786, WO 06/097817, WO 06/098554, WO 06/100520, WO 06/101321, WO 06/102645, WO 06/103503, WO 06/111346, WO 06/101321, WO 06/101318, WO 06/1113769, WO 06/116563, WO 06/120481, WO 06/122250, WO 06/122799, WO 06/129164, WO 06/51378, WO 06/95263, WO 07/42906, WO 07/45462, WO 07/50732, WO 07/54474, WO 07/54480, WO 07/63925, WO 07/65663, WO 07/65888, WO 07/67619, WO 07/67710, WO 07/67711, WO 07/67756, WO 07/67757, WO07/63925, WO07/65662, WO07/65663, WO07/65888, WO07/69773, US20070149517, or US20070149513.

More specifically, WO 06/101321 and WO 06/101318 relate to VR1 modulators with a biphenyl partial structure. As a result of extensive and intensive studies, the present inventors have consequently synthesized novel compounds having VR1 antagonistic activity. Said new compounds have biphenylic structures, wherein one phenyl ring is substituted in para position to its attachment position to the rest of the molecule with a trifluoromethyl group or a fluoro, and has at least one additional substituent in ortho position (relative to said attachment position). Compared to the specific compounds disclosed in WO 06/101321 or WO 06/101318, which do not show this particular combination of features, the present compounds show remarkable improvement of their physicochemical characteristics, such as metabolic stability or pharmacokinetic profiles.

Therefore, it is an object of the present disclosure to provide novel compounds useful as a potent antagonist for a TRPV1, isomer thereof and pharmaceutically acceptable salts thereof; and a pharmaceutical composition comprising the same.

DETAILED DESCRIPTION OF THE DISCLOSURE

The present disclosure provides a novel compound of the following formula (Ia), an isomer, or a pharmaceutically acceptable salt thereof:

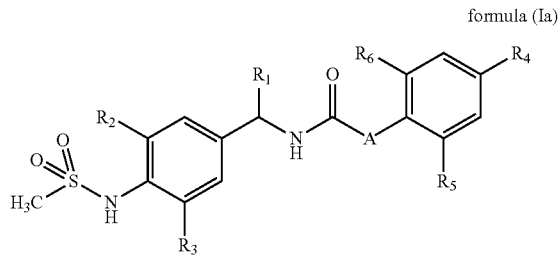

formula (Ia)

wherein,

A is —C═C— or —CH—CH—;

$R_1$ is hydrogen, or C1-C3 alkyl;

$R_2$ and $R_3$ are independently hydrogen, halogen, cyano, C1-C3 alkyl, C1-C3 alkoxy, halo(C1-C3)alkyl, (C2-C5) alkenyl, or (C2-C5)alkynyl;

$R_4$ is halo(C1-C3)alkyl or halogen;

$R_5$ is C2-C10 alkyl, C2-C10 alkoxy, C1-C5 alkoxy (C1-C5) alkoxy, C1-C5 alkoxy (C1-C5) alkylamino, C2-C10 alkylamino, di(C1-C5 alkyl)amino, C3-C6 cycloalkylamino, C3-C6 cycloalkoxy, or (C3-C6)cycloalkyl(C1-C3)alkyloxy; and $R_6$ is hydrogen, C1-C10 alkyl, C1-C10 alkoxy, or C1-C10 alkylamino The present disclosure also provides a novel compound of the following formula (I), an isomer, or a pharmaceutically acceptable salt thereof:

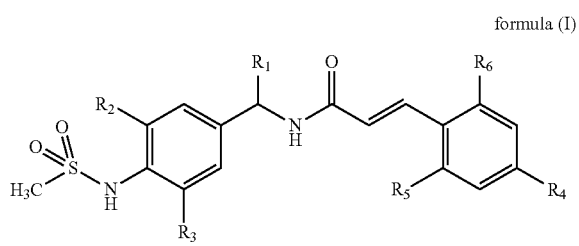

formula (I)

wherein, $R_1$ is hydrogen, methyl, or ethyl;

$R_2$ and $R_3$ are independently hydrogen, halogen, cyano, methyl, ethyl, methoxy, trifluoromethyl, vinyl, or acetylenyl;

$R_4$ is trifluoromethyl or fluoro;

$R_5$ is C2-C5 alkyl, C2-C5 alkoxy, C1-C2 alkoxy (C1-C3) alkoxy, C1-C2 alkoxy (C1-C3) alkylamino, C2-C5 alkylamino, di(C1-C3 alkyl)amino, C3-C6 cycloalkylamino, C3-C6 cycloalkoxy, or (C3-C6)cycloalkyl(C1-C3)alkyloxy; and $R_6$ is hydrogen, C1-C5 alkyl, C1-C5 alkoxy, or C1-C5 alkylamino Another aspect of the present disclosure is a compound according to the above formula (Ia) or (I), an isomer, or a pharmaceutically acceptable salt thereof; as described above wherein if $R_5$ is ethoxy, butoxy, pentoxy, (C3-C6)cycloalkoxy, or (C3-C6)cycloalkyl(C1-C3)alkyloxy, then $R_1$ is methyl.

In another embodiment in the compounds of formula (Ia) or (I) as disclosed further above, if $R_5$ is ethoxy, butoxy, or pentoxy, and $R_4$ is simultaneously fluoro, then $R_1$ is methyl.

In another embodiment in the compounds of formula (Ia) or (I) as disclosed further above, if $R_5$ is ethoxy, butoxy, or pentoxy, then $R_4$ is trifluoromethyl. In this specific embodiment, $R_1$ is preferably methyl.

Another aspect of the present disclosure is a compound according to the above formula (Ia) or (I), an isomer, or a pharmaceutically acceptable salt thereof; wherein, $R_1$ is hydrogen; $R_2$ is halogen; and $R_5$ is C2-C4 alkyl or C2-C4 alkylamino.

One aspect of the present disclosure is a compound according to the above formula (Ia) or (I), an isomer, or a pharmaceutically acceptable salt thereof; wherein, $R_1$ is hydrogen; $R_2$ is fluoro; $R_3$ is hydrogen, fluoro, cyano, methyl, vinyl, or acetylenyl; $R_4$ is trifluoromethyl; $R_5$ is C2-C4 alkyl or C2-C4 alkylamino; and $R_6$ is hydrogen.

Another aspect of the present disclosure is a compound according to the above formula (Ia) or (I), an isomer, or a pharmaceutically acceptable salt thereof; wherein, $R_1$ is hydrogen, methyl, ethyl, or preferably methyl.

One aspect of the present disclosure is a compound according to the above formula (Ia) or (I), an isomer, or a pharmaceutically acceptable salt thereof; wherein, $R_1$ is methyl; $R_2$ is halogen; and $R_5$ is C2-C4 alkyl, C2-C4 alkyloxy, or C2-C4 alkylamino.

Another aspect of the present disclosure is a compound according to the above formula (Ia) or (I), an isomer, or a pharmaceutically acceptable salt thereof;
wherein,
$R_1$ is methyl;
$R_2$ is fluoro;
$R_3$ is hydrogen, fluoro, vinyl, methyl, or acetylenyl;
$R_5$ is C2-C4 alkyl, C2-C4 alkyloxy, or C2-C4 alkylamino; and
$R_6$ is hydrogen or C1-C3 alkyl.

One aspect of the present disclosure is a compound according to the above formula (Ia) or (I), an isomer, or a pharmaceutically acceptable salt thereof; wherein, $R_2$ and $R_3$ are independently hydrogen, fluoro, cyano, methyl, ethyl, methoxy, trifluoromethyl, vinyl, acetylenyl, or preferably hydrogen, fluoro, cyano, methyl, vinyl, or acetylenyl.

One aspect of the present disclosure is a compound according to the above formula (Ia) or (I), an isomer, or a pharmaceutically acceptable salt thereof; wherein, $R_2$ and $R_3$ are both fluoro.

One aspect of the present disclosure is a compound according to the above formula (Ia) or (I), an isomer, or a pharmaceutically acceptable salt thereof; wherein, $R_4$ is fluoro, or preferably trifluoromethyl.

One aspect of the present disclosure is a compound according to the above formula (Ia) or (I), an isomer, or a pharmaceutically acceptable salt thereof; wherein, $R_5$ and $R_6$ are both C1-C3 alkyl; or preferably methyl, ethyl, or propyl; or more preferably propyl.

One aspect of the present disclosure is a compound according to the above formula (Ia) or (I), an isomer, or a pharmaceutically acceptable salt thereof; wherein, $R_6$ is hydrogen.

One aspect of the present disclosure is a compound according to the above formula (Ia) or (I), an isomer, or a pharmaceutically acceptable salt thereof; wherein, $R_5$ is ethyl, propyl, isopropyl, n-butyl, isobutyl, sec-butyl, ethoxy, propoxy, isopropoxy, butoxy, isobutoxy, sec-butoxy, ethylamino, propylamino, isopropylamino, n-butylamino, isobutylamino, sec-butylamino, or cyclohexylmethoxy, provided that if $R_5$ is ethoxy, butoxy, pentoxy, or cyclohexylmethoxy, then $R_1$ is methyl.

Another aspect of the present disclosure is a compound of the formula (Ia) or (I) as further described herein, an isomer, or a pharmaceutically acceptable salt thereof, wherein, if $R_1$ is methyl or ethyl, then the compound may be a pure enantiomer or may be a mixture of the (R) and (S)-enantiomer; and then, the C-atom to which $R_1$ is attached is preferably in the (R)-configuration.

Another aspect of the present disclosure are compounds of the formula (Ia) or (I) as further described herein, an isomer, or a pharmaceutically acceptable salt thereof wherein, $R_5$ is C2-C5 alkyl, (C2-C5)alkyloxy, C1-C4 alkylamino, or (C3-C6)cycloalkylalkoxyoxy, wherein preferably, $R_5$ is C2-C4 alkyl, (C2-C4)alkyloxy, or C2-C4 alkylamino; wherein particularly preferably, $R_5$ is C2-C4 alkyl, or C1-C3 alkylamino; wherein particularly preferably, $R_5$ is ethyl, n-propyl, isopropyl, n-butyl, isobutyl, sec-butyl, ethoxy, propoxy, isopropoxy, n-butoxy, isobutoxy, sec-butoxy, ethylamino, n-propylamino, isopropylamino, n-butylamino, isobutylamino, sec-butylamino, or cyclohexylmethoxy, wherein particularly preferably, $R_5$ is C2-C4 alkyl, propoxy, isopropoxy, or C2-C4 alkylamino; wherein even more preferably, $R_5$ is ethyl, n-propyl, isopropyl, n-butyl, isobutyl, sec-butyl, propoxy, isopropoxy, ethylamino, n-propylamino, isopropylamino, n-butylamino, isobutylamino, or sec-butylamino, wherein even more preferably, $R_5$ is n-propyl, n-butyl, isobutyl, isopropoxy, sec-butoxy, ethylamino, n-propylamino, isopropylamino, n-butylamino, wherein more preferably, $R_5$ is n-propyl, n-butyl, isobutyl, n-propoxy, ethylamino, propylamino, isopropylamino, n-butylamino, wherein even more preferably, $R_5$ is propyl, butyl, isobutyl, ethylamino, propylamino, or isopropylamino, wherein even more preferably, R₅ is propyl, butyl, ethylamino, propylamino, or isopropylamino Preferred examples of compounds according to the disclosure are selected from the group consisting of;

N-[1-(3,5-Difluoro-4-methanesulfonylamino-phenyl)-ethyl]-3-(2-propylamino-4-trifluoromethyl-phenyl)-acrylamide,
N-(3,5-Difluoro-4-methanesulfonylamino-benzyl)-3-(2-propylamino-4-trifluoromethyl-phenyl)-acrylamide,
(R)-3-(2-Butylamino-4-trifluoromethyl-phenyl)-N-[1-(3,5-difluoro-4-methanesulfonylamino-phenyl)-ethyl]-acrylamide,
(R)—N-[1-(3,5-Difluoro-4-methanesulfonylamino-phenyl)-ethyl]-3-(2-propoxy-4-trifluoromethyl-phenyl)-acrylamide,
(R)—N-[1-(3,5-Difluoro-4-methanesulfonylamino-phenyl)-ethyl]-3-(2,6-dipropyl-4-trifluoromethyl-phenyl)-acrylamide,
(R)—N-[1-(3,5-Difluoro-4-methanesulfonylamino-phenyl)-ethyl]-3-(2-ethoxy-4-trifluoromethyl-phenyl)-acrylamide,
(R)—N-[1-(3,5-Difluoro-4-methanesulfonylamino-phenyl)-ethyl]-3-(2-ethylamino-4-trifluoromethyl-phenyl)-acrylamide,
N-(3-Fluoro-4-methanesulfonylamino-5-methyl-benzyl)-3-(2-propylamino-4-trifluoromethyl-phenyl)-acrylamide,
N-(3-Fluoro-4-methanesulfonylamino-5-vinyl-benzyl)-3-(2-propylamino-4-trifluoromethyl-phenyl)-acrylamide,
N-(3-Cyano-5-fluoro-4-methanesulfonylamino-benzyl)-3-(2-propylamino-4-trifluoromethyl-phenyl)-acrylamide,
N-(3-Ethynyl-5-fluoro-4-methanesulfonylamino-benzyl)-3-(2-propoxy-4-trifluoromethyl-phenyl)-acrylamide,
(R)-3-(2,6-Dibutyl-4-trifluoromethyl-phenyl)-N-[1-(3,5-difluoro-4-methanesulfonylamino-phenyl)-ethyl]-acrylamide,
(R)-3-(2,6-Diethyl-4-trifluoromethyl-phenyl)-N-[1-(3,5-difluoro-4-methanesulfonylamino-phenyl)-ethyl]-acrylamide,
N-(3,5-Difluoro-4-methanesulfonylamino-benzyl)-3-(2-ethylamino-4-trifluoromethyl-phenyl)-acrylamide,
3-(2-Ethylamino-4-trifluoromethyl-phenyl)-N-(3-fluoro-4-methanesulfonylamino-5-methyl-benzyl)-acrylamide,
N-(3,5-Difluoro-4-methanesulfonylamino-benzyl)-3-(2-isopropoxy-4-trifluoromethyl-phenyl)-acrylamide,
(R)—N-[1-(3,5-Difluoro-4-methanesulfonylamino-phenyl)-ethyl]-3-(2-propyl-4-trifluoromethyl-phenyl)-acrylamide,
N-(3,5-Difluoro-4-methanesulfonylamino-benzyl)-3-(2-propyl-4-trifluoromethyl-phenyl)-acrylamide,
N-(3-Fluoro-4-methanesulfonylamino-5-methyl-benzyl)-3-(2-propyl-4-trifluoromethyl-phenyl)-acrylamide,
(R)-3-(2-Butyl-4-trifluoromethyl-phenyl)-N-[1-(3,5-difluoro-4-methanesulfonylamino-phenyl)-ethyl]-acrylamide,
(R)—N-[1-(3,5-Difluoro-4-methanesulfonylamino-phenyl)-propyl]-3-(2-propyl-4-trifluoromethyl-phenyl)-acrylamide,
(R)—N-[1-(3,5-Difluoro-4-methanesulfonylamino-phenyl)-ethyl]-3-(2-isopropoxy-4-trifluoromethyl-phenyl)-acrylamide,
(R)—N-[1-(3,5-Difluoro-4-methanesulfonylamino-phenyl)-ethyl]-3-(4-fluoro-2-propoxy-phenyl)-acrylamide,
(R)—N-[1-(3,5-Difluoro-4-methanesulfonylamino-phenyl)-ethyl]-3-(4-fluoro-2-propylamino-phenyl)-acrylamide,
(R)-3-(2-Butoxy-4-trifluoromethyl-phenyl)-N-[1-(3,5-difluoro-4-methanesulfonylamino-phenyl)-ethyl]-acrylamide,
(R)-3-(2-Butoxy-4-fluoro-phenyl)-N-[1-(3,5-difluoro-4-methanesulfonylamino-phenyl)-ethyl]-acrylamide,
N-(3-Ethynyl-5-fluoro-4-methanesulfonylamino-benzyl)-3-(2-propyl-4-trifluoromethyl-phenyl)-acrylamide,
(R)-3-(2-Butyl-4-trifluoromethyl-phenyl)-N-[1-(3-fluoro-4-methanesulfonylamino-phenyl)-ethyl]-acrylamide,
(R)-3-(2-sec-Butoxy-4-trifluoromethyl-phenyl)-N-[1-(3,5-difluoro-4-methanesulfonylamino-phenyl)-ethyl]-acrylamide,
(R)-3-(2-sec-Butoxy-4-fluoro-phenyl)-N-[1-(3,5-difluoro-4-methanesulfonylamino-phenyl)-ethyl]-acrylamide,
(R)—N-[1-(3,5-Difluoro-4-methanesulfonylamino-phenyl)-ethyl]-3-(2-ethylamino-4-fluoro-phenyl)-acrylamide,
N-(3,5-Difluoro-4-methanesulfonylamino-benzyl)-3-(2-ethylamino-4-fluoro-phenyl)-acrylamide,
(R)—N-(2-Fluoro-4-{1-[3-(2-propyl-4-trifluoromethyl-phenyl)-allylamino]-ethyl}-phenyl)-methanesulfonamide,
(R)-3-(2-Butylamino-4-fluoro-phenyl)-N-[1-(3,5-difluoro-4-methanesulfonylamino-phenyl)-ethyl]-acrylamide,
3-(2-Butylamino-4-fluoro-phenyl)-N-(3,5-difluoro-4-methanesulfonylamino-benzyl)-acrylamide,
(R)—N-[1-(3,5-Difluoro-4-methanesulfonylamino-phenyl)-ethyl]-3-(2-isobutyl-4-trifluoromethyl-phenyl)-acrylamide,
(R)-3-(2-Cyclohexylmethoxy-4-trifluoromethyl-phenyl)-N-[1-(3,5-difluoro-4-methanesulfonylamino-phenyl)-ethyl]-acrylamide,
(R)—N-[1-(3,5-Difluoro-4-methanesulfonylamino-phenyl)-ethyl]-3-(4-fluoro-2-propyl-phenyl)-acrylamide,
N-(3-Fluoro-4-methanesulfonylamino-5-vinyl-benzyl)-3-(2-isopropylamino-4-trifluoromethyl-phenyl)-acrylamide, and
(R)—N-[1-(3,5-Difluoro-4-methanesulfonylamino-phenyl)-ethyl]-3-(2-propylamino-4-trifluoromethyl-phenyl)-propionamide.

Particularly preferred examples of compounds according to the disclosure are selected from the group consisting of;

N-[1-(3,5-Difluoro-4-methanesulfonylamino-phenyl)-ethyl]-3-(2-propylamino-4-trifluoromethyl-phenyl)-acrylamide,
(R)-3-(2-Butylamino-4-trifluoromethyl-phenyl)-N-[1-(3,5-difluoro-4-methanesulfonylamino-phenyl)-ethyl]-acrylamide,
(R)—N-[1-(3,5-Difluoro-4-methanesulfonylamino-phenyl)-ethyl]-3-(2-propoxy-4-trifluoromethyl-phenyl)-acrylamide,
(R)—N-[1-(3,5-Difluoro-4-methanesulfonylamino-phenyl)-ethyl]-3-(2,6-dipropyl-4-trifluoromethyl-phenyl)-acrylamide,
(R)—N-[1-(3,5-Difluoro-4-methanesulfonylamino-phenyl)-ethyl]-3-(2-ethoxy-4-trifluoromethyl-phenyl)-acrylamide,
(R)—N-[1-(3,5-Difluoro-4-methanesulfonylamino-phenyl)-ethyl]-3-(2-ethylamino-4-trifluoromethyl-phenyl)-acrylamide,
N-(3-Fluoro-4-methanesulfonylamino-5-methyl-benzyl)-3-(2-propylamino-4-trifluoromethyl-phenyl)-acrylamide,
N-(3-Fluoro-4-methanesulfonylamino-5-vinyl-benzyl)-3-(2-propylamino-4-trifluoromethyl-phenyl)-acrylamide,
N-(3-Cyano-5-fluoro-4-methanesulfonylamino-benzyl)-3-(2-propylamino-4-trifluoromethyl-phenyl)-acrylamide,
(R)-3-(2,6-Diethyl-4-trifluoromethyl-phenyl)-N-[1-(3,5-difluoro-4-methanesulfonylamino-phenyl)-ethyl]-acrylamide,
N-(3,5-Difluoro-4-methanesulfonylamino-benzyl)-3-(2-ethylamino-4-trifluoromethyl-phenyl)-acrylamide,
N-(3,5-Difluoro-4-methanesulfonylamino-benzyl)-3-(2-isopropoxy-4-trifluoromethyl-phenyl)-acrylamide, (R)—N-[1-(3,5-Difluoro-4-methanesulfonylamino-phenyl)-ethyl]-3-(2-propyl-4-trifluoromethyl-phenyl)-acrylamide, (R)-3-(2-Butyl-4-trifluoromethyl-phenyl)-N-[1-(3,5-difluoro-4-methanesulfonylamino-phenyl)-ethyl]-acrylamide, (R)—N-[1-(3,5-Difluoro-4-methanesulfonylamino-phenyl)-ethyl]-3-(2-isopropoxy-4-trifluoromethyl-phenyl)-acrylamide, (R)-3-(2-Butoxy-4-trifluoromethyl-phenyl)-N-[1-(3,5-difluoro-4-methanesulfonylamino-phenyl)-ethyl]-acrylamide, (R)-3-(2-Butoxy-4-fluoro-phenyl)-N-[1-(3,5-difluoro-4-methanesulfonylamino-phenyl)-ethyl]-acrylamide, N-(3-Ethynyl-5-fluoro-4-methanesulfonylamino-benzyl)-3-(2-propyl-4-trifluoromethyl-phenyl)-acrylamide, (R)-3-(2-Butyl-4-trifluoromethyl-phenyl)-N-[1-(3-fluoro-4-methanesulfonylamino-phenyl)-ethyl]-acrylamide, (R)-3-(2-sec-Butoxy-4-trifluoromethyl-phenyl)-N-[1-(3,5-difluoro-4-methanesulfonylamino-phenyl)-ethyl]-acrylamide, (R)-3-(2-sec-Butoxy-4-fluoro-phenyl)-N-[1-(3,5-difluoro-4-methanesulfonylamino-phenyl)-ethyl]-acrylamide, (R)—N-[1-(3,5-Difluoro-4-methanesulfonylamino-phenyl)-ethyl]-3-(2-ethylamino-4-fluoro-phenyl)-acrylamide, (R)—N-(2-Fluoro-4-{1-[3-(2-propyl-4-trifluoromethyl-phenyl)-allylamino]-ethyl}-phenyl)-methanesulfonamide, (R)-3-(2-Butylamino-4-fluoro-phenyl)-N-[1-(3,5-difluoro-4-methanesulfonylamino-phenyl)-ethyl]-acrylamide, (R)—N-[1-(3,5-Difluoro-4-methanesulfonylamino-phenyl)-ethyl]-3-(2-isobutyl-4-trifluoromethyl-phenyl)-acrylamide, and N-(3-Fluoro-4-methanesulfonylamino-5-vinyl-benzyl)-3-(2-isopropylamino-4-trifluoromethyl-phenyl)-acrylamide.

The compounds of the formula (Ia) or (I) of the present disclosure can chemically be synthesized by the following reaction schemes. However, these are given only for illustration of the disclosure and not intended to limit to them.

[Scheme 1]

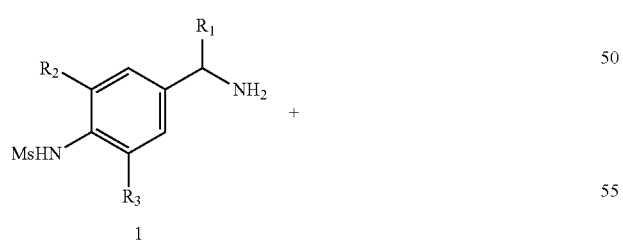

1

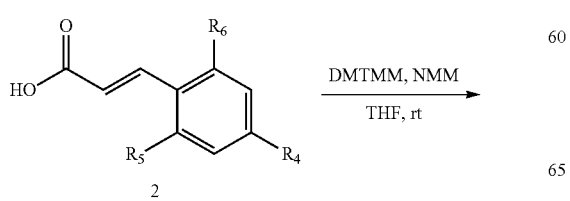

2

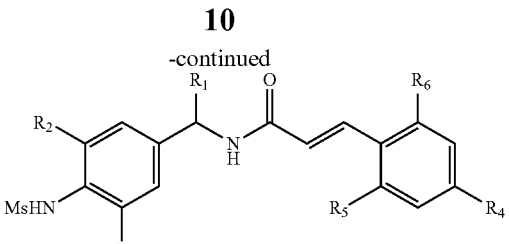

3

The Scheme 1 shows a proposed process for synthesizing acrylamide compound with various substituents. Substituted benzylamine (1) is reacted with phenylacrylic acid (2) to yield benzyl phenylacrylamide (3) using DMTMM {4-(4,6-dimethoxy-1,3,5-triazin-2-yl)-4-methylmorpholinium chloride} (Tetrahedron Lett., 1999, 40, 5327).

[Scheme 2]

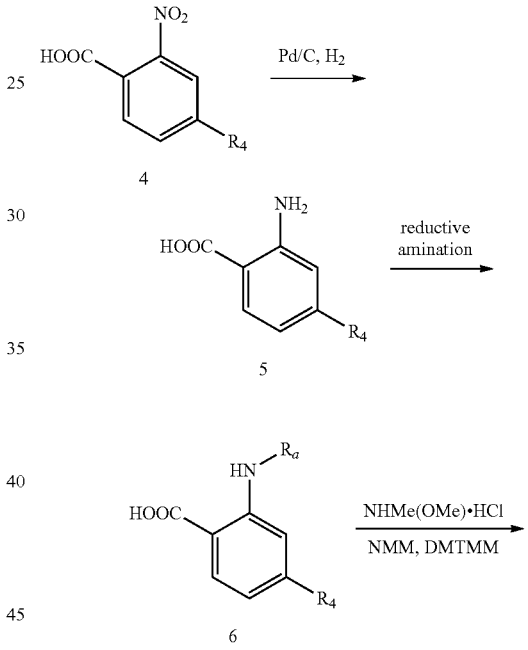

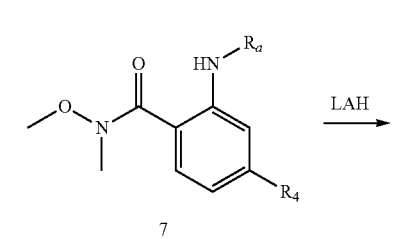

7

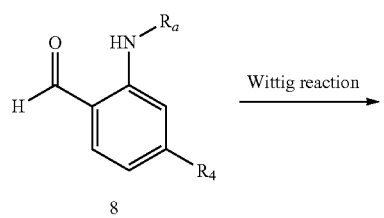

8

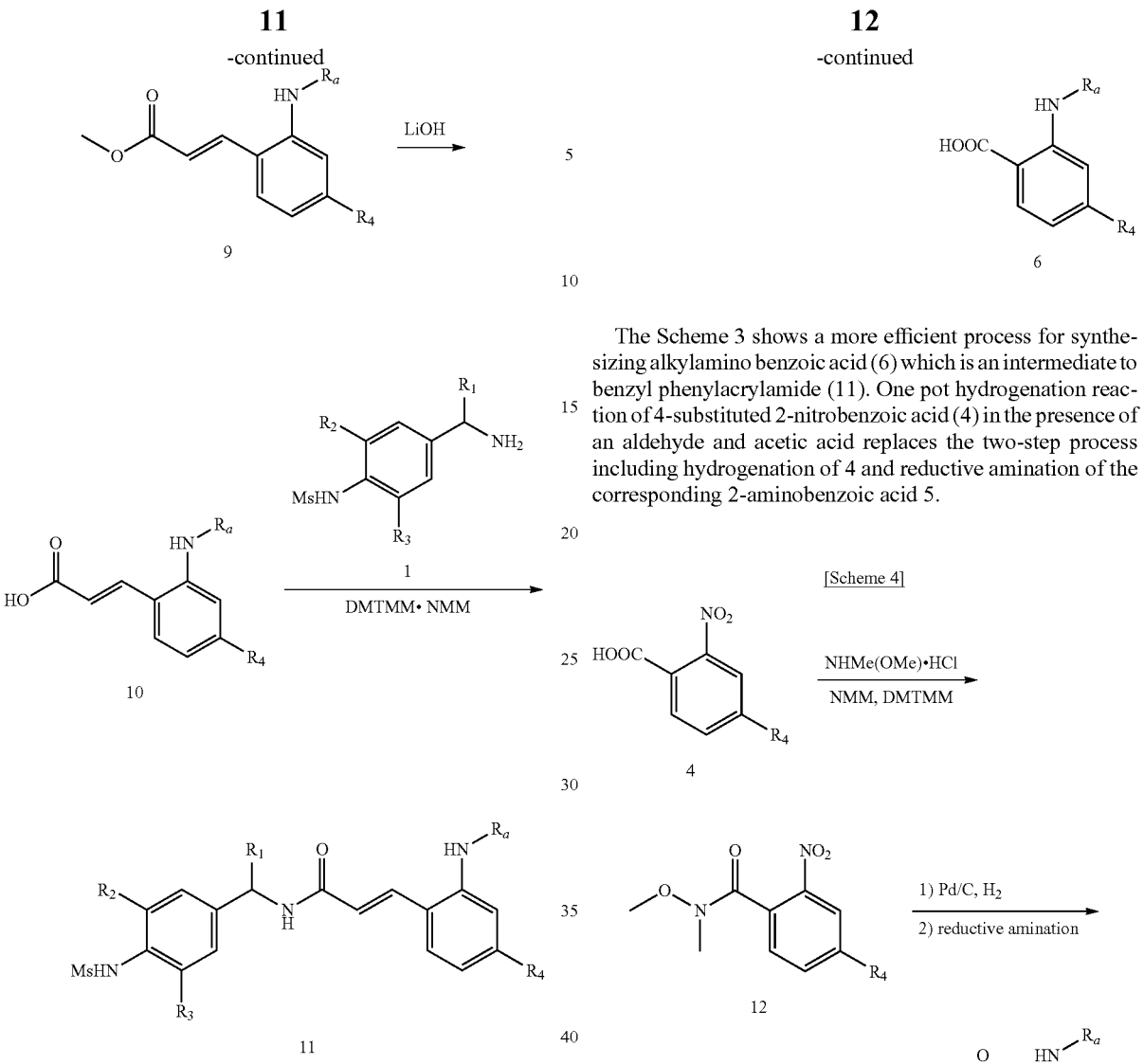

The Scheme 3 shows a more efficient process for synthesizing alkylamino benzoic acid (6) which is an intermediate to benzyl phenylacrylamide (11). One pot hydrogenation reaction of 4-substituted 2-nitrobenzoic acid (4) in the presence of an aldehyde and acetic acid replaces the two-step process including hydrogenation of 4 and reductive amination of the corresponding 2-aminobenzoic acid 5.

The Scheme 2 shows a proposed process for synthesizing acrylamide compound (11) with various substituents. 4-Substituted 2-aminobenzoic acid (5), which is prepared by hydrogenation of 4-substituted 2-nitrobenzoic acid (4), is converted to the corresponding alkylamino benzoic acid (6) via reductive amination. The substituted benzoic acid (6) is converted to the corresponding Weinreb amide (7), which is reduced by lithium aluminum hydride to yield substituted benzaldehyde (8). The benzaldehyde (8) is converted to methyl phenyl acrylic ester (9) by Wittig reaction. The methyl phenyl acrylic ester (9) is hydrolyzed with lithium hydroxide to yield phenyl acrylic acid (10). The phenyl acrylic acid (10) is reacted with substituted benzylamine (1) as shown in scheme 1 to yield benzyl phenylacrylamide (11).

The Scheme 4 shows an alternative process for synthesizing Weinreb amide (7) which is an intermediate to benzyl phenylacrylamide (11). 4-Substituted 2-nitrobenzoic acid (4) is converted to the corresponding Weinreb amide (12). Hydrogenation of the weinreb amide (12) followed by reductive amination with an aldehyde yields Weinreb amide (7).

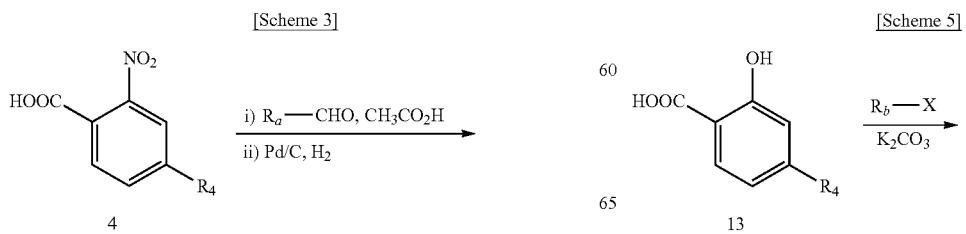

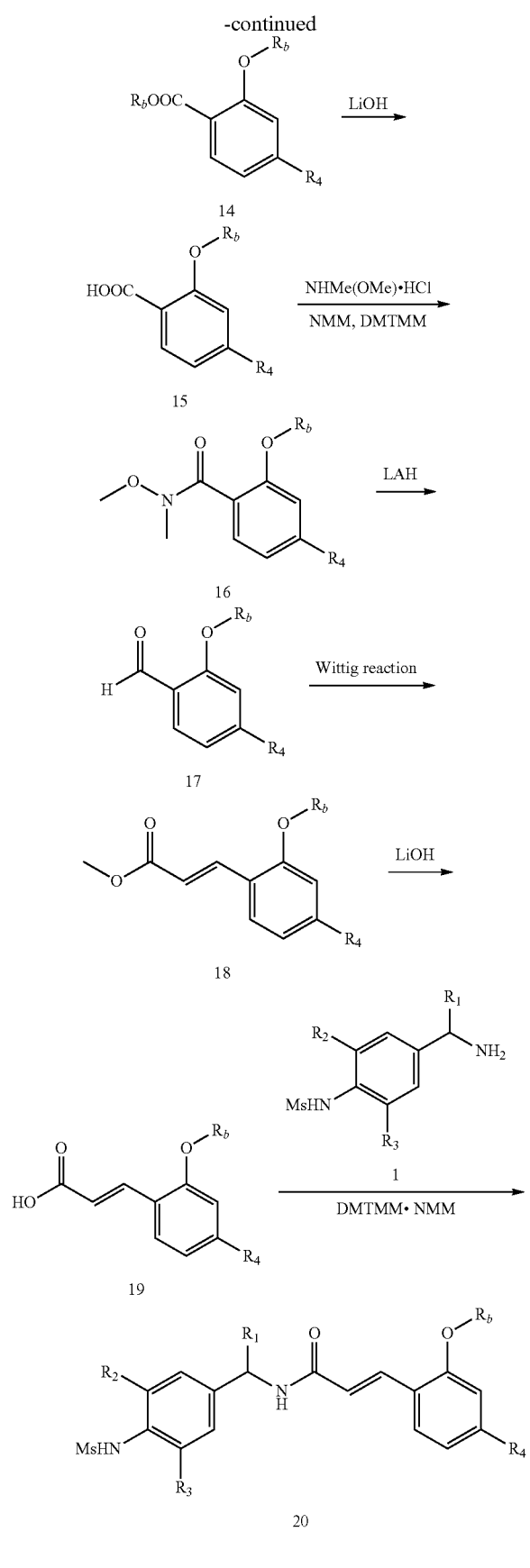

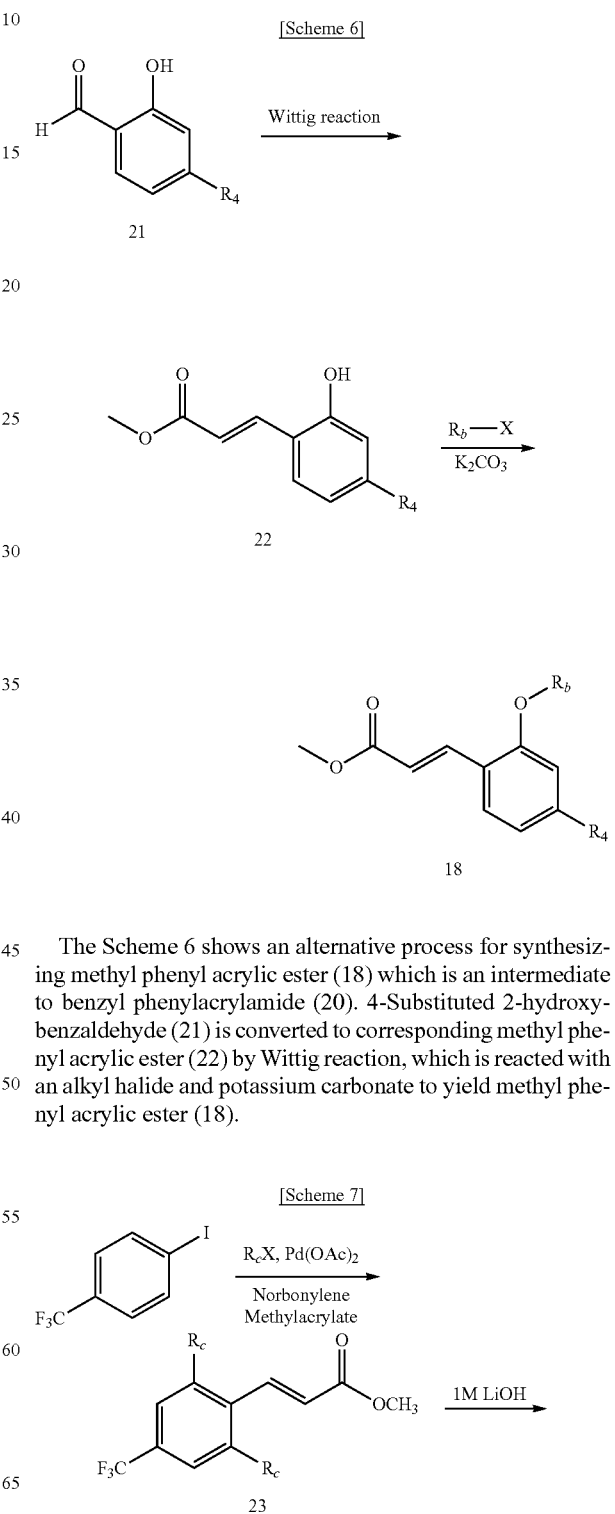

stituted 2-hydroxybenzoic acid (13) is reacted with an alkyl halide and potassium carbonate to yield corresponding alkoxy benzoate (14), which is hydrolyzed with lithium hydroxide to give alkoxy benzoic acid (15). The substituted benzoic acid (15) is converted to benzyl phenylacrylamide (20) by similar processes used for benzyl phenylacrylamide (11) shown in Scheme 2.

The Scheme 6 shows an alternative process for synthesizing methyl phenyl acrylic ester (18) which is an intermediate to benzyl phenylacrylamide (20). 4-Substituted 2-hydroxybenzaldehyde (21) is converted to corresponding methyl phenyl acrylic ester (22) by Wittig reaction, which is reacted with an alkyl halide and potassium carbonate to yield methyl phenyl acrylic ester (18).

The Scheme 5 shows a proposed process for synthesizing acrylamide compound (20) with various substituents. 4-Sub- -continued

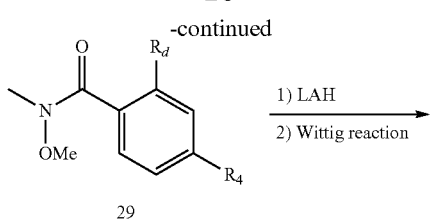

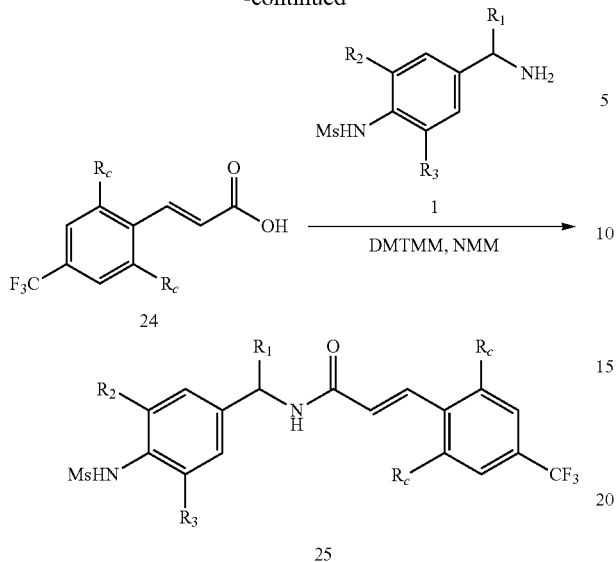

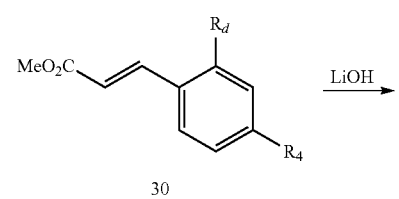

The Scheme 7 shows a proposed process for synthesizing acrylamide compound (25) with various substituents. 4-Trifluoromethyl iodobenzene is converted to substituted phenyl acrylic acid methyl ester (23) by palladium catalyzed coupling reaction. The phenyl acrylic acid methyl ester (23) is hydrolyzed with lithium hydroxide to yield phenyl acrylic acid (24). The phenyl acrylic acid (24) is reacted with substituted benzylamine (1) as described in Scheme 1 to yield benzyl phenylacrylamide (25).

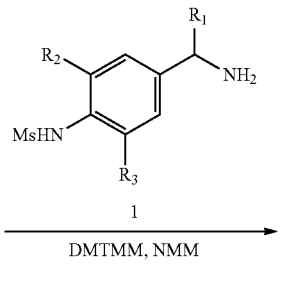

[Scheme 8]

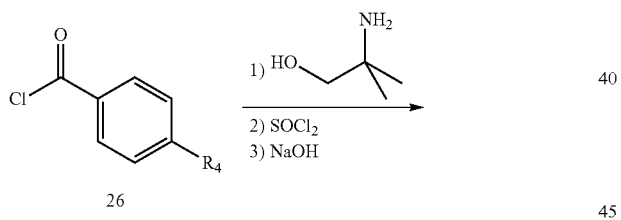

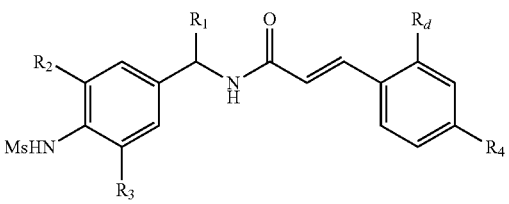

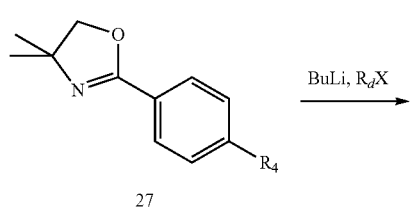

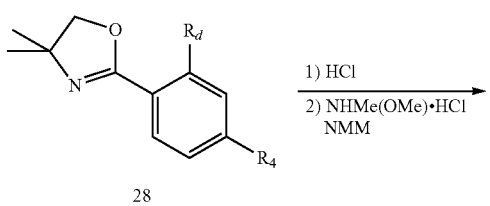

The Scheme 8 shows a proposed process for synthesizing acrylamide compound (32) with various substituents. Substituted benzoyl chloride (26) is reacted with 2-amino-2-methyl-1-propanol in the present of a base, and the resulting adduct is treated with thionyl chloride followed by sodium hydroxide to afford dihydro-oxazole compound (27). After treated with n-butyl lithium at low temperature, the compound 27 is reacted with an alkyl halide to give disubstituted dihydro-oxazole (28). The compound 28 is hydrolyzed with conc-HCl to the corresponding benzoic acid, which is converted to the Weinreb amide (29). After reducing compound 29 with lithium aluminum hydride, the resulting aldehyde is converted to the phenyl acrylic ester (30) under suitable Wittig reaction conditions. The acrylic ester (30) is hydrolyzed with lithium hydroxide to yield the corresponding acrylic acid (31). Substituted benzylamine (1) is reacted with acrylic acid (31) as described in Scheme 1 to yield benzyl phenylacrylamide (32).

[Scheme 9]

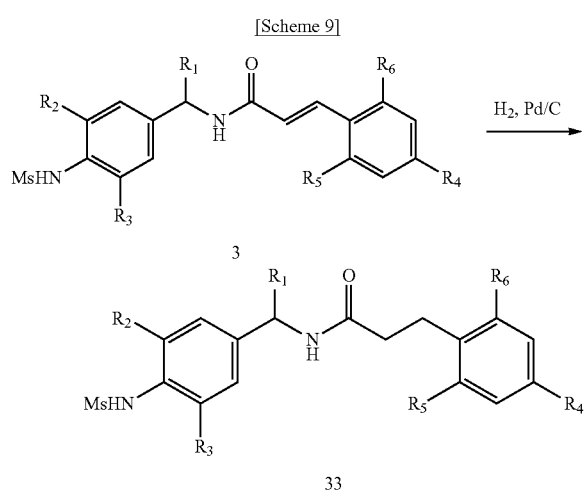

The Scheme 9 shows a proposed process for synthesizing amide compound (33) with various substituents. Substituted acrylamide (3) is reduced with Pd/C under hydrogen pressure to yield amide compound (33).

The present disclosure also provides to a compound of formula (Ia) or (I), an isomer thereof, or a pharmaceutically acceptable salt thereof for use as a medicament.

In one embodiment, the present disclosure also provides a pharmaceutical composition comprising a compound of formula (Ia) or (I), an isomer thereof, or a pharmaceutically acceptable salt thereof as an active ingredient and a pharmaceutically acceptable carrier.

In another embodiment, the present disclosure also provides a composition comprising a compound of formula (Ia) or (I), an isomer thereof, or a pharmaceutically acceptable salt thereof; and pharmaceutically acceptable carrier for preventing or treating a condition associated with the pathological stimulation and/or aberrant expression of vanilloid receptor.

In one preferred aspect, the present disclosure provides a pharmaceutical composition comprising a compound of formula (Ia) or (I), an isomer thereof, or a pharmaceutically acceptable salt thereof, for treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, and pancreatitis.

In a particularly preferred aspect, the present disclosure relates to the pharmaceutical composition comprising a compound of formula (Ia) or (I), an isomer thereof, or a pharmaceutically acceptable salt thereof for treating pain as described above, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), visceral pain, migraine, and other types of headaches.

The present disclosure also provides a pharmaceutical composition comprising a compound of formula (Ia) or (I), an isomer thereof, or a pharmaceutically acceptable salt thereof, which is characterized in that it is adapted for oral administration.

In one aspect, the present disclosure relates to the use of a compound of formula (Ia) or (I), an isomer thereof, or a pharmaceutically acceptable salt thereof for the preparation of a medicament In another aspect, the present disclosure relates to the use of a compound of formula (Ia) or (I), an isomer thereof, or a pharmaceutically acceptable salt thereof for the preparation of a medicament for the prevention or treatment of a condition that is associated with the aberrant expression and/or aberrant activation of a vanilloid receptor.

In a preferred aspect, the present disclosure relates to the use of a compound of formula (Ia) or (I), an isomer thereof, or a pharmaceutically acceptable salt thereof, in preparation of a medicament for the prevention or treatment of a condition that is selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis and pancreatitis.

In a particularly preferred aspect, the present disclosure relates to the use of the compound of formula (Ia) or (I), an isomer thereof, for preparing a medicament for preventing or treating pain as described above, wherein the condition is pain, which is or which is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), visceral pain, migraine, and other types of headaches.

In another aspect, the present disclosure relates to a method for inhibiting vanilloid ligand from binding to vanilloid receptor in a patient, comprising contacting cells expressing vanilloid receptor in the patient with the compound of formula (Ia) or (I), an isomer thereof, or a pharmaceutically acceptable salt thereof.

In another aspect, the present disclosure relates to a method for preventing or treating a condition associated with the pathological stimulation and/or aberrant expression of vanilloid receptors.

In another aspect, the present disclosure also provides a method for preventing or treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, and pancreatitis, which comprises administering to a mammal including a person in need thereof a therapeutically effective amount of the compound of formula (Ia) or (I), an isomer thereof, or a pharmaceutically acceptable salt thereof.

In a particularly preferred aspect, the present disclosure relates to the method of treating pain by administering a compound of formula (Ia) or (I), an isomer thereof, or a pharmaceutically acceptable salt thereof as described above, wherein the pain is or is associated with a condition selected from the group consisting of osteoarthritis, rheumatoid arthritis, ankylosing spondylitis, diabetic neuropathic pain, postoperative pain, dental pain, non-inflammatory musculoskeletal pain (including fibromyalgia, myofascial pain syndrome and back pain), visceral pain, migraine, and other types of headaches Hereinafter, the formulating methods and kinds of excipients will be described, but the present disclosure is not limited to them.

A compound of formula (Ia) or (I), an isomer thereof or a pharmaceutically acceptable salt thereof according to the present disclosure can be prepared as a pharmaceutical composition containing pharmaceutically acceptable carriers, adjuvants, diluents and the like. For instance, the compounds of the present disclosure can be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. For topical administration, the compounds of the present disclosure can be formulated in the form of ointment or cream.

The compound according to the present disclosure may also be used in the forms of pharmaceutically acceptable salts thereof, and may be used either alone or in combination or in admixture with other pharmaceutically active compounds.

The compounds of the present disclosure may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the disclosure may include any of conventional additives such as dissolving agents, isotonic agents, suspending agents, emulsifiers, stabilizers and preservatives.

The preferable dose level of the compounds according to the present disclosure depends upon a variety of factors including the condition and body weight of the patient, severity of the particular disease, dosage form, and route and period of administration, but may appropriately be chosen by those skilled in the art. The compounds of the present disclosure are preferably administered in an amount ranging from 0.001 to 100 mg/kg of body weight per day, and more preferably from 0.01 to 30 mg/kg of body weight per day. Doses may be administered once a day, or several times a day with each divided portions. The compounds of the present disclosure are used in a pharmaceutical composition in an amount of 0.0001 10% by weight, and preferably 0.001 1% by weight, based on the total amount of the composition.

The pharmaceutical composition of the present disclosure can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

Detailed Description of the Definitions

When describing the compounds, pharmaceutical compositions containing such compounds, methods of using such compounds and compositions, and use of such compounds and compositions, all terms used in the present application shall have the meaning usually employed by a relevant person skilled in the art, e.g. by a medicinal chemists, pharmacist or physician. By the way of example some definitions of specific groups are given below:

"Alkenyl" includes monovalent olefinically unsaturated hydrocarbyl groups being straight-chained or branched and having at least 1 double bond. "Alkenyl" has preferably 2-5 carbon atoms ("C1-C5 alkenyl"), 2-4 carbon atoms ("C2-C4 alkenyl"), or only 2-3 carbon atoms ("C2-C3 alkenyl"). Particular alkenyl groups include ethenyl (—CH=CH$_2$), n-propenyl (—CH$_2$CH=CH$_2$), isopropenyl (C(CH$_3$)=CH$_2$), and the like. A preferred "alkenyl" group is ethenyl (vinyl).

"Alkoxy" includes the group —OR wherein R is "alkyl" as defined further above. Particular alkoxy groups include, by way of example, methoxy, ethoxy, n-propoxy, isopropoxy, n-butoxy, tert-butoxy, iso-butoxy, sec-butoxy, n-pentoxy, 1,2-dimethylbutoxy, and the like.

"Alkoxyalkoxy" refers to the group —OROR', wherein R and R' are the same or different "alkyl" groups as defined further above.

"Alkoxyalkylamino" refers to the group —NH(ROR'), wherein R and R' are the same or different "alkyl" groups as defined further above.

"Alkyl" includes monovalent saturated aliphatic hydrocarbyl groups. The hydrocarbon chain may be either straight-chained or branched. "Alkyl" has 1-6 carbon atoms ("C1-C6 alkyl"), and in some instances preferably 1-5 carbon atoms ("C1-C5 alkyl"), 1-4 carbon atoms ("C1-C4 alkyl"), or only 1-3 carbon atoms ("C1-C3 alkyl"). This term is exemplified by groups such as methyl, ethyl, n-propyl, isopropyl, n-butyl, iso-butyl, sec-butyl, tert-butyl, t-amyl, and the like.

"Alkynyl" includes acetylenically unsaturated hydrocarbyl groups being straight-chained or branched and having at least 1 triple bond. "Alkynyl" has preferably 2-6 carbon atoms ("C2-C6 alkynyl"), and in some instances even more preferably 2-5 carbon atoms ("C1-C5 alkynyl"), 2-4 carbon atoms ("C2-C4 alkynyl"), or only 2-3 carbon atoms ("C2-C3 alkynyl"). A preferred alkynyl group is ethynyl (acetylenyl).

"Alkylamino" includes the group —NHR', wherein R' is alkyl group as defined herein.

"Dialkylamino" includes the group —NR'R", wherein R' and R" are alkyl group as defined herein.

"Cycloalkyl" refers to cyclic saturated aliphatic hydrocarbyl groups. The numbers of C-atoms referenced in connection with a given cycloalkyl group corresponds to the number of ring forming carbon atoms, e.g. "C3-C6 cycloalkyl" refers to a cycloalkyl with between three and six ring-forming C atoms. Examples of "cycloalkyl" are cyclopropyl, cyclobutyl, cyclopentyl, cyclohexyl etc. If indicated, a "cycloalkyl" group may be unsubstituted or substituted with one or more alkyl groups, e.g. with C1-C6 alkyl groups, preferably with C1-C3 alkyl groups, particularly preferably with methyl groups. If a "cycloalkyl" carries more than one alkyl substituent these substituents may be attached to the same or to different ring-forming carbon atoms.

"Cycloalkoxy" refers to the group —OR, wherein R is "cycloalkyl" group as defined further above.

"Cycloalkylamino" refers to the group —NHR, wherein R is "cycloalkyl" group as defined further above.

"Cycloalkylalkoxy" refers to the group —OR—R', wherein R is "alkyl" group and R' is "cycloalkyl" group as defined further above. Examples of "cycloalkylalkoxy" are cyclopropylmethoxy, cyclobutylmethoxy, cyclopentylmethoxy, cyclohexylmethoxy, cyclopropylethoxy, etc.

"Cyano" refers to the radical —C≡N.

"Ethenyl" or "vinyl" refers to —CH═CH$_2$ which is also designated "vinyl" in the present application.

"Ethynyl" or "acetylenyl" refers to —C≡H.

"Halo" or "halogen" refers to fluoro, chloro, bromo, and iodo. Preferred halo groups are either fluoro or chloro.

"Haloalkyl" includes an "alkyl" group as defined further above which is substituted with one or more halogens which may be the same, e.g. in trifluoromethyl or pentafluoroethyl, or which may be different.

"Isomer" refers to especially optical isomers (for example essentially pure enantiomers, essentially pure diastereomers, and mixtures thereof) as well as conformation isomers (i.e. isomers that differ only in their angles of at least one chemical bond), position isomers (particularly tautomers), and geometric isomers (e.g. cis-trans isomers).

"Essentially pure", e.g. in connection with enantiomers or diastereomers means at least about 90%, preferably at least about 95%, more preferably at least about 97 or at least about 98%, even more preferably at least about 99%, and particularly preferably at least about 99.5% (w/w) of a specified compound, e.g. a particular enantiomer or diastereomer.

"Pharmaceutically acceptable" means being devoid of substantial toxic effects when used in doses usually employed in a medicinal dosage, and thereby being approvable or preferably being approved by a regulatory agency of the Federal or a state government or being listed in the U.S. Pharmacopoeia or other generally recognized pharmacopoeia for use in animals, and more particularly in humans.

"Pharmaceutically acceptable salt" refers to a salt of a compound of the disclosure that is "pharmaceutically acceptable" as further defined herein, and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

"Pharmaceutically acceptable carrier" refers to a diluent, adjuvant, excipient or carrier with which a compound of the disclosure is administered and which is "pharmaceutically acceptable" as further defined herein.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans and non-human mammals. The term "patient" is used interchangeably with "subject" herein and shall include humans and non-human mammals unless specified otherwise.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder. In yet another embodiment, "treating" or "treatment" refers to reducing, modifying or removing one or more discernible symptom of a disease or disorder without modulating the cause of the underlying disease.

Mode for Carrying Out the Disclosure

The present disclosure is more specifically explained by following examples and experimental examples. However, it should be understood that the extent of the present disclosure is not limited to the following examples and experimental examples

EXAMPLE 1

(R)—N-[1-(3,5-Difluoro-4-methanesulfonylaminophenyl)-ethyl]-3-(2-propylamino-4-trifluoromethylphenyl)-acrylamide

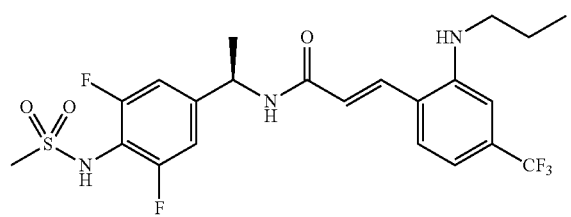 [SMILES: CCCNc1cc(C(F)(F)F)ccc1/C=C/C(=O)N[C@H](C)c1cc(F)c(NS(C)(=O)=O)c(F)c1]

Step 1: Synthesis of
2-amino-4-(trifluoromethyl)-benzoic acid

2-Nitro-4-trifluoromethyl-benzoic acid (3.07 g, 13.0 mmol) was stirred with Pd/C under hydrogen atmosphere for 2 hrs. The reaction mixture was filtered with celite to remove Pd/C. The filterate was concentrated in vacuo. The residue was extracted with CH$_2$Cl$_2$ (30 ml×3) and H$_2$O (30 ml). The combined organic layer was dried over MgSO$_4$ and then concentrated to yield title compound (2.66 g, 99%).

$^1$H NMR (300 MHz, DMSO-d$_6$): δ 7.82 (d, 1H), 7.02 (s, 1H), 7.05 (m, 1H), 2.41 (br, 1H)

Step 2: Synthesis of 2-propylamino-4-(trifluoromethyl)-benzoic acid

2-Amino-4-(trifluoromethyl)benzoic acid (714 mg, 3.48 mmol), propionylaldehyde (0.27 ml, 3.74 mmol), acetic acid (3.49 mmol) and sodium triacetoxyborohydride (1.12 g, 5.25 mmol) were added in THF (40 ml). The reaction mixture was stirred overnight. The reaction mixture was quenched by adding sat. NaHCO$_3$ (50 ml). The aqueous mixture was extracted with CH$_2$Cl$_2$ (30 ml×3). A combined organic layer was dried over MgSO$_4$, concentrated in vacuo, and purified with column chromatography to yield title compound (155 mg, 18%).

$^1$H NMR (300 MHz, CDCl$_3$): δ 8.04 (d, 1H, J=8.4 Hz), 6.89 (s, 1H), 6.79 (d, 1H, J=8.1 Hz), 3.21 (t, 2H, J=7.2 Hz), 1.75 (m, 2H), 1.02 (t, 3H, J=7.8 Hz).

Step 3: Synthesis of N-methoxy-N-methyl-2-propylamino-4-trifluoromethyl-benzamide 2-Propylamino-4-(trifluoromethyl)benzoic acid (147 mg, 0.594 mmol) in CH$_2$Cl$_2$ was reacted with N,O-dimethylhydroxy amine (82 mg), NMM (0.2 ml) and DMTMM (222 mg) at room temperature overnight. The reaction mixture was quenched by adding H$_2$O (3 ml). The reaction solvent was removed under reduced pressure. Water (30 ml) was added to the resulting residue, which was extracted with ethylacetate (30 ml×3). The combined organic layer was washed with sat. NaHCO$_3$ solution (30 ml), 1N HCl aqueous solution (30 ml) and brine (30 ml), and then dried over MgSO$_4$. The filterate was concentrated in vacuo. The residue was purified with column chromatography to yield the title compound (98 mg, 57%).

$^1$H NMR (300 MHz, CDCl$_3$): δ 7.43 (d, 1H, J=7.8 Hz) 6.85 (s, 1H), 6.82 (d, 1H), 3.56 (s, 3H), 3.34 (s, 3H), 3.10 (t, 2H, J=6.9 Hz), 1.71 (m, 2H), 1.01 (t, 3H, J=6.9 Hz).

Step 4: Synthesis of 3-(2-propylamino-4-trifluoromethyl-phenyl)-acrylic acid methyl ester N-Methoxy-N-methyl-2-propylamino-4-trifluoromethyl-benzamide (98.3 mg, 0.339 mmol) was reacted with 1M lithium aluminum hydride (0.6 ml) in THF (20 ml) at −40° C. for 1 hr. The reaction mixture was quenched by adding saturated potassium hydrogen sulfate solution. The mixture was stirred for 30 min. The reactions solvent was removed in vacuo. Water (30 ml) was added to the resulting residue, which was extracted with CH$_2$Cl$_2$ (30 ml×3). The combined organic layer was dried over MgSO$_4$ and concentrated in vacuo to yield 2-propylamino-4-trifluoromethyl-benzaldehyde (78 mg). 2-Propylamino-4-trifluoromethyl-benzaldehyde in toluene was reacted with methyl (triphenylphosphoranylidene) acetate (137 mg) at 100° C. overnight. The reaction solvent was removed in vacuo. Water (30 ml) was added to the resulting residue, which was extracted with ethyl acetate (30 ml×3). The combined organic layer was dried over MgSO$_4$ and filtered. The filterate was concentrated in vacuo and purified with column chromatography to yield title compound (67 mg, 69%).

$^1$H NMR (300 MHz, CDCl$_3$): δ 7.76 (d, 1H, J=15.9 Hz), 7.41 (d, 1H, J=8.1 Hz), 6.92 (d, 1H, J=8.7 Hz), 6.84 (s, 1H), 6.38 (d, 1H, J=15.6 Hz), 3.82 (s, 3H), 3.17 (m, 2H), 1.70 (m, 2H), 1.04 (t, 3H, J=7.8 Hz).

Step 5: Synthesis of 3-(2-propylamino-4-trifluoromethyl-phenyl)-acrylic acid 3-(2-Propylamino-4-trifluoromethyl-phenyl)-acrylic acid methyl ester (67.3 mg, 0.234 mmol) was reacted with aqueous 1N LiOH solution (5 ml) in THF/CH$_3$OH (10 ml/5 ml) for 1 hr. The reaction solvent removed in vacuo. Water (30 ml) was added to the resulting residue, which was neutralized with 1N HCl solution, an then extracted with ethyl acetate (30 ml×3). The combined organic layer was dried over MgSO$_4$ and concentrated in vacuo to yield title compound (55 mg, 0.201 mmol, 86%).

$^1$H NMR (300 MHz, CDCl$_3$): δ 7.80 (d, 1H, J=15.6 Hz), 7.48 (d, 1H, J=7.5 Hz), 6.82 (s, 1H), 6.79 (s, 1H), 6.36 (d, 1H, J=15.6 Hz), 3.10 (t, 2H, J=6.9 Hz), 1.75 (m, 2H), 0.97 (t, 3H, J=7.5 Hz)

Step 6: Synthesis of (R)—N-[1-(3,5-difluoro-4-methanesulfonylamino-phenyl)-ethyl]-3-(2-propylamino-4-trifluoromethyl-phenyl)-acrylamide (R)—N-(4-Aminoethyl-2,6-difluoro-phenyl)-methanesulfonamide, HCl salt (70 mg, 0.24 mmol) in THF was reacted with 3-(2-propylamino-4-trifluoromethyl-phenyl)-acrylic acid (55 mg, 0.20 mmol), NMM (0.2 ml) and DMTMM (86 mg, 0.34 mmol) at room temperature overnight. The reaction mixture was quenched by adding H$_2$O. The reaction solvent was removed in vacuo. Water (30 ml) was added to the resulting residue, which was extracted with ethyl acetate (30 ml×3). The combined organic layer was dried over MgSO$_4$. The filterate was concentrate under reduced pressure and purified with column chromatography to yield the title compound (35 mg, 59%).

$^1$H NMR (300 MHz, CDCl$_3$): δ 7.79 (d, 1H, J=15 Hz), 7.37 (d, 1H, J=7.8 Hz), 6.96 (d, 1H, J=8.4 Hz), 6.86 (d, 1H, J=8.1 Hz), 6.82 (s, 1H), 6.48 (br, 1H), 6.33 (d, 1H, J=15.3 Hz), 5.93 (d, 1H, J=7.2 Hz), 5.15 (t, 1H, J=7.2 Hz), 3.19 (s, 3H), 3.14 (t, 2H, J=7.2 Hz), 1.70 (m, 2H), 0.97 (t, 3H, J=7.5 Hz)

ESI [M−H]$^−$: 504

EXAMPLE 2

N-(3,5-Difluoro-4-methanesulfonylamino-benzyl)-3-(2-propylamino-4-trifluoromethyl-phenyl)-acrylamide

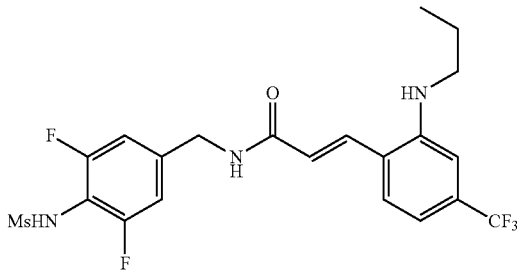

N-(4-Aminomethyl-2,6-difluoro-phenyl)-methanesulfonamide, HCl salt (84 mg, 0.308 mmol) was reacted with 3-(2-propylamino-4-trifluoromethyl-phenyl)-acrylic acid (67 mg, 0.245 mmol), NMM (0.4 ml) and DMTMM (121 mg) to give the title compound (62 mg, 52%).

$^1$H NMR (300 MHz, CDCl$_3$): δ 7.75 (d, 1H, J=15.6 Hz), 7.33 (d, 1H, J=7.8 Hz), 6.95 (d, 1H, J=8.4 Hz), 6.84 (d, 1H, J=8.1 Hz), 6.79 (s, 1H), 6.30 (d, 1H, J=15.6 Hz), 6.03 (br, 1H), 4.59 (br, 1H, J=6.9 Hz), 4.50 (d, 2H, J=6.0 Hz), 3.16 (s, 3H), 3.12 (t, 2H, J=7.2 Hz), 1.64 (m, 2H), 0.96 (t, 3H, J=7.5 Hz)

EXAMPLE 3

(R)-3-(2-Butylamino-4-trifluoromethyl-phenyl)-N-[1-(3,5-difluoro-4-methanesulfonylamino-phenyl)-ethyl]-acrylamide

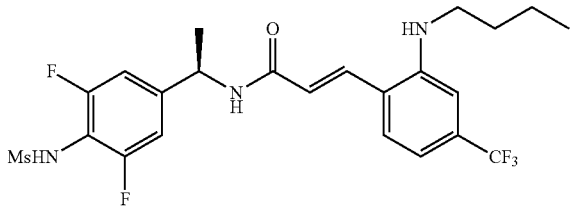

(R)—N-[4-(1-Amino-ethyl)-2,6-difluoro-phenyl]-methanesulfonamide, HCl salt (25 mg, 0.09 mmol) was reacted with 3-(2-butylamino-4-trifluoromethyl-phenyl)-acrylic acid (25 mg, 0.09 mmol) to give the title compound (15 mg, 32%) after purification by crystallization from Hex/EtOAc.

$^1$H NMR (300 MHz, CDCl$_3$): δ 7.75 (d, 1H, J=15.3 Hz), 7.37 (d, 1H, J=8.4 Hz), 7.00 (m, 2H), 6.90 (d, 1H, J=8.4 Hz), 6.83 (s, 1H), 6.33 (d, 1H, J=15.3 Hz), 6.12 (s, 1H), 5.83 (d, 1H, J=7.8 Hz), 5.18 (m, 1H), 4.18 (bs, 1H), 3.21 (s, 3H), 3.17 (m, 2H), 1.48 (m, 5H), 0.97 (t, 3H, J=7.5 Hz).

ESI [M−H]$^-$: 518

EXAMPLE 4

N-(3,5-Difluoro-4-methanesulfonylamino-benzyl)-3-(2-propoxy-4-trifluoromethyl-phenyl)-acrylamide

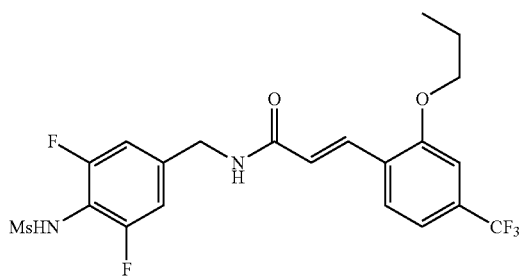

Step 1: Synthesis of 2-propoxy-4-trifluoromethyl-benzoic acid propyl ester

2-Hydroxy-4-trifluoromethyl-benzoic acid (673 mg, 3.26 mmol) was reacted with propylbromide (0.85 ml) and K$_2$CO$_3$ (1.42 g) in DMF (15 ml) at 65° C. overnight. The reaction mixture was quenched by adding 10 ml of H$_2$O. The mixture was extracted with ethylacetate (30 ml×3). A combined organic layer was washed with H$_2$O (50 ml×6) and brine (50 ml), and dried over MgSO$_4$. The filterate was concentrated in vacuo to yield title compound (908 mg, 99%)

$^1$H NMR (300 MHz, CDCl$_3$): δ 7.83 (d, 1H, J=8.1 Hz), 7.21 (d, 1H, J=8.1 Hz), 7.15 (s, 1H), 4.28 (t, 2H, J=6.9 Hz), 4.03 (t, 2H, J=6.3 Hz), 1.88 (m, 2H), 1.82 (m, 2H), 1.07 (m, 6H)

Step 2: Synthesis of 2-propoxy-4-trifluoromethyl-benzoic acid

2-Propoxy-4-trifluoromethyl-benzoic acid propyl ester (957 mg, 3.44 mmol) was reacted with 1N LiOH (10 ml) at room temperature for 4 hrs. The reaction solvent was removed in vacuo. Water (30 ml) was added to the resulting residue, which was neutralized with 1 N aqueous HCl solution. The aqueous mixture was extracted with ethylacetate (30 ml×3). A combined organic layer was dried over MgSO$_4$, and concentrated in vacuo to yield quantitatively title compound.

$^1$H NMR (300 MHz, CDCl$_3$): δ 8.32 (d, 1H, J=7.8 Hz), 7.40 (d, 1H, J=8.1 Hz), 7.16 (s, 1H), 4.28 (t, 2H, J=6.6 Hz), 1.98 (m, 2H), 1.26 (m, 3H)

Step 3: Synthesis of N-methoxy-N-methyl-2-propoxy-4-trifluoromethyl-benzamide 2-Propoxy-4-(trifluoromethyl)benzoic acid (457 mg, 1.93 mmol) in THF was reacted with N,O-dimethylhydroxy amine (378 mg), NMM (0.65 ml) and DMTMM (947 mg) at room temperature overnight. The reaction solvent was removed in vacuo. Water (30 ml) was added to the resulting residue, which was extracted with ethyl acetate (30 ml×3). The combined organic layer was washed with 1 M NaHCO$_3$ (30 ml), 1N HCl (30 ml) and brine (30 ml) and dried over MgSO$_4$. The filterate was purified with column chromatography (Hex/EtOAc=4/1) to yield the title compound (277 mg, 49%).

$^1$H NMR (300 MHz, CDCl$_3$): δ 7.36 (d, 1H, J=7.8 Hz), 7.25 (d, 1H, J=8.1 Hz), 7.12 (s, 1H), 4.01 (t, 2H, J=6.3 Hz), 3.46 (s, 3H), 3.35 (br, 3H), 1.83 (m, 2H), 1.03 (t, 3H, J=6.9 Hz)

Step 4: Synthesis of 2-propoxy-4-trifluoromethyl-benzaldehyde

N-Methoxy-N-methyl-2-propoxy-4-trifluoromethyl-benzamide (277 mg) in THF was reacted with 1 M LAH (1 ml) on −50° C. for 1 hr. The reaction mixture was quenched by adding aqueous potassium hydrogen sulfate (5 ml). The mixture was stirred for 30 min. The reaction solvent was removed in vacuo. Water (30 ml) was added to the resulting residue, which was extracted with ethyl acetate (30 ml×3). The combined organic layer was washed with brine (30 ml) and dried over MgSO$_4$ and concentrated in vacuo to yield title compound (232 mg, 100%).

$^1$H NMR (300 MHz, CDCl$_3$): δ 10.54 (s, 1H), 7.93 (d, 1H, J=8.1 Hz), 7.27 (d, 1H, J=8.1 Hz), 7.21 (s, 1H), 4.10 (t, 2H, J=6.6 Hz), 1.91 (m, 2H), 1.10 (t, 3H, J=7.2 Hz)

Step 5: Synthesis of 3-(2-propoxy-4-trifluoromethyl-phenyl)-acrylic acid methyl ester 2-Propoxy-4-trifluoromethyl-benzaldehyde (232 mg, 1 mmol) in toluene was reacted with methyl (triphenylphosphoranylidene)acetate (382 mg, 1.14 mmol) at 110° C. overnight. The reaction solvent was removed under reduced pressure. Water (30 ml) was added to the resulting residue, which was extracted with ethyl acetate (30 ml×3). The combined organic layer was washed with brine (30 ml) and dried over MgSO₄. The filterate was purified with column chromatography to yield title compound (198 mg, 69%).

¹H NMR (300 MHz, CDCl₃): δ 7.98 (d, 1H, J=16.2 Hz), 7.58 (d, 1H, J=8.1 Hz), 7.21 (m, 1H), 7.11 (s, 1H), 6.60 (d, 1H, J=16.2 Hz), 4.04 (t, 2H, J=6.0 Hz), 3.81 (s, 3H), 1.91 (m, 2H), 1.09 (t, 3H, J=7.5 Hz).

Step 6: Synthesis of 3-(2-propoxy-4-trifluoromethyl-phenyl)-acrylic acid 3-(2-Propoxy-4-trifluoromethyl-phenyl)-acrylic acid methyl ester (198 mg) was reacted with 1N LiOH (5 ml) in THF (10 ml) and CH₃OH (5 ml) for 1 hr. The reaction mixture was concentrated in vacuo. Water (30 ml) was added to the resulting residue, which was neutralized with 1N HCl solution. The mixture was extracted with ethyl acetate (30 ml×3). The combined organic layer was dried over MgSO₄. The filterate was concentrated in vacuo to yield title compound (136 mg, 72%).

¹H NMR (300 MHz, CDCl₃): δ 7.93 (d, 1H, J=16.2 Hz), 7.71 (d, 1H, J=8.4 Hz), 7.21 (m, 1H), 7.12 (s, 1H), 6.59 (d, 1H, J=16.2 Hz), 4.04 (t, 2H, J=6.0 Hz), 1.78 (m, 2H), 1.06 (t, 3H, J=7.5 Hz)

Step 7: Synthesis of N-(3,5-difluoro-4-methanesulfonylamino-benzyl)-3-(2-propoxy-4-trifluoromethyl-phenyl)-acrylamide N-(4-Aminomethyl-2,6-difluoro-phenyl)-methanesulfonamide, HCl salt (78 mg, 0.286 mmol) in THF was reacted with 3-(2-propoxy-4-trifluoromethyl-phenyl)-acrylic acid (67 mg, 0.246 mmol), NMM (0.2 ml) and DMTMM (86 mg) to give the title compound (92 mg, 76%) after column chromatography (Hex/EtOAc=1/1).

¹H NMR (300 MHz, CDCl₃): δ 7.90 (d, 1H, J=15.9 Hz), 7.52 (d, 1H, J=8.4 Hz), 7.21 (m, 1H), 7.06 (s, 1H), 6.93 (d, 1H, J=7.8 Hz), 6.55 (d, 1H, J=16.2 Hz), 5.96 (br, 1H), 4.51 (d, 2H, J=6.0 Hz), 4.00 (t, 2H, J=6.0 Hz), 3.16 (s, 3H), 1.87 (m, 2H), 1.04 (t, 3H, J=7.5 Hz)

ESI [M−H]⁻: 505

EXAMPLE 5

(R)—N-[1-(3,5-Difluoro-4-methanesulfonylamino-phenyl)-ethyl]-3-(2-propoxy-4-trifluoromethyl-phenyl)-acrylamide

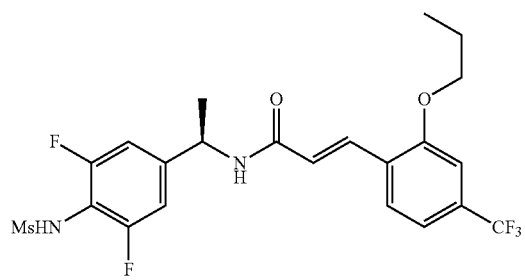

(R)—N-(4-Aminoethyl-2,6-difluoro-phenyl)-methanesulfonamide, HCl salt (81 mg, 0.28 mmol) was reacted with 3-(2-propoxy-4-trifluoromethyl-phenyl)-acrylic acid (68 mg, 0.25 mmol), NMM (0.2 ml) and DMTMM (86 mg) at room temperature overnight to yield the title compound (89 mg, 72%) after column chromatography (Hex/EtOAc=1/1).

¹H NMR (300 MHz, CDCl₃): δ 7.92 (d, 1H, J=15.6 Hz), 7.55 (d, 1H, J=7.8 Hz), 7.19 (d, 1H, J=10.8 Hz), 7.10 (s, 1H), 6.99 (d, 1H, J=8.7 Hz), 6.55 (d, 1H, J=15.9 Hz), 5.99 (br, 1H), 5.78 (br, 1H), 5.19 (m, 1H), 4.03 (t, 2H, J=6.6 Hz), 3.20 (s, 3H), 1.90 (m, 2H), 1.08 (t, 3H, J=7.5 Hz)

EXAMPLE 6

(R)—N-[1-(3,5-Difluoro-4-methanesulfonylamino-phenyl)-ethyl]-3-(2,6-dipropyl-4-trifluoromethyl-phenyl)-acrylamide

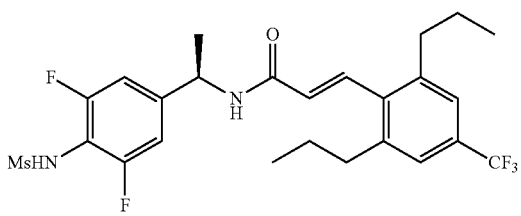

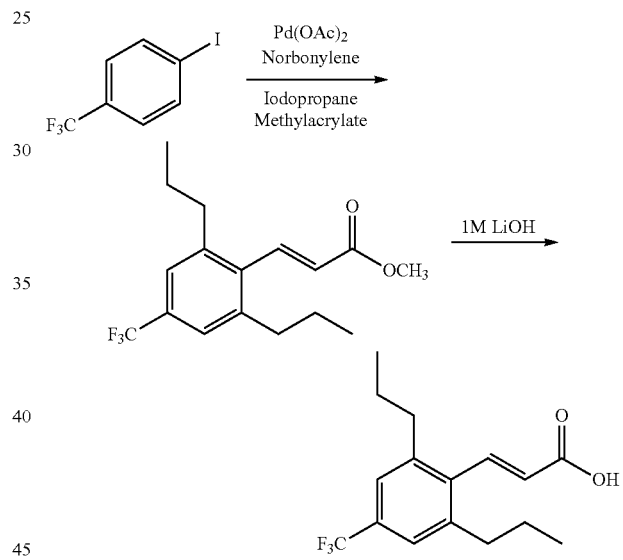

Step 1: Synthesis of 3-(2,6-dipropyl-4-trifluoromethyl-phenyl)-acrylic acid methyl ester In a 100 ml flask, 4-iodobenzotrifluoride (1 g, 3.68 mmol) was dissolved in 10 ml DMF, and Pd(OAc)₂ (165 mg, 0.2 eq), K₂CO₃ (2.54 g, 5.0 eq), KOAc (1.8 g, 5.0 eq), norbornylene (692 mg, 1.0 eq), methyl acrylate (0.33 ml, 1.0 eq), and iodopropane (3.75 g, 6.0 eq) were added stepwise at room temperature. The resulting reaction mixture was stirred for 3 days. After the completion of the reaction, the Na₂S₂O₃ solution was poured into the reaction mixture, which was stirred for 30 minutes, extracted with EtOAc 50 ml (3 times), and dried with anh. MgSO₄. The organic layer was filtered, concentrated in vacuo, and purified with column chromatography (Hexane: EtOAc=8:1) to give the title compound (0.343 g, 30%).

¹H NMR (300 MHz, CDCl₃): δ 7.83 (d, 1H, J=16.2 Hz), 7.31 (s, 2H), 6.01 (d, 1H, J=16.2 Hz), 3.84 (s, 3H), 2.62 (m, 4H), 1.58 (m, 4H), 0.94 (m, 6H).

Step 2: Synthesis of 3-(2,6-dipropyl-4-trifluoromethyl-phenyl)-acrylic acid 3-(2,6-Dipropyl-4-trifluoromethyl-phenyl)-acrylic acid methyl ester (343 mg) was reacted with 1N LiOH (5 ml) in THF (10 ml) and $CH_3OH$ (5 ml) for 1 hr. The reaction mixture was concentrated in vacuo. Water (30 ml) was added to the resulting residue, which was neutralized with 1N HCl solution. The mixture was extracted with ethyl acetate (30 ml×3). The combined organic layer was dried over $MgSO_4$. The filterate was concentrated in vacuo to yield title compound (250 mg, 82%).

Step 3: Synthesis of (R)—N-[1-(3,5-difluoro-4-methanesulfonylamino-phenyl)-ethyl]-3-(2,6-dipropyl-4-trifluoromethyl-phenyl)-acrylamide (R)—N-[4-(1-Amino-ethyl)-2,6-difluoro-phenyl]-methanesulfonamide, HCl salt (250 mg, 0.87 mmol) was reacted with 3-(2,6-dipropyl-4-trifluoromethyl-phenyl)-acrylic acid (261 mg, 0.87 mmol) to give the title compound (181 mg, 39%) after purification by crystallization from Hex/EtOAc.

$^1$H NMR (300 MHz, DMSO-d6): δ 9.49 (s, 1H), 8.70 (t, 1H, J=7.5 Hz), 7.56 (d, 1H, J=15.9 Hz), 7.42 (s, 2H), 7.15 (m, 2H), 6.23 (d, 1H, J=16.2 Hz), 5.05 (m, 1H), 3.05 (s, 3H), 2.61 (m, 4H), 1.51 (m, 4H), 1.41 (d, 3H, J=7.2 Hz), 0.88 (m, 6H). ESI [M−H]$^-$: 531

EXAMPLE 7

(R)—N-[1-(3,5-Difluoro-4-methanesulfonylamino-phenyl)-ethyl]-3-(2-ethoxy-4-trifluoromethyl-phenyl)-acrylamide

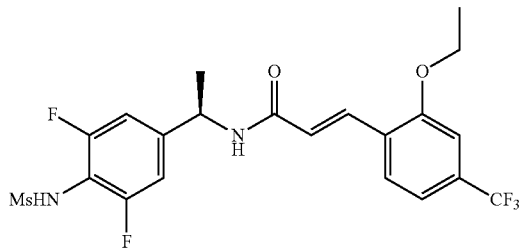

Step 1: Synthesis of 2-ethoxy-4-trifluoromethyl-benzoic acid

2-Hydroxy-4-trifluoromethyl-benzoic acid (1.20 g, 5.82 mmol) was reacted with ethyliodide (2.2 eq) and $K_2CO_3$ (1.69 g) in DMF solution. The reaction mixture was quenched by adding $H_2O$. The mixture was extracted with ethyl acetate (40 ml×3). A combined organic layer was washed sat $NaHCO_3$ solution (30 ml), $H_2O$ (40 ml×5), and brine, and then dried over $MgSO_4$. The filterate was concentrated in vacuo to yield 2-ethoxy-4-trifluoromethyl benzoic acid ethyl ester. The ester obtained above was reacted with 1 N LiOH (15 ml) in THF and $CH_3OH$ cosolvent for 2 hrs as described above to yield title compound (1.20 g, 88%)

$^1$H NMR (300 MHz, CDCl$_3$): δ 8.32 (d, 1H, J=8.1 Hz), 7.40 (d, 1H, J=8.1 Hz), 7.26 (s, 1H), 4.40 (q, 2H, J=6.9 Hz), 1.62 (t, 3H, J=6.9 Hz)

Step 2: Synthesis of N-methoxy-N-methyl-2-ethoxy-4-trifluoromethyl-benzamide 2-Ethoxy-4-trifluoromethyl-benzoic acid (1.20 g, 5.12 mmol) was reacted with N,O-dimethylhydroxy amine (609 mg), NMM (0.95 ml) and DMTMM (1.47 mg) as described above to give the title compound (1.04 g, 73%) after column chromatography (Hex/EtOAc=5/1).

$^1$H NMR (300 MHz, CDCl$_3$): δ 7.40 (br, 1H), 7.23 (br, 1H), 7.10 (s, 1H), 4.13 (t, 2H, J=6.3 Hz), 3.49 (s, 3H), 3.37 (br, 3H), 1.42 (t, 3H, J=6.9 Hz)

Step 3: Synthesis of 2-ethoxy-4-trifluoromethyl-benzaldehyde

N-Methoxy-N-methyl-2-ethoxy-4-trifluoromethyl-benzamide (1.04 g) was reacted with 1 M LAH (1 ml) at −40° C. for 2 hrs as described above to yield title compound (729 mg, 65%)

$^1$H NMR (300 MHz, CDCl$_3$): δ 10.52 (s, 1H), 7.93 (d, 1H, J=8.1 Hz), 7.27 (d, 1H, J=8.1 Hz), 7.20 (s, 1H), 4.21 (q, 2H, J=6.6 Hz), 1.52 (t, 3H, J=6.9 Hz)

Step 4: Synthesis of 3-(2-ethoxy-4-trifluoromethyl-phenyl)-acrylic acid methyl ester 2-Ethoxy-4-trifluoromethyl-benzaldehyde (729 mg, 3.34 mmol) was reacted with methyl (triphenylphosphoranylidene)acetate (1.45 g, 4.34 mmol) at 110° C. overnight as described above to yield title compound (476.5 mg, 52%).

$^1$H NMR (300 MHz, CDCl$_3$): δ 7.97 (d, 1H, J=16.5 Hz), 7.58 (d, 1H, J=16.2 Hz), 7.58 (d, 1H, J=7.8 Hz), 7.21 (m, 1H), 7.11 (s, 1H), 6.60 (d, 1H, J=15.9 Hz), 4.14 (q, 2H, J=6.9 Hz), 3.82 (s, 3H), 1.58 (t, 3H, J=7.5 Hz)

Step 5: Synthesis of 3-(2-ethoxy-4-trifluoromethyl-phenyl)-acrylic acid 3-(2-Ethoxy-4-trifluoromethyl-phenyl)-acrylic acid methyl ester (477 mg, 1.74 mmol) was reacted with 1N LiOH (7.5 ml) in THF and $CH_3OH$ for 1.5 hrs as described above to yield title compound (440 mg, 97%)

$^1$H NMR (300 MHz, CDCl$_3$): δ 8.07 (d, 1H, J=16.2 Hz), 7.62 (d, 1H, J=8.1 Hz), 7.26 (m, 1H), 7.12 (s, 1H), 6.62 (d, 1H, J=16.2 Hz), 4.16 (q, 2H, J=6.9 Hz), 1.52 (t, 3H, J=6.9 Hz)

Step 6: Synthesis of (R)—N-[1-(3,5-difluoro-4-methanesulfonylamino-phenyl)-ethyl]-3-(2-ethoxy-4-trifluoromethyl-phenyl)-acrylamide (R)—N-(4-Aminoethyl-2,6-difluoro-phenyl)-methanesulfonamide, HCl salt (70 mg, 0.24 mmol) was reacted with 3-(2-ethoxy-4-trifluoromethyl-phenyl)-acrylic acid (59 mg, 0.22 mmol), NMM (0.2 ml) and DMTMM (73 mg, 0.26 mmol) to give the title compound (77 mg, 69%) after column chromatography (Hex/EtOAc=1/1).

$^1$H NMR (300 MHz, CDCl$_3$): δ 7.94 (d, 1H, J=15.9 Hz), 7.56 (d, 1H, J=8.1 Hz), 7.19 (d, 1H, J=8.1 Hz), 7.09 (s, 1H), 6.75 (d, 1H, J=8.1 Hz), 6.57 (d, 1H, J=15.9 Hz), 6.08 (br, 1H), 5.87 (d, 1H, J=7.8 Hz), 5.20 (t, 1H) 4.13 (q, 2H, J=6.9 Hz), 3.20 (s, 3H), 1.52 (t, 3H, J=7.5 Hz)

ESI [M−H]$^-$: 491

EXAMPLE 8

N-(3,5-Difluoro-4-methanesulfonylamino-benzyl)-3-(2-ethoxy-4-trifluoromethyl-phenyl)-acrylamide

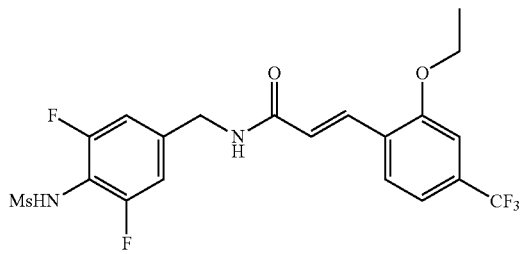

N-(4-Aminomethyl-2,6-difluoro-phenyl)-methanesulfonamide, HCl salt (60 mg, 0.22 mmol) was reacted with 3-(2-ethoxy-4-trifluoromethyl-phenyl)-acrylic acid (52 mg, 0.20 mmol), NMM (0.2 ml) and DMTMM (73 mg, 0.25 mmol) at room temperature to yield the title compound (50 mg, 52%) after column chromatography (Hex/EtOAc=1/1).

$^1$H NMR (300 MHz, CDCl$_3$): δ 7.94 (d, 1H, J=15.6 Hz), 7.56 (d, 1H, J=7.8 Hz), 7.21 (d, 1H, J=7.8 Hz), 7.11 (s, 1H), 7.00 (m, 2H), 6.77 (d, 1H, J=8.4 Hz), 6.62 (d, 1H, J=15.9 Hz), 6.03 (br, 1H), 4.56 (d, 2H, J=6.0 Hz), 4.15 (q, 2H, J=7.2 Hz), 3.21 (s, 3H), 1.48 (t, 3H, J=7.2 Hz)

EXAMPLE 9

(R)—N-[1-(3-Fluoro-4-methanesulfonylamino-phenyl)-ethyl]-3-(2-ethoxy-4-trifluoromethyl-phenyl)-acrylamide

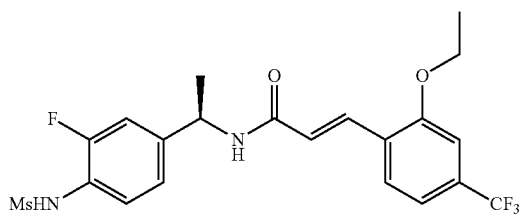

(R)—N-(4-Aminoethyl-2-fluoro-phenyl)-methanesulfonamide, HCl salt (60 mg, 0.22 mmol) was reacted with 3-(2-ethoxy-4-trifluoromethyl-phenyl)-acrylic acid (51 mg, 0.19 mmol), NMM (0.2 ml) and DMTMM (72 mg) at room temperature overnight to yield the title compound (62 mg, 0.13 mmol, 68%) after column chromatography (Hex/EtOAc=1/1).

$^1$H NMR (300 MHz, CDCl$_3$): δ 7.91 (d, 1H, J=15.6 Hz), 7.55 (m, 1H), 7.44 (m, 1H), 7.15 (d, 1H, J=9.0 Hz), 7.08 (s, 1H), 6.93 (m, 1H), 6.55 (d, 1H, J=15.0 Hz), 5.95 (br, 1H), 5.87 (d, 1H, J=7.8 Hz), 5.21 (t, 1H) 4.14 (q, 2H, J=6.9 Hz), 3.02 (s, 3H), 1.53 (t, 3H, J=7.5 Hz)

EXAMPLE 10

(R)—N-[1-(3,5-Difluoro-4-methanesulfonylamino-phenyl)-ethyl]-3-(2-ethylamino-4-trifluoromethyl-phenyl)-acrylamide

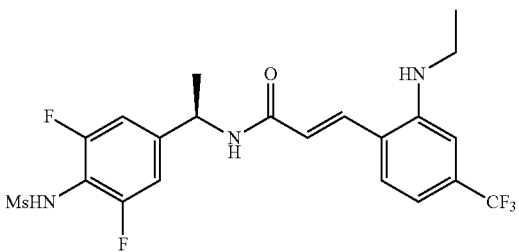

Step 1: Synthesis of N-methoxy-N-methyl-2-nitro-4-trifluoromethyl-benzamide

2-Nitro-4-trifluoromethyl-benzoic acid (2.753 mg, 11.7 mmol) in THF was reacted with N,O-dimethylhydroxy amine (1.277 g, 13.1 mmol), NMM (3 ml) and DMTMM (3.34 g) at room temperature overnight. The reaction mixture was quenched by adding H$_2$O. The mixture was extracted with ethyl acetate (50 ml×3). The combined organic layer was washed 1M NaHCO$_3$ (50 ml×2), 3% HCl (50 ml×2) and brine (50 ml), and then dried over MgSO$_4$. The filterate was concentrated in vacuo to yield the title compound (2.84 g, 87%).

$^1$H NMR (300 MHz, CDCl$_3$): δ 8.43 (s, 1H), 7.99 (d, 1H, J=8.1 Hz), 7.69 (d, 1H, J=7.8 Hz), 3.39 (s, 6H)

Step 2: Synthesis of 2-amino-N-methoxy-N-methyl-4-trifluoromethyl-benzamide

N-Methoxy-N-methyl-2-nitro-4-trifluoromethyl-benzamide (2.54 g, 9.12 mmol) was reacted with Pd/C (441 mg) under hydrogen atmosphere as described above to yield title compound.

$^1$H NMR (300 MHz, CDCl$_3$): δ 7.47 (d, 1H, J=7.8 Hz), 6.93 (s, 1H), 6.91 (d, 1H, J=7.8 Hz), 3.56 (s, 3H), 3.36 (s, 3H).

Step 3: Synthesis of 2-ethylamino-N-methoxy-N-methyl-4-trifluoromethyl-benzamide 2-Amino-N-methoxy-N-methyl-4-trifluoromethyl-benzamide (482 mg, 1.94 mmol) was reacted with acetaldehyde (0.12 ml, 2.14 mmol) and sodium acetoxyborohydride (892 mg, 4.20 mmol) in CH$_2$Cl$_2$ at room temperature as described above to yield title compound (95 mg, 17%).

$^1$H NMR (300 MHz, CDCl$_3$): δ 7.44 (d, 1H, J=8.1 Hz), 6.86 (s, 1H), 6.84 (d, 1H, J=7.8 Hz), 3.57 (s, 3H), 3.35 (s, 3H), 3.18 (q, 2H, J=6.9 Hz), 1.28 (t, 3H, J=7.2 Hz).

Step 4: Synthesis of 2-ethylamino-4-trifluoromethyl-benzaldehyde

2-Ethylamino-N-methoxy-N-methyl-4-trifluoromethyl-benzamide (95 mg, 0.343 mmol) was reacted with LAH in THF at −40° C. for 1.5 hrs as described above to yield title compound (22 mg, 29%) after column chromatography (hexane/ethylacetate=20/1).

$^1$H NMR (300 MHz, CDCl$_3$): δ 9.88 (s, 1H), 8.35 (br, 1H), 7.57 (d, 1H, J=7.8 Hz), 6.88 (s, 1H), 6.87 (d, 1H, J=7.8 Hz), 3.30 (q, 2H, J=6.9 Hz), 1.35 (t, 3H, J=7.2 Hz).

Step 5: Synthesis of 3-(2-ethylamino-4-trifluoromethyl-phenyl)-acrylic acid

2-Ethylamino-4-trifluoromethyl-benzaldehyde (22 mg) was reacted with methyl (triphenylphosphoranylidene)acetate (49 mg, 0.14 mmol) at 110° C. overnight as described above to yield 3-(2-ethylamino-4-trifluoromethyl-phenyl)-acrylic acid methyl ester. 3-(2-Ethylamino-4-trifluoromethyl-phenyl)-acrylic acid methyl ester was reacted with 1N LiOH (5 ml) as described above to yield the title compound (20.2 mg)

$^1$H NMR (300 MHz, CDCl$_3$): δ 7.87 (d, 1H, J=15.6 Hz), 7.45 (d, 1H, J=8.1 Hz), 6.94 (d, 1H, J=7.8 Hz), 6.86 (s, 1H), 6.39 (d, 1H, J=15.6 Hz), 3.27 (q, 2H, J=7.2 Hz), 1.35 (t, 3H, J=7.2 Hz).

Step 6: Synthesis of (R)—N-[1-(3,5-difluoro-4-methanesulfonylamino-phenyl)-ethyl]-3-(2-ethylamino-4-trifluoromethyl-phenyl)-acrylamide (R)—N-(4-Aminoethyl-2,6-difluoro-phenyl)-methanesulfonamide, HCl salt (31 mg, 0.108 mmol) was reacted with 3-(2-ethylamino-4-trifluoromethyl-phenyl)-acrylic acid (20 mg, 0.078 mmol), NMM (0.1 ml) and DMTMM (27 mg) to give the title compound (11 mg, 29%).

$^1$H NMR (300 MHz, CDCl$_3$): δ 7.79 (d, 1H, J=15 Hz), 7.37 (d, 1H, J=7.8 Hz), 6.96 (d, 1H, J=8.1 Hz), 6.62 (s, 1H), 6.48 (br, 1H), 6.33 (d, 1H, J=15.3 Hz), 5.52 (d, 1H), 5.18 (t, 1H), 3.16 (s, 3H), 3.14 (t, 2H, J=7.2 Hz), 1.70 (m, 3H), 1.35 (t, 3H, J=7.5 Hz)

ESI [M−H]$^-$: 490

EXAMPLE 11

N-(3-Fluoro-4-methanesulfonylamino-5-methyl-benzyl)-3-(2-propylamino-4-trifluoromethyl-phenyl)-acrylamide

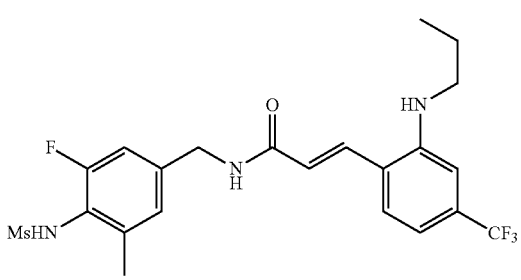

N-(4-Aminomethyl-2-fluoro-6-methyl-phenyl)-methanesulfonamide, HCl salt (25 mg) was reacted with 3-(2-propylamino-4-trifluoromethyl-phenyl)-acrylic acid (24 mg, 0.086 mmol), NMM (0.1 ml) and DMTMM (27 mg) at room temperature overnight to yield the title compound (21 mg, 50%).

$^1$H NMR (300 MHz, CDCl$_3$): δ 7.80 (d, 1H, J=15.3 Hz), 7.36 (d, 1H, J=8.1 Hz), 7.14 (m, 1H), 7.11 (m, 1H), 6.88 (m, 1H), 6.80 (d, 1H, J=15.3 Hz), 6.15 (t, 1H), 4.56 (d, 2H, J=6.0 Hz), 3.13 (t, 2H, J=7.2 Hz), 3.02 (s, 3H), 2.24 (s, 3H), 1.70 (m, 2H), 0.96 (t, 3H, J=7.5 Hz)

ESI [M−H]$^-$: 486

EXAMPLE 12

N-(3-Fluoro-4-methanesulfonylamino-5-vinyl-benzyl)-3-(2-propylamino-4-trifluoromethyl-phenyl)-acrylamide

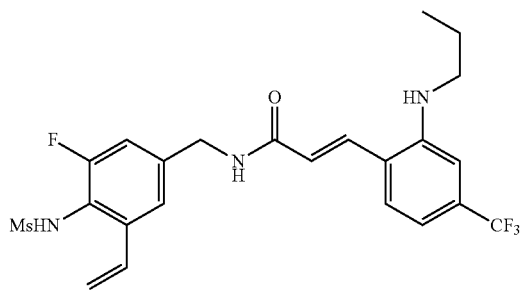

N-(4-Aminomethyl-2-fluoro-6-vinyl-phenyl)-methanesulfonamide, HCl salt (36 mg, 0.15 mmol) was reacted with 3-(2-propylamino-4-trifluoromethyl-phenyl)-acrylic acid (28 mg, 0.10 mmol), NMM (0.1 ml) and DMTMM (35 mg) at room temperature overnight to yield the title compound (17 mg, 34%) after column chromatography.

$^1$H NMR (300 MHz, CDCl$_3$): δ 7.80 (d, 1H, J=15.3 Hz), 7.38 (m, 1H), 7.22 (m, 1H), 7.15 (m, 1H), 7.11 (m, 1H), 6.90 (d, 1H, J=7.2 Hz), 6.83 (s, 1H), 6.34 (d, 1H, J=15.0 Hz), 5.95 (br, 2H), 5.81 (d, 1H, J=17.4 Hz), 5.46 (d, 1H, J=10.8 Hz), 4.58 (d, 2H, J=6.0 Hz), 3.16 (t, 2H, J=6.0 Hz), 3.08 (s, 3H), 1.69 (m, 2H), 1.03 (t, 3H, J=7.5 Hz)

ESI [M−H]$^-$: 498

EXAMPLE 13

N-(3-Cyano-5-fluoro-4-methanesulfonylamino-benzyl)-3-(2-propylamino-4-trifluoromethyl-phenyl)-acrylamide

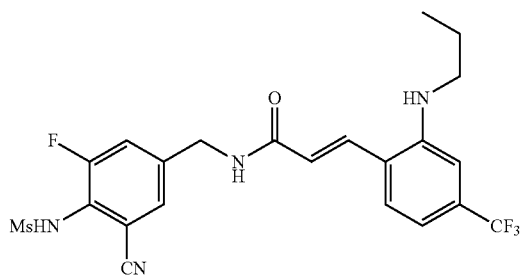

N-(4-Aminomethyl-2-fluoro-6-cyano-phenyl)-methanesulfonamide, HCl salt (26 mg, 0.092 mmol) was reacted with 3-(2-propylamino-4-trifluoromethyl-phenyl)-acrylic acid (20 mg, 0.073 mmol), NMM (0.1 ml) and DMTMM (28 mg) at room temperature overnight to yield the title compound (8 mg, 22%) after column chromatography.

$^1$H NMR (300 MHz, CDCl$_3$): δ 7.82 (d, 1H, J=4.7 Hz), 7.45 (m, 1H), 7.40 (m, 1H), 7.37 (m, 1H), 7.21 (s, 1H), 7.11

(m, 1H), 6.90 (d, 1H, J=7.8 Hz), 6.84 (s, 1H), 6.36 (d, 1H, J=15.0 Hz), 6.10 (br, 1H), 4.58 (d, 2H, J=6.3 Hz), 3.32 (s, 3H), 3.16 (t, 2H, J=6.0 Hz), 1.69 (m, 2H), 1.03 (t, 3H, J=7.5 Hz)
ESI [M−H]⁻: 497

EXAMPLE 14

N-(3-Ethynyl-5-fluoro-4-methanesulfonylamino-benzyl)-3-(2-propoxy-4-trifluoromethyl-phenyl)-acrylamide

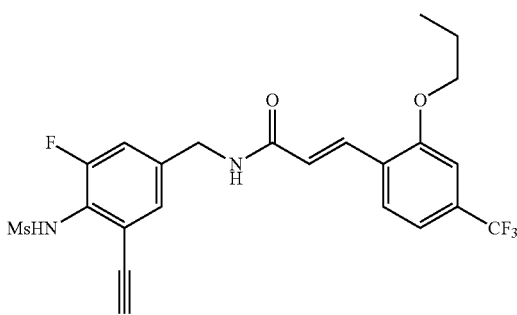

N-(4-Aminomethyl-2-ethynyl-6-fluoro-phenyl)-methanesulfonamide, HCl salt (53 mg, 0.19 mmol) was reacted with 3-(2-propoxy-4-trifluoromethyl-phenyl)-acrylic acid (49 mg, 0.18 mmol), NMM (0.1 ml) and DMTMM (60 mg) at room temperature overnight to yield the title compound (63 mg, 70%) after column chromatography (Hex/EtOAc=1/1).

¹H NMR (300 MHz, CDCl₃): δ 7.96 (d, 1H, J=15.6 Hz), 7.56 (d, 1H, J=7.8 Hz), 7.30 (s, 1H), 7.20 (m 1H), 7.11 (d, 1H, J=7.5 Hz), 6.97 (s, 1H), 6.61 (d, 1H, J=15.9 Hz), 6.41 (br, 1H), 6.03 (br, 1H), 4.54 (d, 1H, J=6.3 Hz), 4.03 (t, 2H, J=6.6 Hz), 3.48 (s, 1H), 3.26 (s, 3H), 1.85 (m, 2H), 1.06 (t, 3H, J=7.5 Hz)

EXAMPLE 15

3-(2-Ethoxy-4-trifluoromethyl-phenyl)-N-(3-fluoro-4-methanesulfonylamino-5-trifluoromethyl-benzyl)-acrylamide

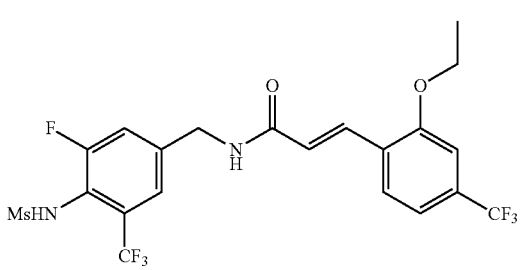

N-(4-Aminomethyl-2-fluoro-6-trifluoromethyl-phenyl)-methanesulfonamide, HCl salt (61 mg, 0.19 mmol) was reacted with 3-(2-ethoxy-4-trifluoromethyl-phenyl)-acrylic acid (45 mg, 0.17 mmol), NMM (0.1 ml) and DMTMM (64 mg, 0.22 mmol) at room temperature to yield the title compound (63 mg, 0.12 mmol, 69%) after column chromatography (Hex/EtOAc=1/1).

¹H NMR (300 MHz, CDCl₃): δ 7.95 (d, 1H, J=15.6 Hz), 7.56 (d, 1H, J=7.5 Hz), 7.40 (m, 1H), 7.19 (d, 1H, J=8.1 Hz), 7.10 (s, 1H), 6.63 (d, 1H, J=15.6 Hz), 6.22 (br, 1H), 4.60 (d, 2H, J=6.0 Hz), 4.12 (q, 2H, J=7.2 Hz), 3.28 (s, 3H), 1.50 (t, 3H, J=7.2 Hz).

EXAMPLE 16

(R)-3-(2,6-Dibutyl-4-trifluoromethyl-phenyl)-N-[1-(3,5-difluoro-4-methanesulfonylamino-phenyl)-ethyl]-acrylamide

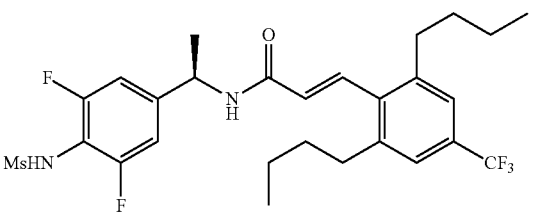

(R)—N-[4-(1-Amino-ethyl)-2,6-difluoro-phenyl]-methanesulfonamide, HCl salt (43 mg, 0.15 mmol) was reacted with 3-(2,6-dibutyl-4-trifluoromethyl-phenyl)-acrylic acid (50 mg, 0.15 mmol) to give the title compound (30 mg, 35%) after purification by crystallization from Hex/EtOAc.

¹H NMR (300 MHz, CDCl₃): δ 7.80 (d, 1H, J=15.9 Hz), 7.29 (s, 1H), 7.26 (s, 2H), 7.05 (m, 2H), 6.02 (s, 1H), 5.95 (d, 1H, J=15.9 Hz), 5.74 (s, 1H), 5.34 (s, 1H), 5.21 (m, 1H), 3.22 (s, 3H), 2.63 (m, 4H), 1.32 (m, 11H), 0.91 (m, 6H).
ESI [M+H]+:

EXAMPLE 17

(R)-3-(2,6-Diethyl-4-trifluoromethyl-phenyl)-N-[1-(3,5-difluoro-4-methanesulfonylamino-phenyl)-ethyl]-acrylamide)

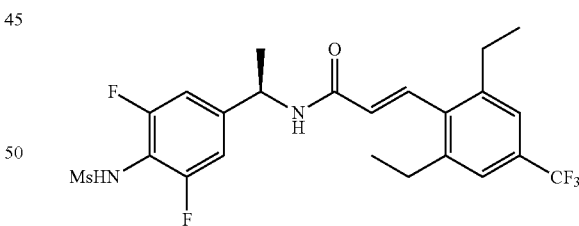

(R)—N-[4-(1-Amino-ethyl)-2,6-difluoro-phenyl]-methanesulfonamide, HCl salt (38 mg, 0.13 mmol) was reacted with 3-(2,6-diethyl-4-trifluoromethyl-phenyl)-acrylic acid (36 mg, 0.13 mmol) to give the title compound (20 mg, 30%) after purification by crystallization from Hex/EtOAc.

¹H NMR (300 MHz, CDCl₃): δ 7.84 (d, 1H, J=16.5 Hz), 7.29 (s, 1H), 7.30 (s, 2H), 7.01 (m, 2H), 6.06 (s, 1H), 6.02 (d, 1H, J=16.2 Hz), 5.72 (s, 1H), 5.30 (m, 1H), 5.24 (m, 1H), 3.19 (s, 3H), 2.69 (m, 4H), 1.24 (m, 9H).
ESI [M−H]⁻: 503

EXAMPLE 18

N-(3,5-Difluoro-4-methanesulfonylamino-benzyl)-3-(2-ethylamino-4-trifluoromethyl-phenyl)-acrylamide

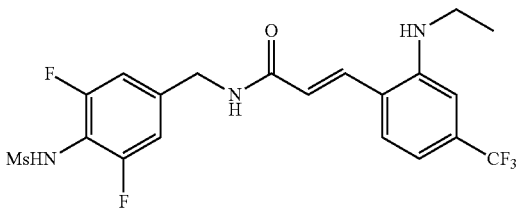

N-(4-Aminomethyl-3,5-difluoro-phenyl)-methanesulfonamide, HCl salt (42 mg, 0.154 mmol) was reacted with 3-(2-ethylamino-4-trifluoromethyl-phenyl)-acrylic acid (40 mg, 0.154 mmol) to give the title compound (36 mg, 49%) after purification by crystallization from Hex/EtOAc.

$^1$H NMR (300 MHz, CDCl$_3$): δ 7.80 (d, 1H, J=15 Hz), 7.38 (m, 2H), 6.95 (m, 2H), 6.84 (s, 1H), 6.35 (d, 1H, J=15.6 Hz), 5.99 (s, 1H), 4.55 (d, 2H, J=6 Hz), 3.26 (m, 2H), 3.22 (s, 3H), 1.33 (m, 3H).

ESI [M–H]$^-$: 476

EXAMPLE 19

3-(2-Ethylamino-4-trifluoromethyl-phenyl)-N-(3-fluoro-4-methanesulfonylamino-5-methyl-benzyl)-acrylamide

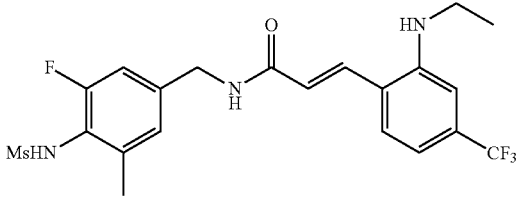

N-(4-aminomethyl-3-fluoro-5-methyl-phenyl)-methanesulfonamide, HCl salt (28 mg, 0.104 mmol) was reacted with 3-(2-ethylamino-4-trifluoromethyl-phenyl)-acrylic acid (27 mg, 0.104 mmol) to give the title compound (29 mg, 59%) after purification by crystallization from Hex/EtOAc.

$^1$H NMR (300 MHz, DMSO-d6): δ 8.59 (bs, 1H), 7.67 (d, 1H, J=15.6 Hz), 7.47 (m, 2H), 6.88 (m, 1H), 6.57 (d, 1H, J=15.6 Hz), 6.04 (s, 1H), 4.40 (d, 2H, J=5.4 Hz), 3.15 (m, 2H), 2.96 (s, 3H), 2.20 (s, 3H), 1.18 (m, 3H).

ESI [M+H]+

EXAMPLE 20

N-(3,5-Difluoro-4-methanesulfonylamino-benzyl)-3-(2-isopropoxy-4-trifluoromethyl-phenyl)-acrylamide

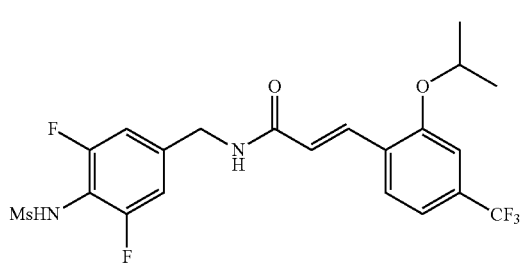

N-(4-Aminomethyl-3,5-difluoro-phenyl)-methanesulfonamide, HCl salt (14 mg, 0.051 mmol) was reacted with 3-(2-isopropoxy-4-trifluoromethyl-phenyl)-acrylic acid (14 mg, 0.051 mmol) to give the title compound (11 mg, 40%) after purification by crystallization from Hex/EtOAc.

$^1$H NMR (300 MHz, DMSO-d6): δ 9.50 (s, 1H), 8.70 (d, 1H, J=7.8 Hz), 7.69 (m, 2H), 7.24 (m, 4H), 6.78 (d, 1H, J=15.9 Hz), 4.85 (m, 1H), 4.52 (d, 2H, J=6.0 Hz), 3.02 (s, 3H), 1.31 (m, 6H).

ESI [M–H]$^-$: 491

EXAMPLE 21

N-[1-(3,5-Difluoro-4-methanesulfonylamino-phenyl)-ethyl]-3-(2-propyl-4-trifluoromethyl-phenyl)-acrylamide

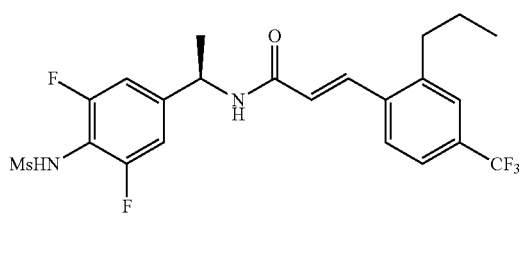

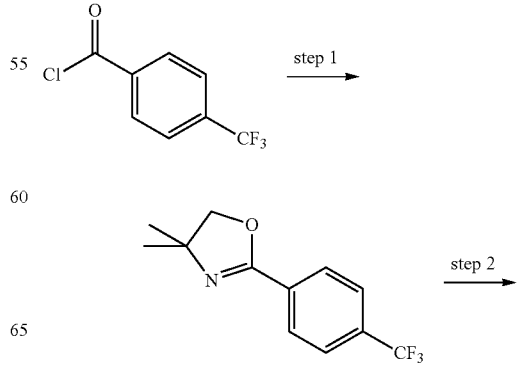

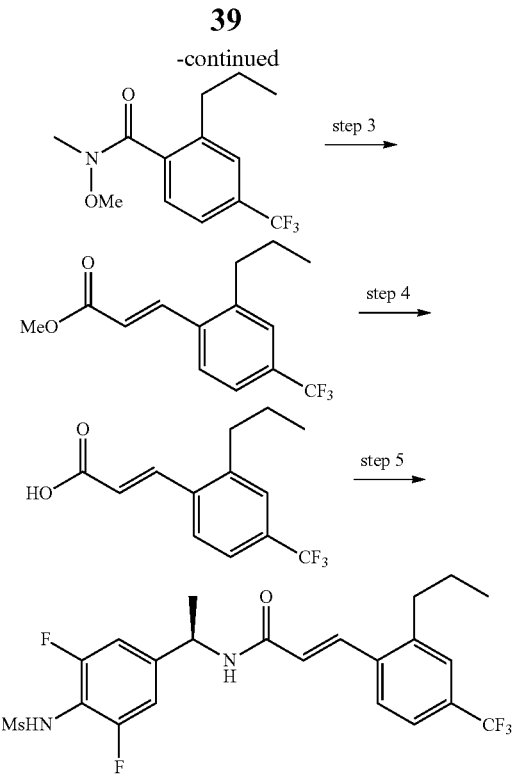

Step 1: Synthesis of 4,4-dimethyl-2-(4-trifluoromethyl-phenyl)-4,5-dihydro-oxazole To an ice-cold solution of 2-amino-2-methyl-1-propanol (21.4 g, 240 mmol) and triethylamine (16.8 mL, 120 mmol) in THF was added dropwise 4-trifluoromethyl benzyl chloride (25.0 g, 120 mmol). After the addition, the reaction mixture was stirred at 0° C. for 30 mins and then stirred at ambient temperature for 8 hrs. The precipitate was removed by filtration and the filtrate was concentrated by evaporating the solvent under reduced pressure. The resulting residue was treated dropwise with thionyl chloride with vigorous stirring at 0° C. After complete addition, the reaction mixture was further stirred at ambient temperature for 1 hr. Ether was poured into the reaction mixture and the precipitate was collected by filtration. The precipitate was dissolved in water and the aqueous solution was hydrolyzed with 10% (w/v) NaOH. The aqueous phase was extracted three times with ether, and the combined organic layer was washed with brine, dried over anhydrous MgSO$_4$, and concentrated under reduced pressure. The crude residue was purified by column chromatography (Hex/EtOAc=5/1) to yield the title compound (25.4 g, 87%).

$^1$H NMR (300 MHz, CDCl$_3$): δ 8.05 (d, 2H, J=7.8 Hz), 7.66 (d, 2H, J=7.8 Hz), 4.14 (s, 2H), 1.39 (s, 6H).

Step 2: Synthesis of N-methoxy-N-methyl-2-propyl-4-trifluoromethyl-benzamide

A solution of 4,4-dimethyl-2-(4-trifluoromethyl-phenyl)-4,5-dihydro-oxazole (2.43 g, 10.0 mmol) in THF was cooled to −78° C. under argon, and n-BuLi (2.5M in hexane, 4.0 mL, 10.0 mmol) was added dropwise to the solution. The resulting dark brown solution was stirred for 2 hrs at −60° C. and then cooled again to −78° C., to which was added propyl iodide (1.88 mL, 19.0 mmol). The reaction mixture was allowed to warm up to room temperature, and then stirred overnight. The reaction was quenched by adding water and the aqueous phase was extracted three times with EtOAc. The combined organic layer was washed with brine, dried over anhydrous MgSO$_4$, and concentrated under reduced pressure to give dark brown residue.

A mixture of the crude residue obtained above and 6N HCl (5.0 mL) was heated at reflux for 8 hrs. After cooling to ambient temperature, water was added to the reaction mixture and the aqueous layer was extracted three times with EtOAc. The combined organic layer was washed with water, brine, dried over anhydrous MgSO$_4$, and concentrated under reduced pressure. The resulting residue dissolved in THF was treated with 1N LiOH, and the resulting mixture was stirred 18 hrs at ambient temperature and then 18 hrs at 70° C. After cooling, the reaction mixture was acidified with 2N HCl and then extracted three times with chloroform. The combined organic layer was washed with brine, dried over anhydrous MgSO$_4$, and concentrated under reduced pressure to give crude benzoic acid product.

The resulting crude acid was dissolved in dichloromethane, to which were added successively N,O-dimethylhydroxylamine, HCl (630 mg, 6.46 mmol), NMM (0.71 mL, 6.46 mmol), and EDC (990 mg, 7.75 mmol). The resulting mixture was stirred overnight at ambient temperature and then quenched by adding water. The aqueous layer was extracted three times with EtOAc, and the combined organic layer was washed with brine, dried over anhydrous MgSO$_4$, and concentrated under reduced pressure. The crude residue was purified by column chromatography (Hex/EtOAc=2/1) to yield the title compound (230 mg, 8%).

$^1$H NMR (300 MHz, CDCl$_3$): δ 7.50 (s, 1H), 7.48 (d, 1H, J=7.8 Hz), 7.36 (d, 1H, J=7.8 Hz), 3.43 (bs, 3H), 3.36 (bs, 3H), 2.65 (t, 2H, J=7.8 Hz), 1.67 (m, 2H), 0.97 (t, 3H, J=7.2 Hz).

Step 3: Synthesis of 3-(2-propyl-4-trifluoromethyl-phenyl)-acrylic acid methyl ester To a solution of N-methoxy-N-methyl-2-propyl-4-trifluoromethyl-benzamide (230 mg, 0.84 mmol) in THF (15 mL) was added dropwise 1.0M LiAlH$_4$ (0.42 mL, 0.42 mmol) at −78° C. The mixture was warmed up to −20° C. and stirred for 30 mins. An aqueous solution of sodium potassium tartrate (10% w/v) was added to the reaction mixture and the resulting mixture was vigorously stirred for 30 mins, to which was added Et$_2$O. After separation of two phases, the aqueous layer was extracted three times with ether and the combined organic layer was washed with brine, dried over anhydrous MgSO$_4$, filtered and concentrated under reduced pressure. The product was vacuum dried to yield the 2-propyl-4-trifluoromethyl-benzaldehyde.

To a solution of the aldehyde obtained above in toluene was added methyl (triphenylphosphoranylidene)acetate (285 mg, 0.85 mmol), and the resulting mixture was heated at 80° C. for 3 hrs. The reaction mixture was diluted with EtOAc, and washed with water and brine. The organic layer was dried over anhydrous MgSO$_4$ and concentrated under reduced pressure. The resulting residue was purified by column chromatography (Hex/EtOAc=4/1) to give the title compound (220 mg, 96%).

$^1$H NMR (300 MHz, CDCl$_3$): δ 7.98 (d, 1H, J=15.9 Hz), 7.63 (d, 1H, J=8.4 Hz), 7.46 (d, 1H, J=8.4 Hz), 7.45 (s, 1H), 6.42 (d, 1H, J=15.9 Hz), 3.83 (s, 3H), 2.77 (t, 2H, J=7.5 Hz), 1.63 (m, 2H), 0.98 (t, 3H, J=7.5 Hz).

Step 4: Synthesis of 3-(2-propyl-4-trifluoromethyl-phenyl)-acrylic acid

To a suspension of 3-(2-propyl-4-trifluoromethyl-phenyl)-acrylic acid methyl ester (220 mg, 0.81 mmol) in THF (3 mL)

was added a solution of 1N-LiOH (6 ml), and the mixture was stirred for 3 hours at room temperature. The reaction mixture was diluted with H₂O, which was washed three times with EtOAc, acidified with 1N HCl to pH 1-2. The resulting solution was extracted three times with methylene chloride and then dried over anhydrous MgSO₄ and concentrated in vacuo to give the title compound (155 mg, 74%).

¹H NMR (300 MHz, CDCl₃): δ 8.09 (d, 1H, J=15.9 Hz), 7.67 (d, 1H, J=7.8 Hz), 7.49 (d, 1H, J=7.8 Hz), 7.47 (s, 1H), 6.44 (d, 1H, J=15.9 Hz), 2.79 (t, 2H, J=7.5 Hz), 1.64 (m, 2H), 0.99 (t, 3H, J=7.5 Hz).

Step 5: Synthesis of (R)—N-[1-(3,5-difluoro-4-methanesulfonylamino-phenyl)-ethyl]-3-(2-propyl-4-trifluoromethyl-phenyl)-acrylamide To a suspension of (R)—N-[4-(1-amino-ethyl)-2,6-difluoro-phenyl]-methanesulfonamide, HCl salt (67 mg, 0.23 mmol) in THF (5 mL) was added N-methylmorpholine (51 μl, 0.46 mmol). The mixture was stirred for 5 minutes, to which were added 3-(2-propyl-4-trifluoromethyl-phenyl)-acrylic acid (60 mg, 0.23 mmol) and 4-(4,6-dimethoxy[1,3,5]triazin-2-yl)-4-methylmorpholinium chloride hydrate (DMTMM, 76 mg, 0.28 mmol). The mixture was stirred overnight at room temperature and was concentrated under reduced pressure. The residue was diluted with EtOAc and water. The organic layer was washed with saturated sodium bicarbonate, 1N HCl and brine, dried over anhydrous magnesium sulfate, filtered, and concentrated under reduced pressure. The crude residue was purified by recrystallization from n-Hex/EtOAc to give title compound (83 mg, 74%).

¹H NMR (300 MHz, CD₃OD): δ 7.99 (d, 1H, J=15.6 Hz), 7.86 (d, 1H, J=8.7 Hz), 7.60 (bs, 2H), 7.18 (d, 2H, J=8.7 Hz), 6.75 (d, 1H, J=15.6 Hz), 5.20 (m, 1H), 3.17 (s, 3H), 2.90 (t, 2H, J=7.8 Hz), 1.70 (m, 2 H), 1.61 (d, 3H, J=7.2 Hz), 1.06 (t, 3H, J=7.2 Hz).

ESI [M−H]⁻: 489

EXAMPLE 22

N-(3,5-Difluoro-4-methanesulfonylamino-benzyl)-3-(2-propyl-4-trifluoromethyl-phenyl)-acrylamide

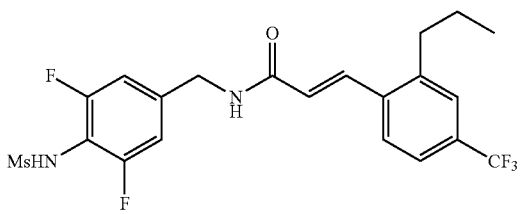

N-(4-Aminomethyl-2,5-difluoro-phenyl)-methanesulfonamide, HCl salt (33 mg, 0.12 mmol) was reacted with 3-(2-propyl-4-trifluoromethyl-phenyl)-acrylic acid (25 mg, 0.097 mmol) to give the title compound (30 mg, 65%) after purification by column chromatography (gradient 12% to 100% EtOAc in Hex).

¹H NMR (300 MHz, CD₃OD): δ 8.05 (d, 1H, J=15.6 Hz), 7.87 (d, 1H, J=8.7 Hz), 7.62 (bs, 2H), 7.16 (d, 2H, J=8.7 Hz), 6.76 (d, 1H, J=15.6 Hz), 4.61 (s, 2H), 3.18 (s, 3H), 2.93 (t, 2H, J=7.8 Hz), 1.71 (m, 2 H), 1.09 (t, 3H, J=7.5 Hz).

ESI [M+H]⁺:

EXAMPLE 23

N-(3-Fluoro-4-methanesulfonylamino-5-methyl-benzyl)-3-(2-propyl-4-trifluoromethyl-phenyl)-acrylamide

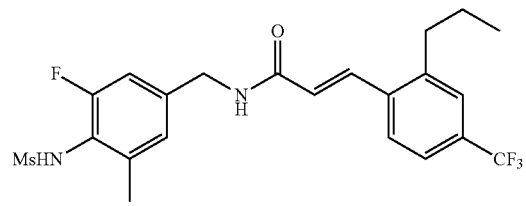

N-(4-Aminomethyl-2-fluoro-6-methyl-phenyl)-methanesulfonamide, HCl salt (32 mg, 0.12 mmol) was reacted with 3-(2-propyl-4-trifluoromethyl-phenyl)-acrylic acid (25 mg, 0.097 mmol) to give the title compound (30 mg, 63%) after purification by column chromatography (gradient 12% to 100% EtOAc in Hex).

¹H NMR (300 MHz, CD₃OD): δ 8.05 (d, 1H, J=15.6 Hz), 7.85 (d, 1H, J=8.1 Hz), 7.60 (m, 2H), 7.30 (m, 2H), 6.74 (d, 1H, J=15.6 Hz), 4.64 (s, 2H), 3.08 (s, 3H), 2.92 (t, 2H, J=7.5 Hz), 2.38 (d, 3H, J=2.1 Hz), 1.72 (m, 2 H), 1.08 (t, 3H, J=7.5 Hz).

ESI [M+H]⁺:

EXAMPLE 24

(R)-3-(2-Butyl-4-trifluoromethyl-phenyl)-N-[1-(3,5-difluoro-4-methanesulfonylamino-phenyl)-ethyl]-acrylamide

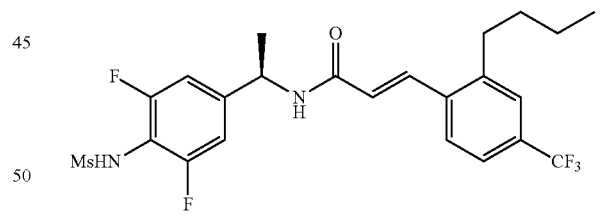

3-(2-Butyl-4-trifluoromethyl-phenyl)-acrylic acid was obtained by the procedure in example 21.

(R)—N-[4-(1-Amino-ethyl)-2,6-difluoro-phenyl]-methanesulfonamide, HCl salt (38 mg, 0.13 mmol) was reacted with 3-(2-butyl-4-trifluoromethyl-phenyl)-acrylic acid (30 mg, 0.11 mmol) to give the title compound (29 mg, 43%) after purification by column chromatography (gradient 12% to 100% EtOAc in Hex).

¹H NMR (300 MHz, CD₃OD): δ 7.90 (d, 1H, J=15.6 Hz), 7.76 (d, 1H, J=8.7 Hz), 7.51 (bs, 2H), 7.08 (d, 2H, J=8.7 Hz), 6.65 (d, 1H, J=15.6 Hz), 5.10 (m, 1H), 3.07 (s, 3H), 2.82 (t, 2H, J=7.8 Hz), 1.55 (m, 2H), 1.51 (d, 3H, J=7.2 Hz), 1.40 (m, 2 H), 0.94 (t, 3H, J=7.2 Hz).

ESI [M−H]⁻: 503

EXAMPLE 25

(R)—N-[1-(3,5-Difluoro-4-methanesulfonylamino-phenyl)-propyl]-3-(2-propyl-4-trifluoromethyl-phenyl)-acrylamide

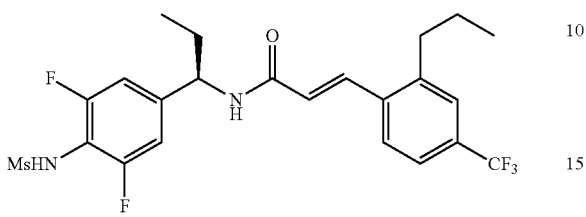

(R)—N-[4-(1-Amino-propyl)-2,6-difluoro-phenyl]-methanesulfonamide, HCl salt (15 mg, 0.050 mmol) was reacted with 3-(2-propyl-4-trifluoromethyl-phenyl)-acrylic acid (8 mg, 0.03 μmol) to give the title compound (15 mg, 97%) after purification by column chromatography (gradient 12% to 100% EtOAc in Hex).

$^1$H NMR (300 MHz, DMSO-d6): δ 8.65 (d, 1H, J=8.1 Hz), 7.69 (m, 4H), 7.11 (d, 2H, J=8.4 Hz), 6.75 (d, 1H, J=15.6 Hz), 4.82 (m, 1H), 2.98 (s, 3H), 2.75 (t, 2H, J=7.8 Hz), 1.71 (m, 2 H), 1.52 (m, 2 H), 1.23 (m, 2 H), 0.89 (m, 6H).

ESI [M+H]$^+$:

EXAMPLE 26

(R)—N-[1-(3,5-Difluoro-4-methanesulfonylamino-phenyl)-ethyl]-3-(2-isopropoxy-4-trifluoromethyl-phenyl)-acrylamide

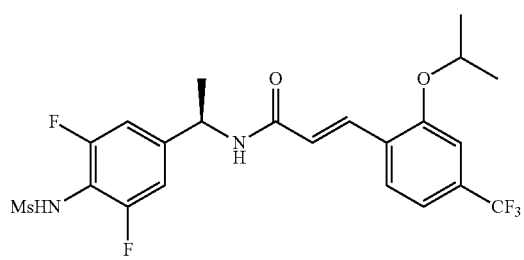

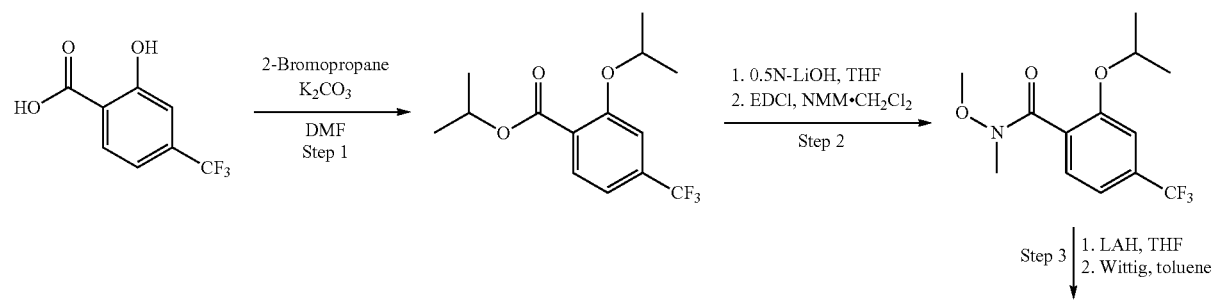

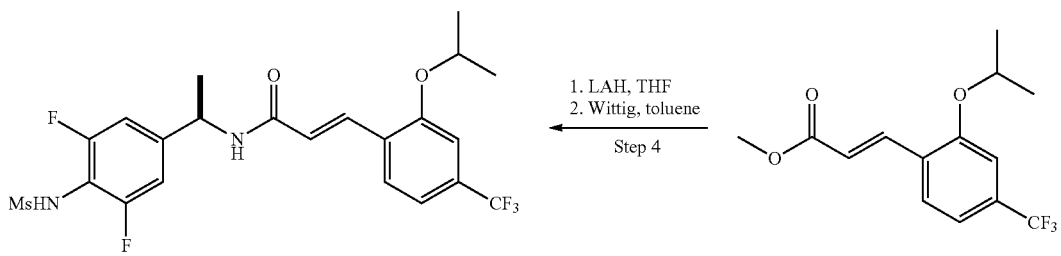

Step 1: Synthesis of 2-isopropoxy-4-trifluoromethyl-benzoic acid isopropyl ester A mixture of 2-hydroxy-4-trifluoromethyl-benzoic acid (500 mg, 2.42 mmol) in DMF (5 mL) was added potassium carbonate (837 mg, 6.06 mmol) and 2-bromopropane (906 mg, 5.33 mmol). The resulting mixture was stirred for 48 hours at 110° C. The reaction mixture was diluted with EtOAc, which was washed with 1N HCl, water, and brine, dried over anhydrous magnesium sulfate, filtered and concentrated under reduced pressure. The crude residue was purified by chromatography (Hex/EtOAc=5/1) to give the title compound (200 mg, 28%).

$^1$H NMR (300 MHz, CDCl$_3$): δ 7.73 (d, 1H, J=8.1 Hz), 7.19 (d, 1H, J=8.4 Hz), 7.15 (s, 1H), 5.31-5.29 (m, 1H), 4.68-4.60 (m, 1H), 1.40 (d, 6H, J=6.9 Hz), 1.36 (d, 6H, J=6.6 Hz).

Step 2: Synthesis of 2-isopropoxy-N-methoxy-N-methyl-4-trifluoromethyl-benzamide To a suspension of 2-isopropoxy-4-trifluoromethyl-benzoic acid isopropyl ester (35 mg, 0.12 mmol) in THF (1 ml) was added a solution of 0.5 N-LiOH (2 eq), and the resulting mixture was stirred for 2 hours at room temperature. The reaction mixture was acidified with 1N HCl, and then extracted with EtOAc. The combined organic layer was washed with water and brine, dried over anhydrous magnesium sulfate, filtered and concentrated under reduced pressure. The resulting residue was vacuum dried to yield the 2-isopropoxy-4-trifluoromethyl-benzoic acid. To an ice-cold suspension of 2-isopropoxy-4-trifluoromethyl-benzoic acid and N,O-dimethylhydroxylamine hydrochloride (13 mg, 0.132 mmol) in CH$_2$Cl$_2$ (1 mL) was added N-methylmorpholine (0.015 ml, 0.132 mmol), and the resulting mixture was stirred for 5 minutes, to which were added N-(3-dimethylaminopropyl)-N'-ethylcarbodiimide hydrochloride (26 mg, 0.132 mmol). The resulting mixture was stirred for 2 hours at room temperature, and then diluted with EtOAc. The organic layer was washed with 1N HCl, water, and brine, dried over anhydrous magnesium sulfate, filtered and concentrated under reduced pressure. The crude residue was purified by chromatography (Hex/EtOAc=3/1) to give the title compound (28 mg, 80%).

$^1$H NMR (300 MHz, CDCl$_3$): δ 7.26-7.18 (m, 2H), 7.11 (s, 1H), 4.66-4.60 (m, 1H), 3.46 (s, 3H), 3.35 (s, 3H), 1.34 (d, 6H, J=6.0 Hz).

Step 3: Synthesis of 3-(2-isopropoxy-4-trifluoromethyl-phenyl)-acrylic acid methyl ester To a suspension of 2-isopropoxy-N-methoxy-N-methyl-4-trifluoromethyl-benzamide (28 mg, 0.096 mmol) in THF (1.5 mL) was added dropwise 1.0M LiAlH$_4$ (0.048 ml, 0.5 eq) at −60° C. The mixture was slowly warmed up to −20° C. until the reaction was completed. The reaction was slowly quenched with sat'd KHSO$_4$ (1 mL) and then diluted with water (1 mL). The reaction mixture was extracted with ether and the combined organic layer was dried over anhydrous MgSO$_4$, filtered and concentrated under reduced pressure. The resulting compound was vacuum dried to yield the 2-isopropoxy-4-trifluoromethyl-benzaldehyde. To the aldehyde prepared above was added toluene (1 mL) followed by portionwise addition of methyl (triphenylphosphoranylidene)acetate (32 mg, 0.105 mmol) (exothermic). Toluene (1 mL) was added to the reaction mixture, and the resulting mixture was heated at 80° C. for 3 hours. The reaction mixture was cooled to room temperature, and then was directly loaded to a short silica-gel column and eluted with the solvent (Hex/EtOAc=20/1) to give the title compound (20 mg, 72%).

$^1$H NMR (300 MHz, CDCl$_3$): δ 7.96 (d, 1H, J=16.2 Hz), 7.58 (d, 1H, J=8.1 Hz), 7.17 (d, 1H, J=7.8 Hz), 7.11 (s, 1H), 6.57 (d, 1H, J=16.2 Hz), 4.71-4.63 (m, 1H), 3.81 (s, 3H), 1.41 (d, 6H, J=6.3 Hz).

Step 4: Synthesis of N-[1-(3,5-difluoro-4-methanesulfonylamino-phenyl)-ethyl]-3-(2-isopropoxy-4-trifluoromethyl-phenyl)-acrylamide

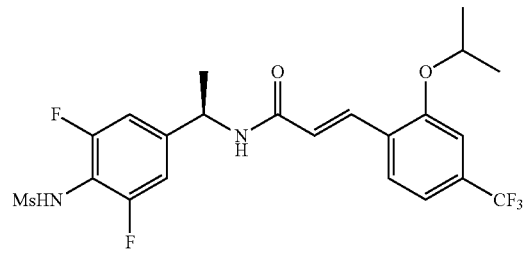

To a suspension of 3-(2-isopropoxy-4-trifluoromethyl-phenyl)-acrylic acid methyl ester (15 mg, 0.052 mmol) in THF (1 ml) was added a solution of 0.5 N-LiOH (0.2 ml), and the resulting mixture was stirred for 3 hours at room temperature. The reaction mixture was acidified with 1N HCl to pH 1~2. The mixture solution was extracted three times with methylene chloride, and the combined organic layer was dried over anhydrous Na$_2$SO$_4$ and concentrated in vacuo to give 3-(2-isopropoxy-4-trifluoromethyl-phenyl)-acrylic acid (14 mg, 98%). To a suspension of 3-(2-isopropoxy-4-trifluoromethyl-phenyl)-acrylic acid (14 mg, 0.051 mmol) and N-[4-(1-amino-ethyl)-2,6-difluoro-phenyl]-methanesulfonamide, HCl salt (17.2 mg, 0.060 mmol) in DMF (2 mL) was added N-methylmorpholine (0.007 ml, 0.060 mmol). The mixture was stirred for 5 minutes, to which were added N-(3-dimethylaminopropyl)-N'-ethylcarbodiimide hydrochloride (26 mg, 0.132 mmol). The mixture was stirred for 12 hours at room temperature, and then diluted with EtOAc (4 mL). The organic layer was washed with 1N HCl, water, and brine, dried over anhydrous magnesium sulfate, filtered and concentrated under reduced pressure. The crude residue was purified by chromatography (Hex/EtOAc=1/1) to give the title compound (24 mg, 79%).

$^1$H NMR (300 MHz, CDCl$_3$): δ 7.93 (d, 1H, J=15.6 Hz), 7.56 (d, 1H, J=7.8 Hz), 7.16 (d, 1H, J=8.1 Hz), 7.10 (s, 1H), 7.01 (d, 1H, J=8.4 Hz), 6.54 (d, 1H, J=15.6 Hz), 5.82 (d, 1H, J=6.9 Hz), 5.19 (t, 1H, J=6.9 Hz), 4.67-4.63 (m, 1H), 3.20 (s, 3H), 1.56 (d, 6H, J=6.3 Hz). 1.40 (d, 3H, J=5.4 Hz).

ESI [M−H]$^-$: 505

EXAMPLE 27

(R)—N-[1-(3,5-Difluoro-4-methanesulfonylamino-phenyl)-ethyl]-3-(4-fluoro-2-propoxy-phenyl)-acrylamide

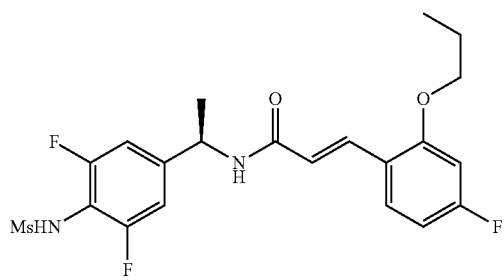

Step 1: Synthesis of 3-(4-fluoro-2-hydroxy-phenyl)-acrylic acid methyl ester 2-Hydroxy-4-fluoro-benzaldehyde (306 mg, 1.99 mmol) was reacted with methyl (triphenylphosphoranylidene)acetate (681 g, 2.044 mmol) at 110° C. overnight as described above to yield title compound (334 mg, 85%).

$^1$H NMR (300 MHz, CDCl$_3$): δ 7.93 (d, 1H, J=15.9 Hz), 7.45 (m, 1H), 6.65 (m, 1H), 6.59 (m, 1H), 6.56 (s, 1H), 6.53 (d, 1H, J=16.2 Hz), 5.27 (br, 1H), 3.82 (s, 3H).

Step 2: Synthesis of 3-(4-fluoro-2-propoxy-phenyl)-acrylic acid methyl ester 3-(4-Fluoro-2-hydroxy-phenyl)-acrylic acid methyl ester (110.5 mg) was reacted with K$_2$CO$_3$ (111 mg) and propane iodide (0.1 ml) at 80° C. overnight as described above to yield title compound (134 mg, 100%)

$^1$H NMR (300 MHz, CDCl$_3$): δ 7.90 (d, 1H, J=15.9 Hz), 7.45 (t, 1H, J=7.5 Hz), 6.65 (m, 1H), 6.59 (m, 1H), 6.49 (d, 1H, J=15.9 Hz), 3.96 (t, 2H, J=6.6 Hz), 3.78 (s, 3H), 1.89 (m, 2H), 1.07 (t, 3H, J=7.5 Hz).

Step 3: Synthesis of 3-(4-fluoro-2-propoxy-phenyl)-acrylic acid 3-(4-Fluoro-2-propoxy-phenyl)-acrylic acid methyl ester (134 mg, 0.563 mmol) was reacted with aqueous 1N LiOH (5 ml) as described above to yield title compound (117 mg, 92%).

$^1$H NMR (300 MHz, CDCl$_3$): δ 8.00 (d, 1H, J=16.5 Hz), 7.49 (t, 1H, J=8.4 Hz), 6.67 (m, 2H) 6.50 (d, 1H, J=15.9 Hz), 3.98 (t, 2H, J=6.6 Hz), 1.91 (m, 2H), 1.09 (t, 3H, J=7.2 Hz).

Step 4: Synthesis of (R)—N-[1-(3,5-Difluoro-4-methanesulfonylamino-phenyl)-ethyl]-3-(4-fluoro-2-propoxy-phenyl)-acrylamide (R)—N-(4-Aminoethyl-2,6-difluoro-phenyl)-methanesulfonamide, HCl salt (85 mg, 0.29 mmol) was reacted with 3-(4-fluoro-2-propoxy-phenyl)-acrylic acid (65 mg, 0.29 mmol), NMM (0.15 ml) and DMTMM (98 mg) at room temperature overnight to yield the title compound (77 mg, 58%) after column chromatography (Hex/EtOAc=1/1).

$^1$H NMR (300 MHz, CDCl$_3$): δ 7.84 (d, 1H, J=15.6 Hz), 7.43 (t, 1H, J=6.9 Hz), 6.98 (d, 1H, J=8.7 Hz), 6.63 (m, 2H), 6.47 (d, 1H, J=15.6 Hz), 5.87 (br, 1H), 5.18 (m, 1H), 4.11 (t, 2H, J=6.9 Hz), 3.19 (s, 3H), 1.87 (m, 2H), 1.09 (t, 3H, J=7.5 Hz)

EXAMPLE 28

N-(3,5-Difluoro-4-methanesulfonylamino-benzyl)-3-(4-fluoro-2-propoxy-phenyl)-acrylamide

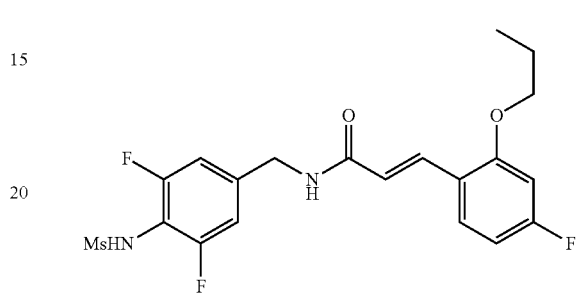

N-(4-Aminomethyl-2,6-difluoro-phenyl)-methanesulfonamide, HCl salt (66 mg, 0.24 mmol) was reacted with 3-(4-fluoro-2-propoxy-phenyl)-acrylic acid (51 mg, 0.23 mmol), NMM (0.15 ml) and DMTMM (78 mg) at room temperature overnight to yield the title compound (52 mg, 0.12 mmol, 53%) after column chromatography (Hex/EtOAc=1/1).

$^1$H NMR (300 MHz, CDCl$_3$): δ 7.90 (d, 1H, J=15.9 Hz), 7.44 (t, 1H, J=6.6 Hz), 6.99 (d, 1H, J=8.1 Hz), 6.65 (m, 2H), 6.52 (d, 1H, J=15.6 Hz), 5.89 (br, 1H), 4.55 (d, 2H, J=6.0 Hz), 3.98 (t, 2H, J=6.6 Hz), 3.21 (s, 3H), 1.90 (m, 2H), 1.08 (t, 3H, J=7.5 Hz).

EXAMPLE 29

(R)—N-[1-(3,5-Difluoro-4-methanesulfonylamino-phenyl)ethyl]-3-(4-fluoro-2-propylaminophenyl)-acrylamide

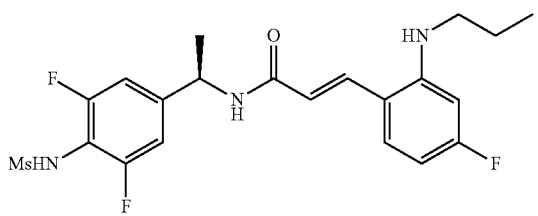

Step 1. Synthesis of N-methoxy-N-methyl-4-fluoro-2-nitro-benzamide

To a solution of 4-fluoro-2-nitrobenzoic acid (1 g, 5.4 mmol), N,O-dimethylhydroxylamine hydrochloride (0.58 g, 5.95 mmol) and N-methylmorpholine (0.65 mL, 5.91 mmol) in dichloromethane (20 mL) was added 1-ethyl-3-(3-dimethylaminopropyl)carbodiimide hydrochloride (1.14 g, 5.95 mmol). The mixture was stirred for 80 minutes at room temperature. The mixture was concentrated under reduced pressure and then diluted with EtOAc and water. The organic layer was washed with 3 N HCl, saturated aqueous NaHCO₃ solution and brine, dried over anhydrous magnesium sulfate, filtered, and concentrated under reduced pressure to give N-methoxy-N-methyl-4-fluoro-2-nitro-benzamide (1.15 g, 95%).

$^1$H NMR (300 MHz, CDCl₃): δ 7.89~7.85 (m, 1 H), 7.58~7.54 (m, 1 H), 7.47-7.41 (m, 1 H), 3.37 (s, 3 H), 3.36 (s, 3 H).

Step 2. Synthesis of N-methoxy-N-methyl-2-amino-4-fluoro-benzamide

A mixture of N-methoxy-N-methyl-4-fluoro-2-nitro-benzamide (1.15 g, 5.04 mmol) and 5% palladium charcoal (190 mg) in EtOH (30 mL) was shaken overnight under hydrogen atmosphere (3 atm). The mixture was filtered and concentrated under reduced pressure to give N-methoxy-N-methyl-2-amino-4-fluoro-benzamide (0.9 g, 90%).

$^1$H NMR (300 MHz, CDCl₃): δ 7.44~7.39 (m, 1 H), 6.40~6.30 (m, 2 H), 4.90 (bs, 2 H), 3.57 (s, 3 H), 3.34 (s, 3 H).

Step 3. Synthesis of N-methoxy-N-methyl-4-fluoro-2-propylamino-benzamide

To a solution of N-methoxy-N-methyl-2-amino-4-fluoro-benzamide (0.27 g, 1.36 mmol), propionaldehyde (0.15 mL, 2.08 mmol), and AcOH (0.12 mL, 2.1 mmol) in dichloromethane (20 mL) was added sodium triacetoxyborohydride (576 mg, 2.72 mmol) at 5° C. The mixture was stirred for 90 minutes at the same temperature and then 40 minutes at room temperature. The reaction was quenched by adding water. The organic layer was washed with saturated aqueous NaHCO₃ solution and brine, dried over anhydrous magnesium sulfate, filtered, and concentrated under reduced pressure to give N-methoxy-N-methyl-4-fluoro-2-propylamino-benzamide quantitatively.

$^1$H NMR (300 MHz, CDCl₃): δ 7.40 (t, 1 H, J=7.2 Hz), 6.34~6.25 (m, 2 H), 3.58 (s, 3 H), 3.33 (s, 3 H), 3.03 (t, 2 H, J=6.9 Hz), 1.72~1.59 (m, 2 H), 1.00 (t, 3 H, J=7.2 Hz).

Step 4. Synthesis of 3-(4-fluoro-2-propylamino-phenyl)-acrylic acid methyl ester To a solution of N-methoxy-N-methyl-4-fluoro-2-propylamino-benzamide (0.33 g, 1.37 mmol) in THF (4 mL) was added dropwise LiAlH₄ (1 M in THF, 0.7 mL) at −45° C. The mixture was stirred for 40 minutes at −35° C. and then quenched by adding saturated aqueous KHSO₄ solution. The mixture was diluted with EtOAc, washed with 3 N HCl, and brine, dried over anhydrous magnesium sulfate, filtered, and concentrated under reduced pressure. The resulting residue was reacted with methyl (triphenylphosphoranylidene)acetate (0.5 g, 1.5 mmol) in toluene (4 mL) overnight at 100° C. The mixture was washed with water, dried over anhydrous magnesium sulfate, filtered, and concentrated under reduced pressure to give the title compound (0.23 g, 69%) after purification by column chromatography (EtOAc:hexane=1:10).

$^1$H NMR (300 MHz, CDCl₃): δ 7.72 (d, 1 H, J=15.6 Hz), 7.34~7.29 (m, 1 H), 6.41~6.29 (m, 2 H), 6.27 (d, 1 H, J=15.6 Hz), 4.16 (bs, 1 H), 3.80 (s, 3 H), 3.12~3.07 (m, 2 H), 1.76~1.63 (m, 2 H), 1.02 (t, 3 H, J=7.2 Hz).

Step 5. Synthesis of (R)—N-[1-(3,5-difluoro-4-methanesulfonylaminophenyl)ethyl]-3-(4-fluoro-2-propylamino-phenyl)-acrylamide To a solution of 3-(4-fluoro-2-propylamino-phenyl)-acrylic acid methyl ester (0.23 g, 0.95 mmol) in THF (4 mL) and MeOH (2 mL) was added 1 N LiOH (4 mL). The mixture was stirred for 2 hours at room temperature, concentrated under reduced pressure, and then acidified with 3 N HCl. The mixture was diluted with EtOAc, washed with water, dried over anhydrous magnesium sulfate, filtered, and concentrated under reduced pressure to give 3-(4-fluoro-2-propylamino-phenyl)-acrylic acid (0.17 g, 79%) after purification by crystallization form EtOAc and hexane. To a mixture of 3-(4-fluoro-2-propylamino-phenyl)-acrylic acid (50 mg, 0.22 mmol), (R)-[1-(3,5-difluoro-4-methanesulfonylaminophenyl)ethylamine hydrochloride (64 mg, 0.22 mmol) and N-methylmorpholine (36 μL, 0.33 mmol) in THF (5 mL) was added 4-(4,6-dimethoxy[1,3,5]triazin-2-yl)-4-methylmorpholirium chloride hydrate (DMTMM, 68 mg, 0.25 mmol). The mixture was stirred overnight at room temperature and then concentrated under reduced pressure. The residue was diluted with EtOAc and water, and the aqueous layer was washed with 2 N HCl and brine, dried over anhydrous magnesium sulfate, filtered, and concentrated under reduced pressure to give the title compound (35 mg, 34%) after purification by crystallization form EtOAc and hexane.

$^1$H NMR (300 MHz, CDCl₃): δ 7.78 (d, 1 H, J=15 Hz), 7.32~7.26 (m, 1 H), 6.93 (d, 2 H, J=8.4 Hz), 6.78 (s, 1 H), 6.37~6.29 (m, 2 H), 6.22 (d, 1 H, J=15 Hz), 5.87 (d, 1 H, J=6.9 Hz), 5.13 (t, 1 H, J=6.9 Hz), 4.48 (bs, 1 H), 3.18 (s, 3 H), 3.08 (t, 2 H, J=6.9 Hz), 1.71~1.58 (m, 2 H), 1.49 (d, 3 H, J=6.9 Hz), 0.99 (t, 3 H, J=7.2 Hz).

EXAMPLE 30

N-[1-(3,5-Difluoro-4-methanesulfonylaminobenzyl]-3-(4-fluoro-2-n-propylamino-phenyl)-acrylamide

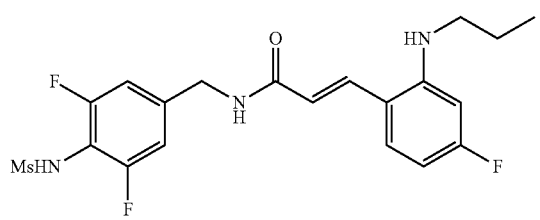

To a mixture of 3-(4-fluoro-2-propylamino-phenyl)-acrylic acid (50 mg, 0.22 mmol), (3,5-difluoro-4-methanesulfonylamino)benzylamine hydrochloride (61 mg, 0.22 mmol) and N-methylmorpholine (36 μL, 0.33 mmol) in THF (5 mL) was added 4-(4,6-dimethoxy[1,3,5]triazin-2-yl)-4-methylmorpholirium chloride hydrate (DMTMM, 68 mg, 0.25 mmol). The mixture was stirred overnight at room temperature and then concentrated under reduced pressure. The residue was diluted with EtOAc and water, and the aqueous layer was washed with 2 N HCl and brine, dried over anhydrous magnesium sulfate, filtered, and concentrated under reduced pressure to give the title compound (9 mg, 9%) after purification by column chromatography (EtOAc:hexane=1:1).

$^1$H NMR (300 MHz, CDCl₃): δ 7.60 (d, 1 H, J=15 Hz), 7.32~7.26 (m, 1 H), 6.96 (d, 2 H, J=8.1 Hz), 6.93~6.32 (m, 2 H), 6.14 (d, 1 H, J=15 Hz), 6.13 (br, 1 H), 5.95 (br, 1 H), 4.53

(d, 2 H, J=5.7 Hz), 4.25 (br, 1 H), 3.21 (s, 3 H), 3.09 (m, 2 H), 1.72~1.65 (m, 2 H), 1.01 (t, 3 H, J=7.2 Hz).

EXAMPLE 31

(R)-3-(2-Butoxy-4-trifluoromethyl-phenyl)-N-[1-(3,5-difluoro-4-methanesulfonylamino-phenyl)-ethyl]-acrylamide

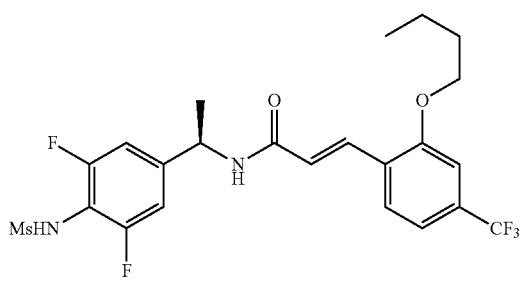

Step 1: Synthesis of 2-butoxy-4-trifluoromethyl-benzoic acid butyl ester

2-Hydroxy-4-trifluoromethyl-benzoic acid (755 mg) was reacted with butylbromide (0.96 ml) and $K_2CO_3$ (1.15 g) in DMF solution as described above to yield title compound.
$^1$H NMR (300 MHz, $CDCl_3$): δ 8.01 (s, 1H), 7.801 (d, 1H, J=7.8 Hz), 7.19 (m, 2H), 4.32 (t, 2H, J=6.6 Hz), 4.06 (t, 2H, J=6.3 Hz), 1.82 (m, 2H), 1.75 (m, 2H), 0.98 (m, 6H)

Step 2: Synthesis of 2-butoxy-4-trifluoromethyl-benzoic acid

2-Butoxy-4-trifluoromethyl-benzoic acid butyl ester was reacted with 1N LiOH (10 ml) as described above to yield title compound (687 mg).
$^1$H NMR (300 MHz, $CDCl_3$): δ 8.29 (d, 1H, J=8.4 Hz), 7.38 (d, 1H, J=8.1 Hz), 4.31 (t, 2H, J=6.3 Hz), 1.94 (m, 2H), 1.53 (m, 2H), 1.02 (t, 3H, J=7.5 Hz)

Step 3: Synthesis of 2-butoxy-N-methoxy-N-methyl-4-trifluoromethyl-benzamide

2-Butoxy-4-trifluoromethyl-benzoic acid (687 mg) was reacted with N,O-dimethylhydroxy amine (331 mg), NMM (0.65 ml) and DMTMM (911 mg) as described above to yield the title compound (825 mg) after column chromatography (Hex/EtOAc=7.5/1).
$^1$H NMR (300 MHz, $CDCl_3$): δ 7.36 (br, 1H), 7.22 (d, 1H, J=8.1 Hz), 7.11 (s, 1H), 4.04 (t, 2H, J=6.3 Hz), 3.45 (s, 3H), 3.35 (s, 3H), 1.77 (m, 2H), 1.46 (m, 2H), 0.99 (t, 3H, J=7.5 Hz)

Step 4: Synthesis of 2-butoxy-4-trifluoromethyl-benzaldehyde

2-Butoxy-N-methoxy-N-methyl-4-trifluoromethyl-benzamide (825 mg) was reacted with 1 M LAH (31 ml) at −50° C. for 1 hour as described above to yield title compound (423 mg) after column chromatography (Hex/EtOAc=20/1).
$^1$H NMR (300 MHz, $CDCl_3$): δ 10.53 (s, 1H), 7.92 (d, 1H, J=7.8 Hz), 7.27 (d, 1H, J=8.7 Hz), 7.21 (s, 1H), 4.10 (t, 2H, J=6.3 Hz), 1.89 (m, 2H), 1.57 (m, 2H), 1.01 (t, 3H, J=7.2 Hz)

Step 5: Synthesis of 3-(2-butoxy-4-trifluoromethyl-phenyl)-acrylic acid methyl ester 2-Butoxy-4-trifluoromethyl-benzaldehyde (420 mg) was reacted with methyl (triphenylphosphoranylidene)acetate (679 mg) at 110° C. overnight as described above to yield title compound (464 mg) after column chromatography (Hex/EtOAc=20/1).
$^1$H NMR (300 MHz, $CDCl_3$): δ 7.91 (d, 1H, J=16.5 Hz), 7.53 (d, 1H, J=7.8 Hz), 7.13 (m, 1H), 7.06 (s, 1H), 6.54 (d, 1H, J=16.2 Hz), 4.03 (t, 2H, J=6.6 Hz), 3.77 (s, 3H), 1.82 (m, 2H), 1.48 (m, 2H), 0.96 (t, 3H, J=7.5 Hz)

Step 6: Synthesis of 3-(2-butoxy-4-trifluoromethyl-phenyl)-acrylic acid 3-(2-Butoxy-4-trifluoromethyl-phenyl)-acrylic acid methyl ester (464 mg) was reacted with 1N LiOH (10 ml) in THF and $CH_3OH$ for 1 hr as described above to yield title compound
$^1$H NMR (300 MHz, $CDCl_3$): δ 8.05 (d, 1H, J=16.2 Hz), 7.60 (d, 1H, J=8.1 Hz), 7.20 (m, 1H), 7.12 (s, 1H), 6.62 (d, 1H, J=16.2 Hz), 4.09 (t, 2H, J=6.0 Hz), 1.85 (m, 2H), 1.56 (m, 2H), 1.04 (t, 3H, J=7.5 Hz)

Step 7: Synthesis of (R)-3-(2-butoxy-4-trifluoromethyl-phenyl)-N-[1-(3,5-difluoro-4-methanesulfonylamino-phenyl)-ethyl]-acrylamide (R)—N-(4-Aminoethyl-2,6-difluoro-phenyl)-methanesulfonamide, HCl salt (75 mg, 0.26 mmol) was reacted with 3-(2-butoxy-4-trifluoromethyl-phenyl)-acrylic acid (63 mg, 0.230 mmol), NMM (0.15 ml) and DMTMM (75 mg) at room temperature overnight to yield the title compound (52 mg, 0.10 mmol, 43%) after column chromatography (Hex/EtOAc=1/1).
$^1$H NMR (300 MHz, $CDCl_3$): δ 7.93 (d, 1H, J=15.6 Hz), 7.55 (d, 1H, J=7.8 Hz), 7.18 (d, 1H, J=8.1 Hz), 6.99 (d, 1H, J=6.6 Hz), 6.75 (d, 1H, J=8.4 Hz), 6.52 (d, 1H, J=15.6 Hz), 5.89 (br, 1H), 5.18 (t, 1H), 4.10 (d, 2H, J=6.0 Hz), 3.19 (s, 3H), 1.87 (m, 2H), 1.52 (m, 2H), 0.99 (t, 3H, J=7.2 Hz).
ESI [M−H]$^-$: 519

EXAMPLE 32

3-(2-Butoxy-4-trifluoromethyl-phenyl)-N-(3,5-difluoro-4-methanesulfonylamino-benzyl)-acrylamide

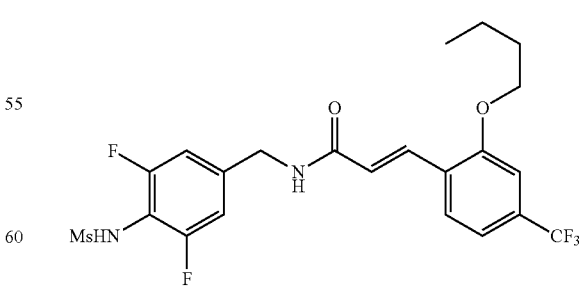

N-(4-Aminomethyl-2,6-difluoro-phenyl)-methanesulfonamide, HCl salt (65 mg, 0.24 mmol) was reacted with 3-(2-butoxy-4-trifluoromethyl-phenyl)-acrylic acid (57 mg, 0.20 mmol), NMM (0.2 ml) and DMTMM (66 mg) to give the title compound (62 mg, 012 mmol, 62%) after column chromatography (Hex/EtOAc=1/1).

¹H NMR (300 MHz, CDCl₃): δ 7.96 (d, 1H, J=15.6 Hz), 7.56 (d, 1H, J=8.1 Hz), 7.20 (d, 1H, J=7.2 Hz), 7.11 (s, 1H), 6.99 (d, 1H, J=8.1 Hz), 6.75 (d, 1H, J=8.1 Hz), 6.52 (d, 1H, J=15.6 Hz), 6.05 (br, 1H), 4.55 (d, 2H, J=6.3 Hz), 4.10 (d, 2H, J=6.9 Hz), 3.20 (s, 3H), 1.88 (m, 2H), 1.57 (m, 2H), 0.98 (t, 3H, J=7.2 Hz).

EXAMPLE 33

(R)-3-(2-Butoxy-4-fluoro-phenyl)-N-[1-(3,5-difluoro-4-methanesulfonylamino-phenyl)-ethyl]-acrylamide

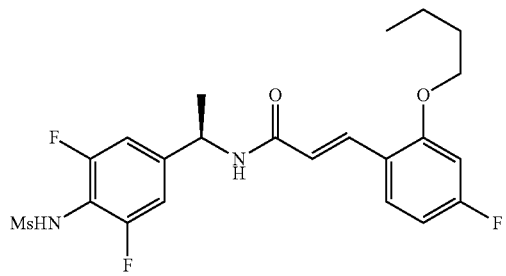

Step 1: Synthesis of 3-(2-butoxy-4-fluoro-phenyl)-acrylic acid methyl ester 3-(4-Fluoro-2-hydroxy-phenyl)-acrylic acid methyl ester (106 mg) was reacted with K₂CO₃ (125 mg) and butyl iodide (0.1 ml) at 80° C. for 3 hrs as described above to yield title compound (121 mg).

¹H NMR (300 MHz, CDCl₃): δ 7.90 (d, 1H, J=16.2 Hz), 7.45 (m, 1H), 6.64 (m, 2H), 6.47 (d, 1H, J=15.9 Hz), 4.00 (t, 2H, J=6.6 Hz), 3.79 (s, 3H), 1.84 (m, 2H), 1.53 (m, 2H), 0.99 (t, 3H, J=7.2 Hz)

Step 2: Synthesis of 3-(2-butoxy-4-fluoro-phenyl)-acrylic acid 3-(2-Butoxy-4-fluoro-phenyl)-acrylic acid methyl ester (121 mg) was reacted with 1N LiOH (5 ml) in THF and CH₃OH for 2 hrs as described above to yield title compound (116 mg).

¹H NMR (300 MHz, CDCl₃): δ 7.99 (d, 1H, J=16.2 Hz), 7.48 (m, 1H), 6.65 (m, 2H), 6.49 (d, 1H, J=16.2 Hz), 4.02 (t, 2H, J=6.3 Hz), 1.86 (m, 2H), 1.54 (m, 2H), 1.00 (t, 3H, J=7.2 Hz).

Step 3: Synthesis of (R)-3-(2-butoxy-4-fluoro-phenyl)-N-[1-(3,5-difluoro-4-methanesulfonylamino-phenyl)-ethyl]-acrylamide (R)—N-(4-Aminoethyl-2,6-difluoro-phenyl)-methanesulfonamide, HCl salt (75 mg, 0.26 mmol) was reacted with 3-(2-butoxy-4-fluoro-phenyl)-acrylic acid (60 mg, 0.25 mmol), NMM (0.15 ml) and DMTMM (82 mg) at room temperature overnight to yield the title compound (87 mg, 0.19 mmol, 74%) after column chromatography (Hex/EtOAc=1/1).

¹H NMR (300 MHz, CDCl₃): δ 7.85 (d, 1H, J=15.9 Hz), 7.42 (m, 1H), 6.94 (d, 2H, J=8.4 Hz), 6.62 (m, 2H), 6.47 (d, 1H, J=15.6 Hz), 6.23 (d, 1H, J=7.2 Hz), 5.13 (t, 1H), 4.11 (t, 2H, J=6.3 Hz), 3.17 (s, 3H), 1.81 (m, 2H), 1.54 (m, 2H), 1.46 (d, 3H, J=6.6 Hz), 0.90 (t, 3H, J=7.2 Hz).

ESI [M−H]⁻: 469

EXAMPLE 34

3-(2-Butoxy-4-fluoro-phenyl)-N-(3,5-difluoro-4-methanesulfonylamino-benzyl)-acrylamide

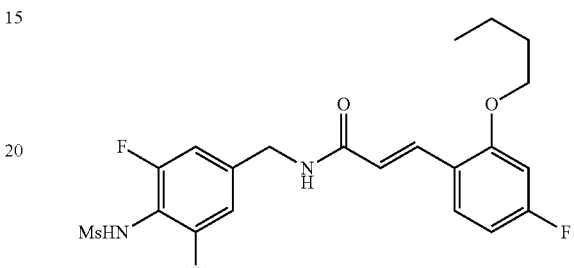

N-(4-Aminomethyl-2,6-difluoro-phenyl)-methanesulfonamide, HCl salt (73 mg, 0.26 mmol) was reacted with 3-(4-fluoro-2-propoxy-phenyl)-acrylic acid (55 mg, 0.23 mmol), NMM (0.15 ml) and DMTMM (73 mg) at room temperature overnight to yield the title compound (85 mg, 0.19 mmol, 81%) after column chromatography (Hex/EtOAc=1/1).

¹H NMR (300 MHz, CDCl₃): δ 7.89 (d, 1H, J=15.6 Hz), 7.45 (m, 1H), 6.94 (d, 2H, J=8.4 Hz), 6.98 (m, 1H), 6.64 (m, 1H), 6.50 (d, 1H, J=15.6 Hz), 6.07 (br, 1H), 4.55 (d, 2H, J=6.0 Hz), 4.13 (t, 2H, J=6.3 Hz), 3.20 (s, 3H), 1.83 (m, 2H), 1.52 (m, 2H), 0.88 (t, 3H, J=7.2 Hz).

EXAMPLE 35

N-(3-Ethynyl-5-fluoro-4-methanesulfonylamino-benzyl)-3-(2-propyl-4-trifluoromethyl-phenyl)-acrylamide

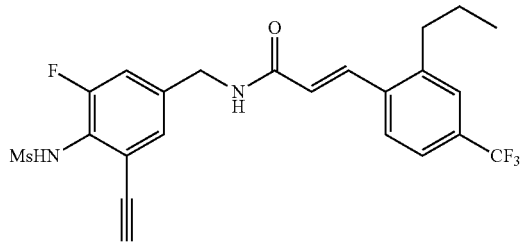

N-(4-Aminomethyl-2-ethynyl-6-fluoro-phenyl)-methanesulfonamide, HCl salt (14 mg, 0.050 mmol) was reacted with 3-(2-propyl-4-trifluoromethyl-phenyl)-acrylic acid (8 mg, 0.03 μmol) to give the title compound (12 mg, 80%) after purification by column chromatography (gradient 12% to 100% EtOAc in Hex).

¹H NMR (300 MHz, DMSO-d⁶): δ 8.79 (t, 1H), 7.69 (m, 4H), 7.74 (m, 2H), 7.60 (m, 2H), 7.26 (m, 2H), 6.72 (d, 1H,

J=15.6 Hz), 4.45 (s, 1H), 4.38 (d, 1H, J=5.4 Hz), 3.01 (s, 3H), 2.70 (t, 2H, J=7.5 Hz), 1.54 (m, 2 H), 1.23 (m, 2 H), 0.91 (m, 3H).
ESI [M+H]+:

EXAMPLE 36

(R)-3-(2-Butyl-4-trifluoromethyl-phenyl)-N-[1-(3-fluoro-4-methanesulfonylamino-phenyl)-ethyl]-acrylamide

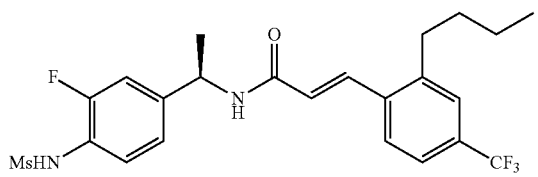

(R)—N-[4-(1-Amino-ethyl)-2-fluoro-phenyl]-methanesulfonamide, HCl salt (20 mg, 0.074 mmol) was reacted with 3-(2-butyl-4-trifluoromethyl-phenyl)-acrylic acid (8 mg, 0.031 mmol) to give the title compound (5 mg, 35%) after purification by column chromatography (gradient 12% to 100% EtOAc in Hex).
$^1$H NMR (300 MHz, DMSO-d$^6$): δ 8.66 (d, 1H, J=8.1 Hz), 7.66 (m, 3H), 7.51 (bs, 2H), 7.31 (t, 1H, J=8.4 Hz), 7.17 (d, 1H, J=11.4 Hz), 7.09 (d, 1H, J=8.1 Hz), 6.70 (d, 1H, J=15.6 Hz), 5.00 (m, 1H), 2.91 (s, 3H), 2.78 (t, 2H, J=7.8 Hz), 1.47 (m, 2 H), 1.40 (d, 3H, J=7.2 Hz), 1.32 (m, 2 H), 0.89 (t, 3H, J=7.2 Hz).
ESI [M−H]−: 485

EXAMPLE 37

N-[1-(3,5-Difluoro-4-methanesulfonylamino-phenyl)-propyl]-3-(2-ethoxy-4-trifluoromethyl-phenyl)-acrylamide

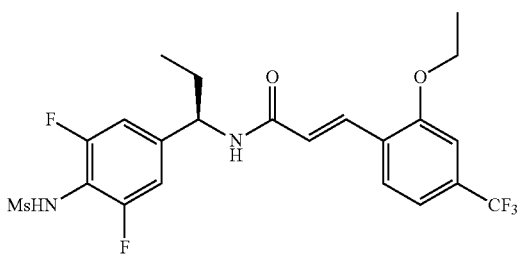

To a suspension of 3-(2-ethoxy-4-trifluoromethyl-phenyl)-acrylic acid (39 mg, 0.151 mmol) and N-[4-(1-amino-propyl)-2,6-difluoro-phenyl]-methanesulfonamide, HCl salt (50 mg, 0.166 mmol) in DMF (2 mL) was added N-methylmorpholine (0.02 ml, 0.018 mmol). The mixture was stirred for 5 minutes, to which were added N-(3-dimethylaminopropyl)-N'-ethylcarbodiimide hydrochloride (33 mg, 0.166 mmol). The mixture was stirred for 12 hours at room temperature, and then diluted with EtOAc (4 mL). The organic layer was washed with 1N HCl, water, and brine, dried over anhydrous magnesium sulfate, filtered and concentrated under reduced pressure. The crude residue was purified by chromatography (Hex/EtOAc=1/1) to give the title compound. (43 mg, 51%).
$^1$H NMR (300 MHz, DMSO-d$^6$): δ 9.50 (bs, 1H), 8.65 (d, 1H, J=7.8 Hz), 7.74 (d, 1H, J=7.8 Hz), 7.67 (d, 1H, J=15.9 Hz), 7.33 (d, 1H, J=8.1 Hz), 7.31 (s, 1H), 7.15 (d, 1H, J=8.7 Hz), 6.82 (d, 1H, J=15.9 Hz), 4.87-4.80 (m, 1H), 4.19 (q, 2H, J=6.9 Hz), 3.04 (s, 3H), 1.75-1.70 (m, 2H), 1.39 (t, 3H, J=6.9 Hz). 0.88 (t, 3H, J=6.9 Hz).

EXAMPLE 38

3-(2-Butoxy-4-trifluoromethyl-phenyl)-N-[1-(3,5-difluoro-4-methanesulfonylamino-phenyl)-propyl]-acrylamide

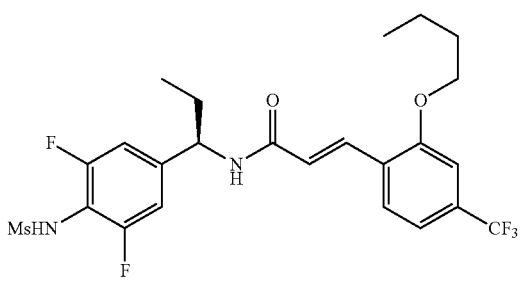

N-[4-(1-Amino-propyl)-2,6-difluoro-phenyl]-methanesulfonamide, HCl salt (50 mg, 0.166 mmol) was reacted with 3-(2-butoxy-4-trifluoromethyl-phenyl)-acrylic acid (43.5 mg, 0.151 mmol) to give the title compound (43 mg, 54%) after purification by column chromatography.
$^1$H NMR (300 MHz, DMSO-d$^6$): δ 9.47 (bs, 1H), 8.65 (d, 2H, J=8.1 Hz), 7.73 (d, 1H, J=8.4 Hz), 7.68 (d, 1H, J=16.2 Hz), 7.33 (s, 1H), 7.15 (d, 2H, J=8.7 Hz), 6.80 (d, 1H, J=16.2 Hz), 4.82 (q, 1H, J=7.2 Hz), 4.12 (d, 2H, J=6.3 Hz), 3.04 (s, 3H), 1.83-1.67 (m, 4H), 1.51-1.41 (m, 2H), 0.96-0.86 (m, 6H).

EXAMPLE 39

(R)-3-(2-sec-Butoxy-4-trifluoromethyl-phenyl)-N-[1-(3,5-difluoro-4-methanesulfonylamino-phenyl)-ethyl]-acrylamide

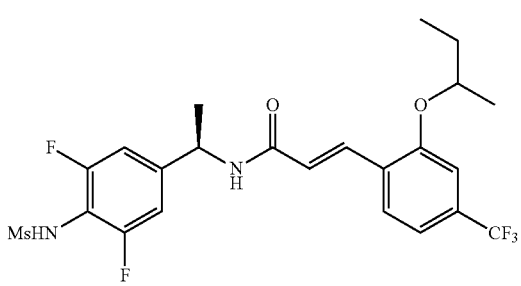

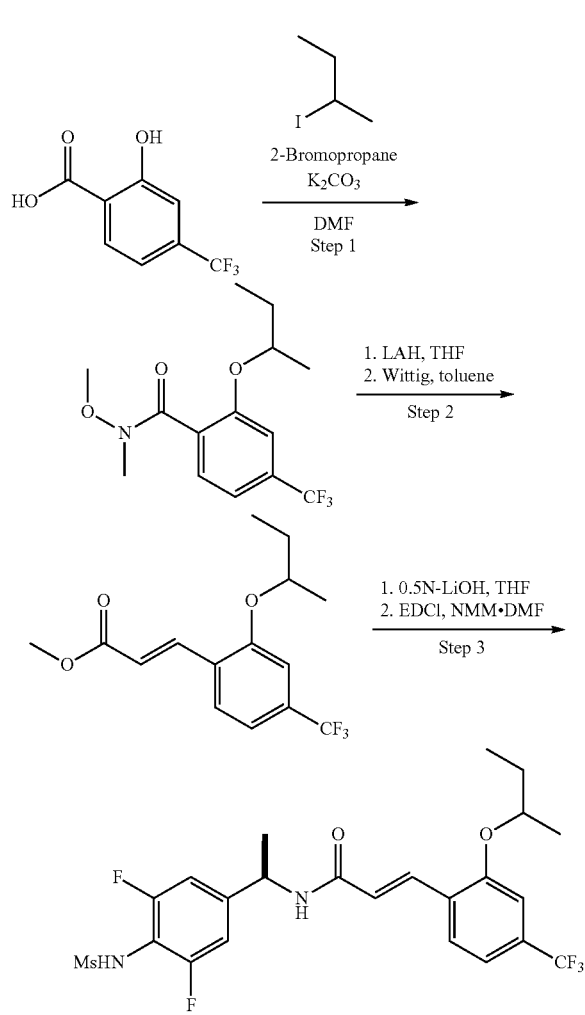

Step 1: Synthesis of 2-sec-butoxy-N-methoxy-N-methyl-4-trifluoromethyl-benzamide A mixture of 2-hydroxy-4-trifluoromethyl-benzoic acid (300 mg, 1.45 mmol) in DMF was added potassium carbonate (442 mg, 3.20 mmol) followed by 2-iodobutane (589 mg, 3.2 mmol). The mixture was stirred for 48 hours at 110° C. and then diluted with EtOAc. The organic layer was washed with 1N HCl, water, and brine, dried over anhydrous magnesium sulfate, filtered and concentrated under reduced pressure. The crude residue was dissolved in THF (2 ml) and then added a solution of 0.5 N-LiOH (2 eq). The mixture was stirred for 2 hours at room temperature and then diluted with EtOAc. The organic layer was washed with 1N HCl, water, and brine, dried over anhydrous magnesium sulfate, filtered and concentrated under reduced pressure. The crude residue and N,O-dimethylhydroxylamine hydrochloride (316 mg, 0.16 mmol) in $CH_2Cl_2$ (5 mL) was added N-methylmorpholine (0.176 ml, 0.160 mmol). The mixture was stirred for 5 minutes, to which were added N-(3-dimethylaminopropyl)-N'-ethylcarbodiimide hydrochloride (316 mg, 0.160 mmol). The mixture was stirred for 2 hours at room temperature and then diluted with EtOAc. The organic layer was washed with 1N HCl, water, and brine, dried over anhydrous magnesium sulfate, filtered and concentrated under reduced pressure. The crude residue was purified by chromatography to give the title compound. (374 mg, 84%).

$^1$H NMR (300 MHz, $CDCl_3$): δ 7.23-7.19 (m, 2H), 7.09 (s, 1H), 4.40-4.37 (m, 1H), 3.42 (s, 3H), 3.34 (s, 3H), 1.77-1.67 (m, 2H), 1.30 (d, 3H, J=3.0 Hz), 0.97 (t, 3H, J=7.2 Hz).

Step 2: Synthesis of 3-(2-sec-butoxy-4-trifluoromethyl-phenyl)-acrylic acid methyl ester 2-sec-Butoxy-N-methoxy-N-methyl-4-trifluoromethyl-benzamide (130 mg, 0.425 mmol) was processed with reduction and wittig reaction as described above to give the title compound (100 mg, 61%) after purification by column chromatography.

$^1$H NMR (300 MHz, $CDCl_3$): 7.97 (d, 1H, J=16.2 Hz), 7.58 (d, 1H, J=7.8 Hz), 7.17 (d, 1H, J=7.8 Hz), 7.09 (s, 1H), 6.57 (d, 1H, J=16.2 Hz), 4.48-4.42 (m, 1H), 3.81 (s, 3H), 1.86-1.69 (m, 2H), 1.35 (d, 3H, J=6.0 Hz), 1.01 (t, 3H, J=7.2 Hz).

Step 3: Synthesis of 3-(2-sec-butoxy-4-trifluoromethyl-phenyl)-N-[1-(3,5-difluoro-4-methanesulfonylamino-phenyl)-ethyl]-acrylamide N-[4-(1-Amino-ethyl)-2,6-difluoro-phenyl]-methanesulfonamide, HCl salt (17.7 mg, 0.062 mmol) was reacted with 3-(2-sec-butoxy-4-trifluoromethyl-phenyl)-acrylic acid (16.2 mg, 0.056 mmol) to give the title compound (15 mg, 52%) after purification by column chromatography.

$^1$H NMR (300 MHz, $CDCl_3$): δ 7.93 (d, 1H, J=15.9 Hz), 7.56 (d, 1H, J=8.1 Hz), 7.11 (d, 1H, J=8.1 Hz), 7.09 (s, 1H), 6.99 (d, 2H, J=8.1 Hz), 6.53 (d, 1H, J=15.9 Hz), 5.96 (d, 1H, J=7.2 Hz), 5.23-5.14 (m, 1H), 4.43 (q, 1H, J=6.0 Hz), 3.19 (s, 3H), 1.86-1.77 (m, 1H), 1.73-1.62 (m, 1H), 1.52 (d, 3H, J=6.9 Hz), 1.33 (d, 3H, J=6.0 Hz), 0.99 (t, 3H, J=7.2 Hz).
ESI [M−H]$^−$: 519

EXAMPLE 40

(R)-3-(2-sec-Butoxy-4-fluoro-phenyl)-N-[1-(3,5-difluoro-4-methanesulfonylamino-phenyl)-ethyl]-acrylamide

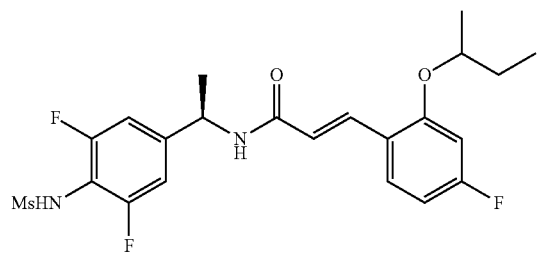

Step 1: Synthesis of 3-(2-sec-butoxy-4-fluoro-phenyl)-acrylic acid methyl ester 3-(4-Fluoro-2-hydroxy-phenyl)-acrylic acid methyl ester (120 mg) was reacted with $K_2CO_3$ (165 mg) and 2-iodobutan (0.12 ml) at 100° C. for 3 hrs as described above to yield title compound (105 mg)

$^1$H NMR (300 MHz, $CDCl_3$): δ 7.90 (d, 1H, J=15.9 Hz), 7.45 (m, 1H), 6.63 (m, 2H), 6.45 (d, 1H, J=15.9 Hz), 4.33 (m, 1H, J=6.0 Hz), 3.79 (s, 3H), 1.82 (m, 1H), 1.71 (m, 1H), 1.33 (d, 2H, J=6.0 Hz), 0.99 (t, 3H, J=7.2 Hz)

Step 2: Synthesis of 3-(2-sec-butoxy-4-fluoro-phenyl)-acrylic acid 3-(2-sec-Butoxy-4-fluoro-phenyl)-acrylic acid methyl ester (105 mg) was reacted with 1N LiOH (5 ml) in THF and $CH_3OH$ for 2 hrs as described above to yield title compound (82 mg)

$^1H$ NMR (300 MHz, $CDCl_3$): δ 7.97 (d, 1H, J=16.2 Hz), 7.50 (m, 1H), 6.62 (m, 2H), 6.47 (d, 1H, J=16.2 Hz), 4.02 (m, 1H, J=6.0 Hz), 1.86 (m, 1H), 1.73 (m, 1H), 1.34 (d, 3H), 1.00 (t, 3H, J=7.2 Hz).

Step 3: Synthesis of (R)-3-(2-sec-butoxy-4-fluoro-phenyl)-N-[1-(3,5-difluoro-4-methanesulfonylamino-phenyl)-ethyl]-acrylamide (R)—N-(4-Aminoethyl-2,6-difluoro-phenyl)-methanesulfonamide, HCl salt (69 mg, 0.24 mmol) was reacted with 3-(2-sec-butoxy-4-fluoro-phenyl)-acrylic acid (55 mg, 0.23 mmol), NMM (0.15 ml) and DMTMM (75 mg) at room temperature overnight to yield the title compound (15 mg, 14%) after column chromatography (Hex/EtOAc=1/1).

$^1H$ NMR (300 MHz, $CDCl_3$): δ 7.87 (d, 1H, J=15.6 Hz), 7.43 (m, 1H), 6.99 (d, 1H, J=8.7 Hz), 6.64 (m, 2H), 6.41 (d, 1H, J=15.6 Hz), 6.11 (s, 1H), 5.80 (d, 1H, J=7.5 Hz), 5.17 (t, 1H), 4.33 (m, 1H, J=6.0 Hz), 3.19 (s, 3H), 1.78 (m, 1H), 1.67 (m, 1H), 1.49 (d, 3H, J=7.2 Hz), 1.32 (d, 3H, J=6.0 Hz), 0.98 (t, 3H, J=7.2 Hz).

ESI [M−H]⁻: 469

EXAMPLE 41

3-(2-sec-Butoxy-4-fluoro-phenyl)-N-(3,5-difluoro-4-methanesulfonylamino-benzyl)-acrylamide

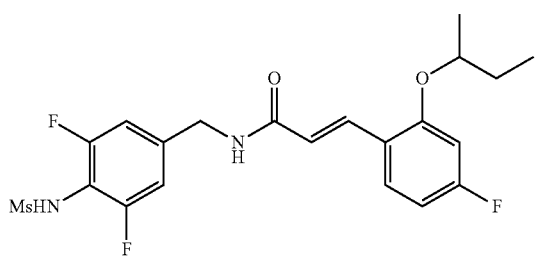

N-(4-Aminomethyl-2,6-difluoro-phenyl)-methanesulfonamide, HCl salt (42 mg, 0.15 mmol) was reacted with 3-(4-fluoro-2-propoxy-phenyl)-acrylic acid (34 mg, 0.14 mmol), NMM (0.15 ml) and DMTMM (43 mg) at room temperature overnight to yield the title compound (15 mg, 23%) after column chromatography (Hex/EtOAc=1/1).

$^1H$ NMR (300 MHz, $CDCl_3$): δ 7.89 (d, 1H, J=15.9 Hz), 7.44 (m, 1H), 6.97 (d, 1H, J=8.4 Hz), 6.65 (s, 1H), 6.60 (d, 1H, J=9.3 Hz), 6.47 (d, 1H, J=15.6 Hz), 6.08 (s, 1H), 6.00 (s, 1H, J=7.5 Hz), 4.53 (d, 2H, J=6.0 Hz), 4.34 (m, 1H, J=6.0 Hz), 3.20 (s, 3H), 1.78 (m, 1H), 1.67 (m, 1H), 1.49 (d, 3H, J=7.2 Hz), 1.34 (d, 3H, J=6.0 Hz), 0.99 (t, 3H, J=7.2 Hz).

EXAMPLE 42

(R)—N-[1-(3,5-Difluoro-4-methanesulfonylamino-phenyl)-ethyl]-3-(2-ethylamino-4-fluoro-phenyl)-acrylamide

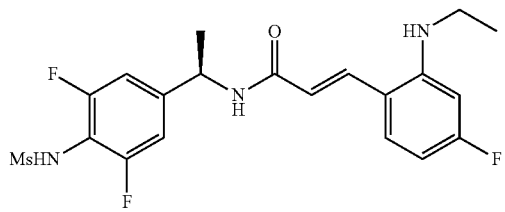

Step 1: Synthesis of N-methoxy-N-methyl-4-fluoro-2-ethylamino-benzamide

To a solution of N-methoxy-N-methyl-2-amino-4-fluoro-benzamide (0.20 g, 1.01 mmol), acetaldehyde (86 μL, 1.53 mmol), and AcOH (87 μL, 2.1 mmol) in dichloromethane (20 mL) was added sodium triacetoxyborohydride (430 mg, 2.03 mmol) at 5° C. The mixture was stirred for 90 minutes at the same temperature and then 40 minutes at room temperature. The reaction was quenched by adding water. The organic layer was washed with saturated aqueous $NaHCO_3$ solution and brine, dried over anhydrous magnesium sulfate, filtered, and concentrated under reduced pressure to give N-methoxy-N-methyl-4-fluoro-2-ethylamino-benzamide quantitatively.

$^1H$ NMR (300 MHz, $CDCl_3$): δ 7.43~7.38 (m, 1 H), 6.35~6.25 (m, 2 H), 3.58 (s, 3 H), 3.33 (s, 3 H), 3.16~3.07 (m, 2 H), 1.27 (t, 3 H, J=6.9 Hz).

Step 2: Synthesis of 3-(4-fluoro-2-ethylamino-phenyl)-acrylic acid methyl ester To a solution of N-methoxy-N-methyl-4-fluoro-2-ethylamino-benzamide (0.23 g, 1.02 mmol) in THF (4 mL) was added dropwise $LiAlH_4$ (1 M in THF, 0.51 mL) at −45° C. The mixture was stirred for 40 minutes at −35° C. and then quenched by adding saturated aqueous $KHSO_4$ solution. The mixture was diluted with EtOAc, washed with 3 N HCl, and brine, dried over anhydrous magnesium sulfate, filtered, and concentrated under reduced pressure. The residue was reacted with methyl (triphenylphosphoranylidene)acetate (375 mg, 1.12 mmol) in toluene (4 mL) overnight at 100° C. The mixture was washed with water, dried over anhydrous magnesium sulfate, filtered, and concentrated under reduced pressure to give the title compound (0.13 g, 57%) after purification by column chromatography (EtOAc:hexane=1:10).

$^1H$ NMR (300 MHz, $CDCl_3$): δ 7.73 (d, 1 H, J=15.6 Hz), 7.32 (t, 1 H, J=7.2 Hz), 6.42~6.32 (m, 2 H), 6.27 (d, 1 H, J=15.6 Hz), 4.09 (br, 1 H), 3.80 (s, 3 H), 3.19~3.15 (m, 2 H), 1.31 (t, 3 H, J=7.2 Hz).

Step 3: Synthesis of (R)—N-[1-(3,5-Difluoro-4-methanesulfonylaminophenyl)ethyl]-3-(4-fluoro-2-ethylaminophenyl)acrylamide To a solution of 3-(4-fluoro-2-ethylamino-phenyl)-acrylic acid methyl ester (128 mg, 0.57 mmol) in THF (4 mL) and MeOH (2 mL) was added 1 N LiOH (4 mL). The mixture was stirred for 2 hours at room temperature, concentrated under reduced pressure, and then acidified with 3 N HCl. The mixture was diluted with EtOAc, washed with water, dried over anhydrous magnesium sulfate, filtered, and concentrated under reduced pressure to give 3-(4-fluoro-2-ethylaminophenyl)-acrylic acid (88 mg, 73%) after purification by crystallization form EtOAc and hexane. To a mixture of 3-(4-fluoro-2-ethylamino-phenyl)-acrylic acid (40 mg, 0.19 mmol), (R)-[1-(3,5-difluoro-4-methanesulfonylaminophenyl)-ethylamine hydrochloride (55 mg, 0.19 mmol) and N-methylmorpholine (31 μL, 0.28 mmol) in THF (4 mL) was added 4-(4,6-dimethoxy[1,3,5]triazin-2-yl)-4-methylmorpholirium chloride hydrate (DMTMM, 58 mg, 0.21 mmol). The mixture was stirred overnight at room temperature and then concentrated under reduced pressure. The residue was diluted with EtOAc and water, washed with 2 N HCl and brine, dried over anhydrous magnesium sulfate, filtered, and concentrated under reduced pressure to give the title compound (4.9 mg, 6%) after purification by column chromatography (EtOAc:hexane=1:10 to 2:1).

$^1$H NMR (300 MHz, CDCl$_3$+DMSO-d6): δ 9.05 (br, 1 H), 8.00 (d, 1 H, J=7.8 Hz), 7.62 (d, 1 H, J=15.3 Hz), 7.29 (t, 1 H, J=7.8 Hz), 7.01 (d, 2 H, J=8.4 Hz), 6.40 (d, 1 H, J=15.3 Hz), 6.37~6.28 (m, 2H), 5.13 (t, 1H, J=6.9 Hz), 4.50 (bs, 1 H), 3.20~3.10 (m, 2 H), 3.08 (s, 3 H), 1.48 (d, 3 H, J=6.9 Hz), 1.28 (t, 3 H, J=7.2 Hz).

ESI [M−H]$^−$: 440

EXAMPLE 43

N-(3,5-Difluoro-4-methanesulfonylaminobenzyl)-3-(4-fluoro-2-ethylaminophenyl)acrylamide

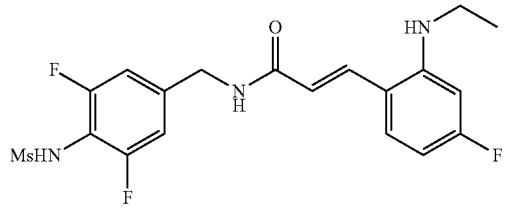

To a mixture of 4-fluoro-2-ethylaminocinnamic acid (40 mg, 0.19 mmol), (3,5-difluoro-4-methanesulfonylamino)benzylamine hydrochloride (52 mg, 0.19 mmol) and N-methylmorpholine (31 μL, 0.28 mmol) in THF (4 mL) was added 4-(4,6-dimethoxy[1,3,5]triazin-2-yl)-4-methylmorpholirium chloride hydrate (DMTMM, 58 mg, 0.21 mmol). The mixture was stirred overnight at room temperature and then concentrated under reduced pressure. The residue was diluted with EtOAc and water, and the organic layer was washed with 2 N HCl and brine, dried over anhydrous magnesium sulfate, filtered, and concentrated under reduced pressure to give the title compound (17 mg, 21%) after trituration with ethyl ether.

$^1$H NMR (300 MHz, CDCl$_3$+DMSO-d6): δ 9.07 (bs, 1 H), 8.14 (br, 1 H), 7.66 (d, 1 H, J=15.6 Hz), 7.31 (t, 1 H, J=7.2 Hz), 6.98 (d, 2 H, J=8.1 Hz), 6.40 (d, 1 H, J=15.3 Hz), 6.37~6.29 (m, 2 H), 4.55 (br, 1 H), 4.47 (d, 2 H, J=5.7 Hz), 3.18~3.12 (m, 2 H), 3.09 (s, 3 H), 1.29 (t, 3 H, J=7.2 Hz).

EXAMPLE 44

(R)—N-(2-Fluoro-4-{1-[3-(2-propyl-4-trifluoromethyl-phenyl)-allylamino]-ethyl}-phenyl)-methanesulfonamide

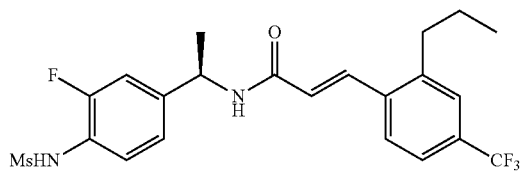

(R)—N-[4-(1-Amino-ethyl)-2-fluoro-phenyl]-methanesulfonamide, HCl salt (31 mg, 0.12 mmol) was reacted with 3-(2-propyl-4-trifluoromethyl-phenyl)-acrylic acid (25 mg, 0.097 mmol) to give the title compound (32 mg, 70%) after purification by recrystallization from Hex/EtOAc.

$^1$H NMR (300 MHz, DMSO-d6): δ 8.70 (d, 1H, J=7.5 Hz), 7.66 (m, 3H), 7.33 (t, 1H, J=8.1 Hz), 7.23 (d, 1H, J=11.7 Hz), 7.15 (d, 1H, J=8.4 Hz), 6.70 (d, 1H, J=15.6 Hz), 5.02 (m, 1H), 2.98 (s, 3H), 2.75 (t, 2H, J=6.9 Hz), 1.50 (m, 2 H), 1.40 (d, 3H, J=6.9 Hz), 1.32 (m, 2 H), 0.89 (t, 3H, J=7.5 Hz).

EXAMPLE 45

(R)-3-(2-Butylamino-4-fluoro-phenyl)-N-[1-(3,5-difluoro-4-methanesulfonylamino-phenyl)-ethyl]-acrylamide

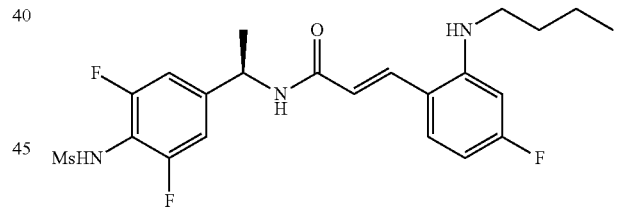

Step 1: Synthesis of N-methoxy-N-methyl-4-fluoro-2-n-butylamino-benzamide

To a solution of N-methoxy-N-methyl-2-amino-4-fluorobenzoic acid amide (0.35 g, 1.75 mmol), butyrylaldehyde (0.23 mL, 2.62 mmol), and AcOH (0.15 mL, 2.62 mmol) in dichloromethane (20 mL) was added sodium triacetoxyborohydride (0.74 g, 3.49 mmol) at 5° C. The mixture was stirred for 5 hours at the same temperature and overnight at room temperature. The reaction was quenched by adding water. The organic layer was washed with saturated aqueous NaHCO$_3$ solution and brine, dried over anhydrous magnesium sulfate, filtered, and concentrated under reduced pressure to give the title compound quantitatively.

$^1$H NMR (300 MHz, CDCl$_3$): δ 7.43~7.38 (m, 1 H), 6.35~6.24 (m, 2 H), 3.58 (s, 3 H), 3.33 (s, 3 H), 3.10~3.02 (m, 2 H), 1.67~1.35 (m, 4 H), 0.95 (t, 3 H, J=7.2 Hz).

Step 2: Synthesis of 3-(4-fluoro-2-butylamino-phenyl)-acrylic acid methyl ester To a solution of N-methoxy-N-methyl-4-fluoro-2-n-butylamino-benzamide (0.5 g, 1.97 mmol) in THF (8 mL) was added dropwise LiAlH₄ (1 M in THF, 1.0 mL) at −45° C. The mixture was stirred for 40 minutes at −35° C. and then quenched by adding saturated aqueous KHSO₄ solution. The mixture was diluted with EtOAc, washed with 3 N HCl, and brine, dried over anhydrous magnesium sulfate, filtered, and concentrated under reduced pressure. The resulting residue was reacted with methyl (triphenylphosphoranylidene)acetate (725 mg, 2.17 mmol) in toluene (4 mL) overnight at 100° C. The mixture was washed with water, dried over anhydrous magnesium sulfate, filtered, and concentrated under reduced pressure to give the title compound (0.15 g, 30%) after purification by column chromatography (EtOAc: hexane=1:10).

$^1$H NMR (300 MHz, CDCl$_3$): δ 7.71 (d, 1 H, J=15.9 Hz), 7.31 (t, 1 H, J=8.4 Hz), 6.42~6.31 (m, 2 H), 6.26 (d, 1 H, J=15.9 Hz), 4.13 (br, 1 H), 3.15~3.09 (m, 2 H), 1.71~1.61 (m, 2 H), 1.49~1.41 (m, 2 H), 0.98 (t, 3 H, J=7.2 Hz).

Step 3: Synthesis of (R)—N-[1-(3,5-Difluoro-4-methanesulfonylaminophenyl)ethyl]-3-(4-fluoro-2-n-butylaminophenyl)acrylamide To a solution of 3-(4-fluoro-2-butylamino-phenyl)-acrylic acid methyl ester (145 mg, 0.58 mmol) in THF (4 mL) and MeOH (2 mL) was added 1 N LiOH (4 mL). The mixture was stirred for 2 hours at room temperature, concentrated under reduced pressure, and then acidified with 3 N HCl. The mixture was diluted with EtOAc, washed with water, dried over anhydrous magnesium sulfate, filtered, and concentrated under reduced pressure to give 3-(4-fluoro-2-butylamino-phenyl)-acrylic acid (120 mg, 88%) after purification by crystallization form EtOAc and hexane. To a mixture of 3-(4-fluoro-2-butylamino-phenyl)-acrylic acid (52 mg, 0.22 mmol), (R)-[1-(3,5-difluoro-4-methanesulfonylaminophenyl)ethylamine hydrochloride (64 mg, 0.22 mmol) and N-methylmorpholine (36 μL, 0.33 mmol) in THF (5 mL) was added 4-(4,6-dimethoxy[1,3,5]triazin-2-yl)-4-methylmorpholirium chloride hydrate (DMTMM, 68 mg, 0.25 mmol). The mixture was stirred overnight at room temperature and then concentrated under reduced pressure. The residue was diluted with EtOAc and water, washed with 2 N HCl and brine, dried over anhydrous magnesium sulfate, filtered, and concentrated under reduced pressure to give the title compound (4.5 mg, 4%) after trituration with ethyl ether. 2:1).

$^1$H NMR (300 MHz, CDCl$_3$): δ 7.78 (d, 1 H, J=14.7 Hz), 7.30 (t, 1 H, J=6.9 Hz), 6.95~6.90 (m, 3 H), 6.36~6.30 (m, 2 H), 6.23 (d, 1 H, J=14.7 Hz), 5.95 (d, 1 H, J=6.6 Hz), 5.11 (t, 1 H, J=6.9 Hz), 4.50 (bs, 1 H), 3.18 (s, 3 H), 3.10 (t, 2 H, J=6.9 Hz), 1.68~1.58 (m, 2 H), 1.48 (d, 3 H, J=6.9 Hz), 1.43~1.38 (m, 2 H), 0.95 (t, 3 H, J=7.2 Hz).

ESI [M−H]⁻: 468

EXAMPLE 46

3-(2-Butylamino-4-fluoro-phenyl)-N-(3,5-difluoro-4-methanesulfonylamino-benzyl)-acrylamide

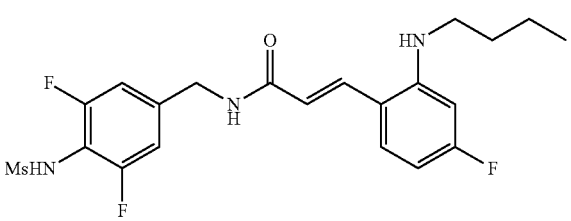

To a mixture of 3-(4-fluoro-2-butylamino-phenyl)-acrylic acid (52 mg, 0.22 mmol), (3,5-difluoro-4-methanesulfonylamino)benzylamine hydrochloride (61 mg, 0.22 mmol) and N-methylmorpholine (36 μL, 0.33 mmol) in THF (5 mL) was added 4-(4,6-dimethoxy[1,3,5]triazin-2-yl)-4-methylmorpholirium chloride hydrate (DMTMM, 68 mg, 0.25 mmol). The mixture was stirred overnight at room temperature and then concentrated under reduced pressure. The residue was diluted with EtOAc and water, washed with 2 N HCl and brine, dried over anhydrous magnesium sulfate, filtered, and concentrated under reduced pressure to give the title compound (45 mg, 45%) after trituration with ethyl ether.

$^1$H NMR (300 MHz, CDCl$_3$+DMSO-d6): δ 8.71 (bs, 1 H), 7.73 (br, 1 H), 7.68 (d, 1 H, J=15.6 Hz), 7.30 (t, 1 H, J=7.5 Hz), 6.97 (d, 2 H, J=8.4 Hz), 6.40~6.30 (m, 3 H), 4.49 (d, 2 H, J=6 Hz), 3.14~3.09 (m, 5 H), 1.69~1.59 (m, 2 H), 1.50~1.38 (m, 2 H), 0.96 (t, 3 H, J=7.5 Hz).

EXAMPLE 47

(R)—N-[1-(3,5-Difluoro-4-methanesulfonylaminophenyl)-ethyl]-3-(2-isobutyl-4-trifluoromethyl-phenyl)-acrylamide

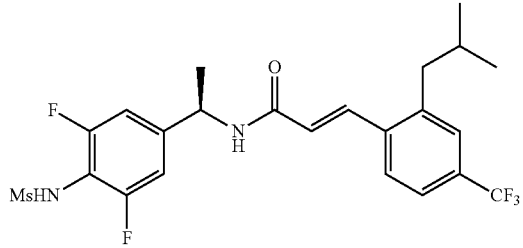

3-(2-Isopropyl-4-trifluoromethyl-phenyl)-acrylic acid was obtained by the procedure in example 21.

(R)—N-[4-(1-Amino-ethyl)-2,6-difluoro-phenyl]-methanesulfonamide, HCl salt (55 mg, 0.20 mmol) was reacted with 3-(2-isobutyl-4-trifluoromethyl-phenyl)-acrylic acid (40 mg, 0.15 mmol) to give the title compound (18 mg, 24%) after purification by recrystallization from ether. $^1$H NMR (300 MHz, DMSO-d$^6$): δ 8.74 (d, 1H, J=7.8 Hz), 7.67 (m, 4H), 7.17 (d, 2H, J=8.7 Hz), 6.70 (d, 1H, J=15.6 Hz), 5.03 (m, 1H), 3.04 (s, 3H), 2.78 (t, 2H), 2.67 (m, 1H), 1.47 (m, 2 H), 1.41 (d, 3H, J=6.9 Hz), 1.31 (m, 2 H), 0.87 (m, 9H).

EXAMPLE 48

(R)—N-[1-(3,5-Difluoro-4-methanesulfonylamino-phenyl)-ethyl]-2-methyl-3-(2-propyl-4-trifluoromethyl-phenyl)-acrylamide

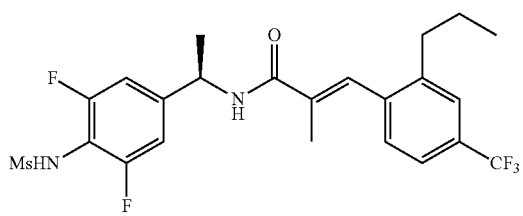

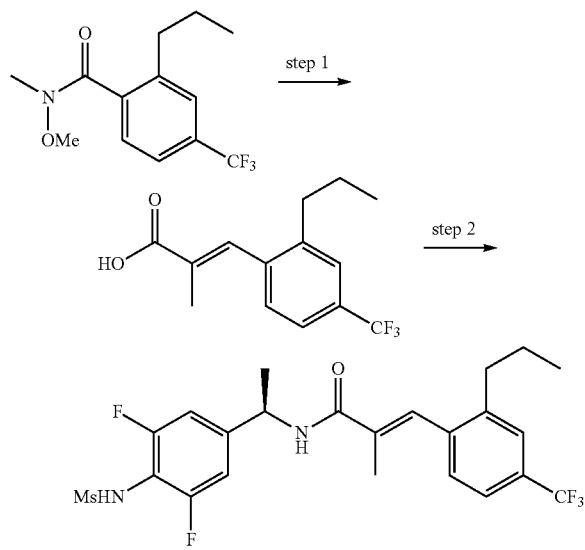

Step 1: Synthesis of 2-methyl-3-(2-propyl-4-trifluoromethyl-phenyl)-acrylic acid To a suspension of N-methoxy-N-methyl-2-propyl-4-trifluoromethyl-benzamide (150 mg, 0.58 mmol) in THF (10 mL) was added dropwise 1.0M LiAlH₄ (0.30 mL, 0.30 mmol) at −78° C. The mixture was warmed up to −20° C. and stirred for 30 mins. An aqueous solution of sodium potassium tartarate (10% w/v) was added to the reaction mixture and the resulting mixture was vigorously stirred for 30 mins, to which was added Et₂O. After separation of two phases, the aqueous layer was extracted three times with ether and the combined organic layer was washed with brine, dried over anhyd. MgSO₄, filtered and concentrated under reduced pressure. The product was vacuum dried to yield the 2-propyl-4-trifluoromethyl-benzaldehyde.

To an ice-cold suspension of NaH (60% in mineral oil, 45 mg, 1.13 mmol) in THF (2 mL) was added triethyl-2-phosphonopropionate (0.16 mL, 0.75 mmol), and the resulting mixture was stirred for 10 mins at ambient temperature. A solution of aldehyde obtained above in THF was added to the reaction mixture and the resulting mixture was stirred for 3 hrs at ambient temperature. The reaction mixture was diluted with water and EtOAc, and the aqueous layer was extracted three times with EtOAc. The combined organic layer was dried over anhydrous MgSO₄ and concentrated under reduced pressure. The resulting residue was purified by column chromatography (gradient 12% to 100% EtOAc in Hex) to give 2-methyl-3-(2-propyl-4-trifluoromethyl-phenyl)-acrylic acid ethyl ester (68 mg, 39%).

To a suspension of 2-methyl-3-(2-propyl-4-trifluoromethyl-phenyl)-acrylic acid ethyl ester (68 mg, 0.23 mmol) in THF (1 mL) was added a solution of 1N-LiOH (10 ml), and the mixture was stirred for 3 hours at room temperature. The resulting residue was dissolved in H₂O and then washed three times with EtOAc, acidified with 1N HCl to pH 1-2. The solution was extracted three times with methylene chloride and then dried over anhydrous MgSO₄ and concentrated in vacuo to give the title compound (60 mg, 96%).

¹H NMR (300 MHz, CDCl₃): δ 7.91 (s, 1H), 7.48 (bs, 2H), 7.30 (d, 1H, J=8.7 Hz), 2.63 (t, 2H, J=8.1 Hz), 1.96 (s, 3H), 1.61 (m, 2H), 0.95 (t, 3H, J=7.2 Hz).

Step 2: Synthesis of (R)—N-[1-(3,5-difluoro-4-methanesulfonylamino-phenyl)-ethyl]-2-methyl-3-(2-propyl-4-trifluoromethyl-phenyl)-acrylamide To a suspension of (R)—N-[4-(1-amino-ethyl)-2,6-difluoro-phenyl]-methanesulfonamide, HCl salt (30 mg, 0.11 mmol) in THF (2 mL) was added N-methylmorpholine (23 μl, 0.21 mmol). The mixture was stirred for 5 minutes, to which were added 2-methyl-3-(2-propyl-4-trifluoromethyl-phenyl)-acrylic acid (22 mg, 0.081 mmol) and 4-(4,6-dimethoxy[1,3,5]triazin-2-yl)-4-methylmorpholinium chloride hydrate (DMTMM, 27 mg, 0.098 mmol). The mixture was stirred overnight at room temperature and was concentrated under reduced pressure. The residue was diluted with EtOAc and water. The organic layer was washed with saturated sodium bicarbonate, 1N HCl and brine, dried over anhydrous magnesium sulfate, filtered, and concentrated under reduced pressure. The crude residue was purified by column chromatography (gradient 12% to 100% EtOAc in Hex) to give title compound (18 mg, 44%).

¹H NMR (300 MHz, DMSO-d6): δ 8.41 (d, 1H, J=7.8 Hz), 7.58 (m, 2H), 7.41 (m, 2H), 7.13 (d, 2H, J=8.4 Hz), 5.04 (m, 1H), 2.97 (s, 3H), 2.62 (t, 2H), 1.86 (s, 3H), 1.52 (m, 2 H), 1.43 (d, 3H, J=6.9 Hz), 0.87 (t, 3H, J=7.2 Hz).

EXAMPLE 49

(R)—N-[1-(3-Fluoro-4-methanesulfonylamino-phenyl)-ethyl]-2-methyl-3-(2-propyl-4-trifluoromethyl-phenyl)-acrylamide

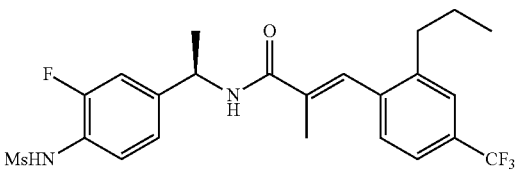

(R)—N-[4-(1-Amino-ethyl)-2-fluoro-phenyl]-methanesulfonamide, HCl salt (52 mg, 0.19 mmol) was reacted with 2-methyl-3-(2-propyl-4-trifluoromethyl-phenyl)-acrylic acid (40 mg, 0.15 mmol) to give the title compound (68 mg, 93%) after purification by column chromatography (gradient 12% to 100% EtOAc in Hex).

$^1$H NMR (300 MHz, DMSO-d6): δ 9.51 (bs, 1H), 8.41 (d, 1H, J=7.8 Hz), 7.58 (m, 2H), 7.29 (m, 5H), 5.06 (m, 1H), 3.00 (s, 3H), 2.60 (t, 2H), 1.86 (s, 3H), 1.50 (m, 2 H), 1.44 (d, 3H, J=7.2 Hz), 0.87 (t, 3H, J=7.5 Hz).

EXAMPLE 50

(R)-3-(2-Cyclohexylmethoxy-4-trifluoromethyl-phenyl)-N-[1-(3,5-difluoro-4-methanesulfonylamino-phenyl)-ethyl]-acrylamide

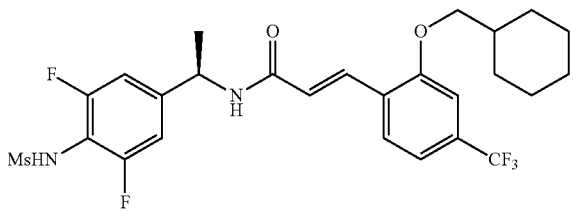

with 1N LiOH (2.65 mg, 2.65 mmol) as described above to give 2-cyclohexylmethoxy-4-trifluoromethyl-benzoic acid (361 mg, 90%) after drying by vacuum.

2-Cyclohexylmethoxy-4-trifluoromethyl-benzoic acid (361 mg, 1.19 mmol) was reacted with N,O-dimethylhydroxyamine, HCl salt (128 mg, 1.31 mmol) as described above to give the title compound (363 mg, 88%) after purification by vacuum dry.

$^1$H NMR (300 MHz, CDCl$_3$): δ 7.36 (s, 1H), 7.23 (d, 1H, J=7.5 Hz), 7.10 (s, 1H), 3.83 (d, 2H, J=5.7 Hz), 3.42 (s, 3H), 3.37 (s, 3H), 1.84-1.73 (m, 6H), 1.49-1.05 (m, 5H).

Step 3: Synthesis of 3-(2-cyclohexylmethoxy-4-trifluoromethyl-phenyl)-acrylic acid methyl ester 2-Cyclohexylmethoxy-N-methoxy-N-methyl-4-trifluoromethyl-benzamide (363 mg, 1.05 mmol) was processed by LAH reduction and wittig reaction as described above to give the title compound (250 mg, 69%) after purification by column chromatography (n-Hex/EtOAc=20/1).

$^1$H NMR (300 MHz, CDCl$_3$): δ 7.97 (d, 1H, J=16.2 Hz), 7.58 (d, 1H, J=7.8 Hz), 7.19 (d, 1H, J=7.8 Hz), 7.09 (s, 1H),

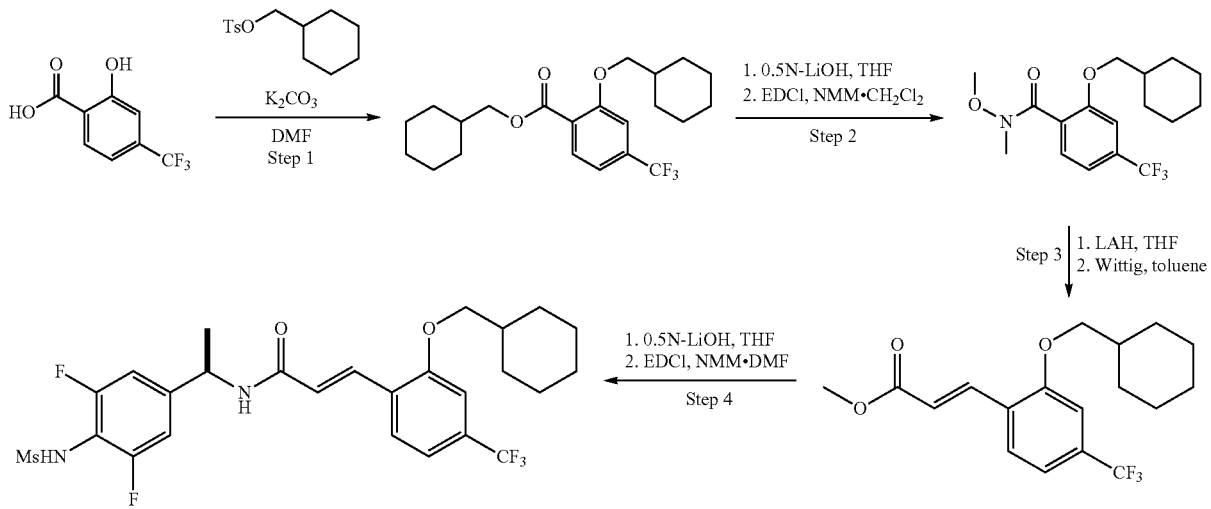

Step 1: Synthesis of 2-cyclohexylmethoxy-4-trifluoromethyl-benzoic acid cyclohexylmethyl ester 2-Hydroxy-4-trifluoromethyl-benzoic acid (246 mg, 1.19 mmol) was reacted with toluene-4-sulfonic acid cyclohexylmethyl ester (640 mg, 2.34 mmol) as described above to give the title compound (470 mg, 99%) after purification by column chromatography.

$^1$H NMR (300 MHz, CDCl$_3$): δ 7.83 (d, 1H, J=7.8 Hz), 7.20 (d, 1H, J=7.8 Hz), 7.13 (s, 1H), 4.13 (d, 2H, J=6.6 Hz), 3.84 (d, 2H, J=5.7 Hz), 2.04-1.74 (m, 12H), 1.33-1.02 (m, 10H).

Step 2: Synthesis of 2-cyclohexylmethoxy-N-methoxy-N-methyl-4-trifluoromethyl-benzamide 2-Cyclohexylmethoxy-4-trifluoromethyl-benzoic acid cyclohexylmethyl ester (528 mg, 1.33 mmol) was reacted 6.60 (d, 1H, J=16.2 Hz), 3.86 (d, 2H, J=5.7 Hz), 3.82 (s, 3H), 1.91-1.77 (m, 6H), 1.43-1.05 (m, 5H).

Step 4: Synthesis of 3-(2-cyclohexylmethoxy-4-trifluoromethyl-phenyl)-N-[1-(3,5-difluoro-4-methanesulfonylamino-phenyl)-ethyl]-acrylamide

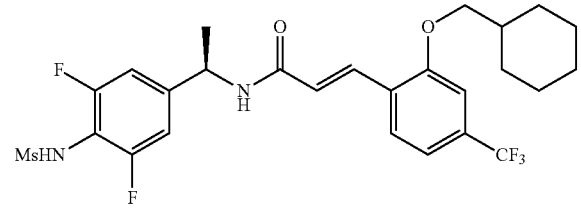

N-[4-(1-Amino-ethyl)-2,6-difluoro-phenyl]-methanesulfonamide, HCl salt (28.8 mg, 0.101 mmol) was reacted with 3-(2-cyclohexylmethoxy-4-trifluoromethyl-phenyl)-acrylic acid (30 mg, 0.091 mmol) to give the title compound (33 mg, 65%) after purification by column chromatography.

$^1$H NMR (300 MHz, CDCl$_3$): δ 7.88 (d, 1H, J=15.6 Hz), 7.50 (d, 1H, J=8.1 Hz), 7.12 (d, 1H, J=8.1 Hz), 7.03 (s, 1H), 6.94 (d, 2H, J=8.4 Hz), 6.51 (d, 1H, J=15.9 Hz), 6.04 (s, 1H), 5.82 (d, 1H, J=7.2 Hz), 5.17-5.10 (m, 1H), 3.80 (d, 1H, J=5.7 Hz), 3.15 (s, 3H), 1.86-1.65 (m, 6H), 1.47 (d, 3H, J=6.9 Hz), 1.28-1.02 (m, 5H).

EXAMPLE 51

N-(3,5-Difluoro-4-methanesulfonylamino-benzyl)-3-(2-piperidin-1-yl-4-trifluoromethyl-phenyl)-acrylamide

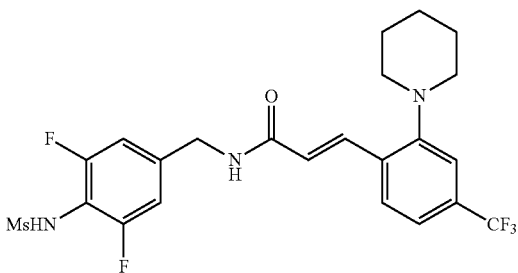

N-(4-Aminomethyl-3,5-difluoro-phenyl)-methanesulfonamide, HCl salt (59 mg, 0.217 mmol) was reacted with 3-(2-piperid-1-yl-4-trifluoromethyl-phenyl)-acrylic acid (65 mg, 0.217 mmol) to give the title compound (25 mg, 22%) after purification by crystallization from Hex/EtOAc.

$^1$H NMR (300 MHz, CDCl$_3$): δ 7.98 (d, 1H, J=15.6 Hz), 7.60 (m, 2H), 6.99 (m, 2H), 6.79 (d, 1H, J=8.4 Hz), 6.46 (d, 1H, J=15.6 Hz), 6.00 (s, 1H), 4.37 (d, 2H, J=6.3 Hz), 3.21 (s, 3H), 2.92 (m, 4H), 1.77 (m, H), 1.61 (m, 4H)

EXAMPLE 52

(R)—N-[1-(3,5-Difluoro-4-methanesulfonylamino-phenyl)-3-(2-piperidin-1-yl-4-trifluoromethyl-phenyl)-acrylamide

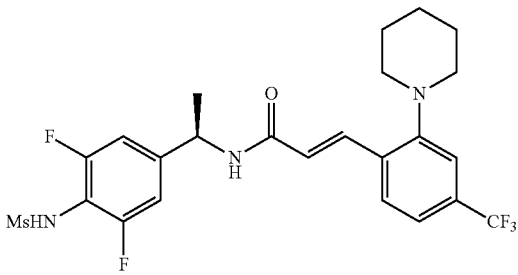

(R)—N-[4-(1-Amino-ethyl)-2,6-difluoro-phenyl]-methanesulfonamide, HCl salt (129 mg, 0.451 mmol) was reacted with 3-(2-piperid-1-yl-4-trifluoromethyl-phenyl)-acrylic acid (135 mg, 0.45 μmol) to give the title compound (65 mg, 27%) after purification by crystallization from Hex/EtOAc.

$^1$H NMR (300 MHz, CDCl$_3$): δ 7.94 (d, 1H, J=15.9 Hz), 7.55 (d, 1H, J=8.4 Hz), 7.23 (m, 2H), 7.01 (m, 2H), 6.43 (d, 1H, J=15.6 Hz), 5.99 (s, 1H), 5.83 (s, 1H), 5.20 (m, 1H), 3.21 (s, 3H), 2.92 (m, 4H), 1.76 (m, 4H), 1.59 (m, 2H), 1.53 (d, 3H, J=6.6 Hz).

EXAMPLE 53

(R)—N-[1-(3,5-Difluoro-4-methanesulfonylamino-phenyl)-ethyl]-3-(4-fluoro-2-propyl-phenyl)-acrylamide

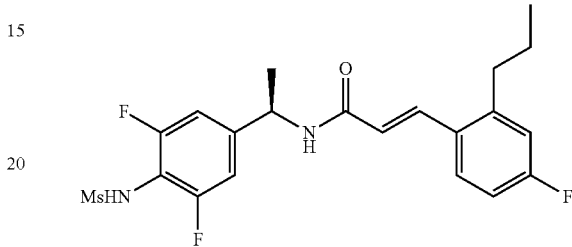

3-(4-Fluoro-2-propyl-phenyl)-acrylic acid was prepared as described above. (R)—N-(4-Aminoethyl-2,6-difluoro-phenyl)-methanesulfonamide, HCl salt (28 mg, 0.097 mmol) was reacted with 3-(4-fluoro-2-propyl-phenyl)-acrylic acid (15 mg, 0.072 mmol), NMM (0.20 ml) and DMTMM (36 mg) at room temperature overnight to yield the title compound (12 mg, 38%) after column chromatography (Hex/EtOAc=3/2).

$^1$H NMR (300 MHz, CDCl$_3$): δ 7.91 (d, 1H, J=15.3 Hz), 7.00 (d, 1H, J=8.4 Hz), 7.48 (m, 1H), 6.92 (m, 2H), 6.25 (d, 1H, J=15.3 Hz), 6.05 (br, 1H), 5.82 (d, 1H, J=6.9 Hz), 5.17 (t, 1H, J=7.1 Hz), 3.20 (s, 1H), 2.72 (t, 2H, J=7.5 Hz), 1.60 (m, 2H), 0.95 (t, 3H, J=7.2 Hz)

EXAMPLE 54

N-(3-fluoro-4-methanesulfonylamino-5-vinyl-benzyl)-3-(2-isopropylamino-4-trifluoromethyl-phenyl)-acrylamide

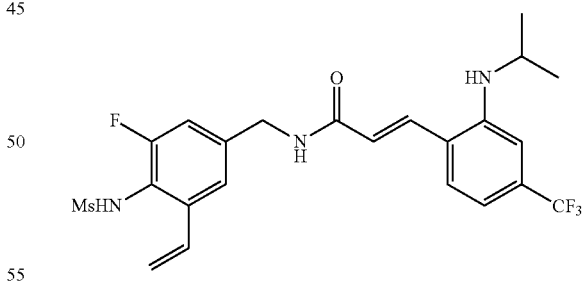

N-(4-Aminomethyl-2,5-difluoro-phenyl)-methanesulfonamide, HCl salt (43 mg, 0.154 mmol) was reacted with 3-(2-isopropylamino-4-trifluoro-phenyl)-acrylic acid (42 mg, 0.154 mmol) to give the title compound (34 mg, 42%) after purification by crystallization from Hex/EtOAc.

$^1$H NMR (300 MHz, DMSO-d6): δ 8.71 (s, 1H), 7.70 (d, 1H, J=15.3 Hz), 7.50 (m, 2H), 7.10 (m, 3H), 6.83 (s, 1H), 6.57 (d, 1H, J=15.3 Hz), 5.85 (m, 1H), 5.70 (m, 1H), 5.42 (m, 1H), 4.42 (d, 2H, J=5.4 Hz), 3.58 (m, 1H), 2.98 (s, 3H), 1.18 (d, 6H, J=6.0 Hz).

ESI [M−H]$^−$: 498

EXAMPLE 55

(R)—N-[1-(3,5-difluoro-4-methanesulfonylamino-phenyl)-ethyl]-3-(2-propylamino-4-trifluoromethyl-phenyl)-propionamide

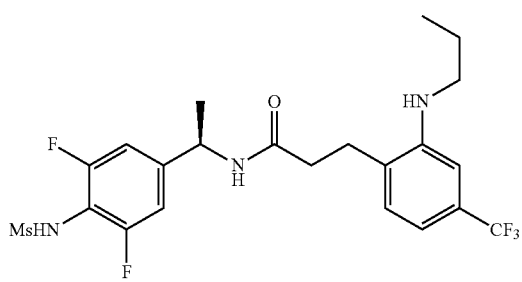

(R)—N-[1-(3,5-Difluoro-4-methanesulfonylamino-phenyl)-ethyl]-3-(2-propylamino-4-trifluoromethyl-phenyl)-acrylamide (12 mg) was reduced with Pd/C (15 mg) under hydrogen atmosphere to yield title compound (7 mg, 60%).

$^1$H NMR (300 MHz, CDCl$_3$): δ 7.02 (d, 1H, J=7.5 Hz), 6.95 (d, 1H, J=8.7 Hz), 6.87~6.71 (m, 3H), 6.17 (br, 1H), 5.62 (d, 1H, J=7.8 Hz), 4.96 (t, 1H, J=7.2 Hz), 3.15 (s, 3H), 3.00 (m, 2H), 2.83 (m, 2H), 2.47 (m, 2H), 1.32 (d, 3H, J=6.6 Hz), 0.96 (t, 3H, J=7.5 Hz).

EXAMPLE 56

N-(3,5-difluoro-4-methanesulfonylamino-benzyl)-3-(2-propylamino-4-trifluoromethyl-phenyl)-propionamide

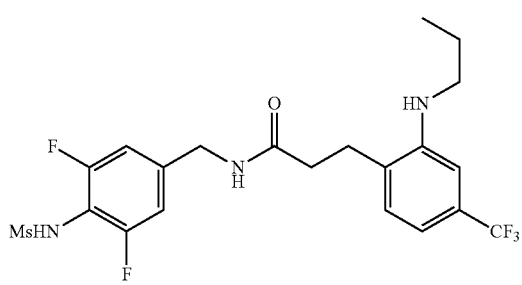

N-(3,5-Difluoro-4-methanesulfonylamino-benzyl)-3-(2-propylamino-4-trifluoromethyl-phenyl)-acrylamide (20 mg, 0.041 mmol) was reduced with Pd/C under hydrogen atmosphere to yield title compound (12 mg, 59%).

$^1$H NMR (300 MHz, CDCl$_3$): δ 7.08 (d, 1H, J=7.5 Hz), 6.95 (d, 1H, J=8.4 Hz), 36.87 (d, 1H, J=7.8 Hz), 6.78 (s, 1H), 6.76 (m, 1H), 6.29 (s, 1H), 5.93 (t, 1H), 4.36 (d, 2H, J=6.3 Hz), 3.19 (s, 3H), 3.09 (m, 2H), 2.91 (m, 2H), 2.55 (m, 2H), 1.70 (m, 2H), 1.02 (t, 3H, J=7.5 Hz)

EXPERIMENTAL EXAMPLE

Biological Potency Test

1. $^{45}$Ca influx Test

1) Separation of Spinal Dorsal Root Ganglia (DRG) in Newborn Rats and Primary Culture Thereof Neonatal (2-3 day old or younger than 2-3 day old) SD rats were put in ice for 5 minutes to anesthetize and disinfected with 70% ethanol. DRG of all part of spinal cord were dissected (Wood et al., 1988, J. Neurosci. 8, pp 3208-3220) and collected in DME/F12 medium to which 1.2 g/l sodium bicarbonate and 50 mg/l gentamycin were added. The DRG were incubated sequentially at 37° C. for 30 mins in 200 U/ml collagenase and 2.5 mg/ml trypsin, separately. The ganglia were washed twice with DME/F12 medium supplemented with 10% horse serum, triturated through a fire-polished Pasteur pipette, filtered through Nitex 80 membrane to obtain single cell suspension and the suspension was washed once more. This was subjected to centrifugation, then resuspended in cell culture medium at certain level of cell density. As the cell culture medium, DME/F12 medium supplemented with 10% horse serum was diluted with identical medium conditioned by C6 glioma cells 2 days on a confluent monolayer (1:1), and NGF (Nerve Growth Factor) was added to adjust 200 ng/ml as final concentration. After the cells were grown 2 days in medium where cytosine arabinoside (Ara-C, 100 μM) was added to kill dividing nonneuronal cells, medium was changed to one without Ara-C. The resuspended cells were plated at a density of 1500-2000 neurons/well onto Terasaki plates previously coated with 10 μg/ml poly-D-ornithine.

2) $^{45}$Ca Influx Experiments

DRG nerve cells from the primary culture of 2 days were equilibrated by washing 4 times with HEPES (10 mM, pH 7.4)-buffered Ca$^{2+}$, Mg$^{2+}$-free HBSS (H-HBSS). The solution in each well was removed from the individual well. Medium containing the test compound plus capsaicin (final concentration 0.5 μM) and $^{45}$Ca (final concentration 10 μCi/ml) in H-HBSS was added to each well and incubated at room temperature for 10 mins. Terasaki plates were washed five times with H-HBSS and dried at room temperature. To each well, 0.3% SDS (10 μl) was added to elute $^{45}$Ca. After the addition of scintillation cocktail of into each well, the amount of $^{45}$Ca influx into neuron was measured by counting radioactivity. Antagonistic activities of test compounds against vanilloid receptor were calculated as percent of the inhibition of maximal response of capsaicin at a concentration of 0.5 μM. The results are displayed in Table 1 below.

TABLE 1

| Results of Calcium Influx Test | |
|---|---|
| Examples | Antagonist Calcium Uptake Test (IC$_{50}$, μM) |
| 1 | 0.019 |
| 2 | 0.17 |
| 3 | 0.12 |
| 4 | 0.38 |
| 5 | 0.12 |
| 6 | 0.026 |
| 7 | 0.11 |
| 8 | 0.85 |
| 9 | 0.34 |
| 10 | 0.050 |
| 11 | 0.062 |
| 12 | 0.15 |
| 13 | 0.12 |
| 14 | 0.24 |
| 15 | 2.4 |
| 16 | 0.22 |
| 17 | 0.14 |
| 18 | 0.083 |
| 19 | 0.16 |
| 20 | 0.15 |
| 21 | 0.019 |

TABLE 1-continued

Results of Calcium Influx Test

| Examples | Antagonist Calcium Uptake Test ($IC_{50}$, μM) |
|---|---|
| 22 | 0.16 |
| 23 | 0.27 |
| 24 | 0.044 |
| 25 | 0.17 |
| 26 | 0.047 |
| 27 | 0.17 |
| 28 | 1.1 |
| 29 | 0.16 |
| 30 | 0.41 |
| 31 | 0.11 |
| 32 | 2.2 |
| 33 | 0.15 |
| 34 | 0.98 |
| 35 | 0.092 |
| 36 | 0.046 |
| 37 | 1.7 |
| 38 | 1.1 |
| 39 | 0.022 |
| 40 | 0.10 |
| 41 | 0.55 |
| 42 | 0.11 |
| 43 | 0.32 |
| 44 | 0.091 |
| 45 | 0.065 |
| 46 | 0.18 |
| 47 | 0.094 |
| 48 | 0.53 |
| 49 | 1.4 |
| 50 | 0.21 |
| 51 | 3.3 |
| 52 | 0.34 |
| 53 | 0.17 |
| 54 | 0.027 |
| 55 | 0.19 |
| 56 | 0.35 |

2. Analgesic Activity Test: Mouse Writhing Test by Inducing with phenyl-p-quinone Male ICR mice (mean body weight 25 g) were maintained in a controlled lighting environment (12 h on/12 h off) for experiment. Animals received an intraperitoneal injection of 0.3 ml of the chemical irritant phenyl-p-quinone (dissolved in saline containing 5% ethanol to be a dose of 4.5 mg/kg) and 6 mins later, the number of abdominal constrictions was counted in the subsequent 6 mins period. Animals (10 animals/group) received 0.2 ml of test compounds solution in vehicle of ethanol/Tween 80/saline (10/10/80) intraperitoneally 30 min before the injection of phenyl-p-quinone. In the case of oral administration, 0.2 ml of test compounds solution in vehicle of ethanol/Tween 80/saline (5/5/90) were administered 54 min prior to the 0.2 ml of 0.02% phenyl-p-quinone injection. A reduction in the number of writhes responding to the test drug compound relative to the number responding in saline control group was considered to be indicative of an analgesic effect. Analgesic effect was calculated by % inhibition equation (% inhibition=(C−T)/C×100), wherein C and T represent the number of writhes in control and compound-treated group, respectively. Most examples of the present disclosure having good in vitro activities, were tested at various doses (ranging from 0.3 to 3 mg/kg) and all compounds tested in vivo showed analgesic effects from 8 to 59% inhibition at each dose, respectively.

3. PK Study

Pharmacokinetics of compounds in rats were analyzed using the following experiment. Rats were fasted overnight prior to administration and until approximately 4 hours after administration. Rats were given a single oral administration of compound at same dose. Administration volume was 10 ml/kg. Blood samples were collected from the retro-orbital sinus at various times over the following 7 hrs. Immediately after each collection, plasmas were separated from blood cells by centrifugation and stored at −20° C. until the analysis was performed. The plasma samples were analyzed using a reverse phase high-performance chromatography (HPLC) method. The results are displayed in table 2 below.

TABLE 2

PK results for the compound having CF3-phenyl with meta substituent

| Ex # | Structure | IC50 | Cmax (mcg/ml) | Tmax (hour) | AUCpo (mcg hr ml-1) | T½ (hour) |
|---|---|---|---|---|---|---|
| 1 | (structure) | 0.019 | 0.466 | 3.500 | 1.939 | 1.399 |
| 2 | (structure) | 0.17 | 1.417 | 2.000 | 7.152 | 3.551 |

TABLE 2-continued

PK results for the compound having CF3-phenyl with meta substituent

| Ex # | Structure | IC50 | Cmax (mcg/ml) | Tmax (hour) | AUCpo (mcg hr ml-1) | T½ (hour) |
|---|---|---|---|---|---|---|
| 5 | 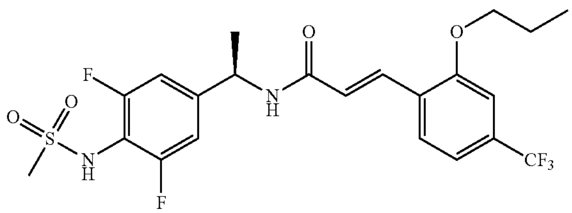 [SMILES: CCCOc1cc(C(F)(F)F)ccc1/C=C/C(=O)N[C@H](C)c1cc(F)c(NS(C)(=O)=O)c(F)c1] | 0.12 | 2.631 | 3.50 | 22.456 | 4.300 |
| 21 | 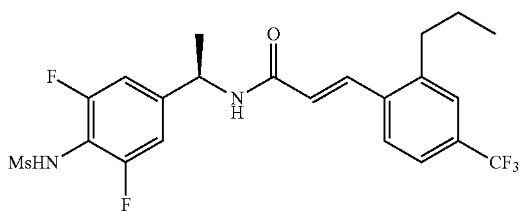 | 0.019 | 2.716 | 2.000 | 16.424 | 3.501 |
| 22 | 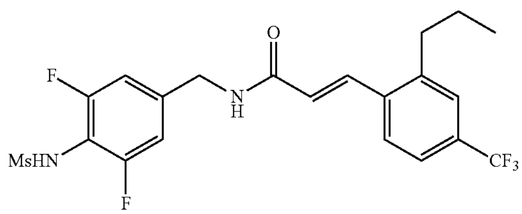 | 0.16 | 3.656 | 2.000 | 19.227 | 2.581 |
| 24 | 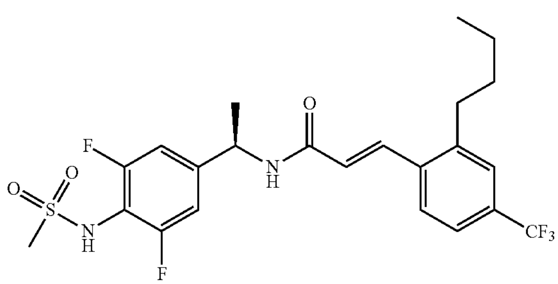 [SMILES: CCCCc1cc(C(F)(F)F)ccc1/C=C/C(=O)N[C@H](C)c1cc(F)c(NS(C)(=O)=O)c(F)c1] | 0.044 | 1.187 | 2.000 | 5.693 | 2.079 |
| 54 | 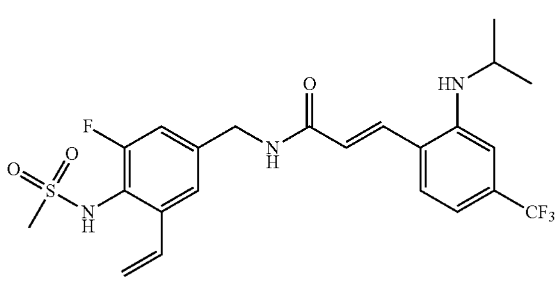 [SMILES: C=Cc1cc(CNC(=O)/C=C/c2ccc(C(F)(F)F)cc2NC(C)C)cc(F)c1NS(C)(=O)=O] | 0.027 | 0.772 | 2.000 | 5.316 | 4.050 |

4. Comparative Examples

As shown in Tables 2 and 3, the PK properties of the compounds of formula (I) of the present disclosure surprisingly have superior PK characteristics compared to compounds with a tert-butyl phenyl partial structure, with or without other substituents on the phenyl group, which were at least in part disclosed in the art, e.g. in WO 06/101318 or WO 06/101321 (also refer Table 3). Substantial increases in absorption and apparent half-life were observed by the replacement of tert-butyl phenyl by F-phenyl or CF₃-phenyl (see Table 2 vs 3).

TABLE 3

PK results for the compound having tert-butyl-phenyl

| Ex # | Structure | IC50 (μM) | Cmax (mcg/ml) | Tmax (hour) | AUCpo (mcg hr ml-1) | T½ (hour) |
|---|---|---|---|---|---|---|
| Comp Cpd A (Ex 15[a]) | 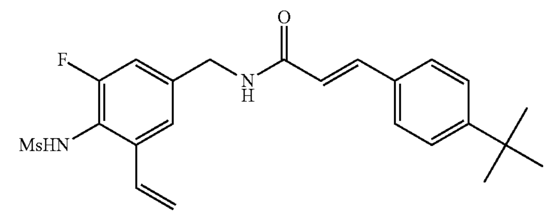 | 0.034 | <0.100 | —[b] | —[b] | —[b] |
| Comp Cpd B (Ex 4[c]) | 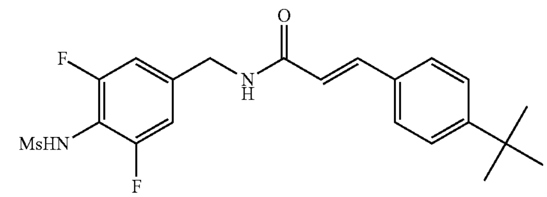 | 0.31 | 0.069 | 0.500 | 0.072 | 0.462 |
| Comp Cpd C (Ex 34[a]) | 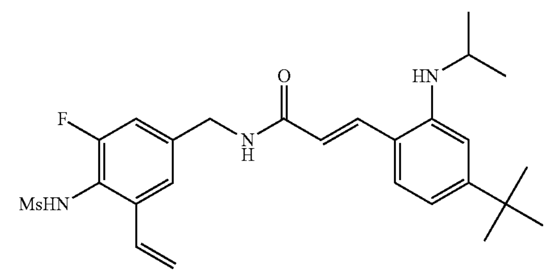 | 0.17 | <0.100 | —[b] | —[b] | —[b] |
| Comp Cpd D | 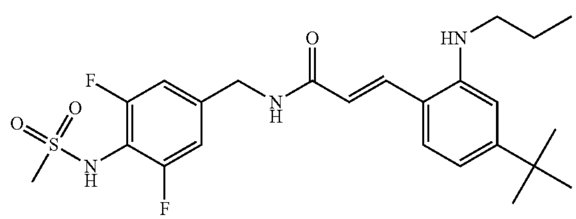 [SMILES: CCCNc1cc(C(C)(C)C)ccc1/C=C/C(=O)NCc1cc(F)c(NS(C)(=O)=O)c(F)c1] | 0.085 | <0.100 | —[b] | —[b] | —[b] |
| Comp Cpd E | 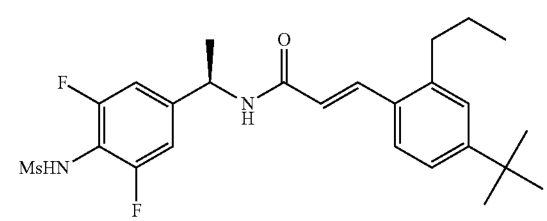 | 2.3 | <0.100 | —[b] | —[b] | —[b] |

[a]Example number in WO 06/101318
[b]could not be determined due to low plasma concentration (detection limit: 0.100 mcg/ml).
[c]Example number in WO 06/101321

As shown in Tables 2 and 4, the compounds of formula (I) of the present disclosure have superior $IC_{50}$ values and in some cases also improved PK characteristics compared to compounds with a $CF_3$-phenyl partial structure but without additional substituents on the phenyl group, which were at least in part disclosed in the art, e.g. in WO 06/101318 or WO 06/101321. Surprisingly, the introduction of an additional substituent in ortho position of the phenyl's attachment position to the cinnamoyl backbone confers improved VR1 activity to the compounds. For example, whilst comparative compound "G" has an IC50 value of more than 10 μM, the compounds 1, 3, 5-7, 10, 16-18, 21, 24, 26, 31, 39, 47, 50, and 52 of the present disclosure which all differ from "G" only by additional substituent(s) on phenyl group, all have IC50 values in a range between 0.019 and 0.34 μM. In addition, compound "G" shows only poor PK-properties, while all tested compounds of the present disclosure showed improved PK properties (in terms of T max and AUC). Likewise, while comparative compound "F" has a moderate $IC_{50}$ value of 0.57 μM, the $IC_{50}$ values of the corresponding examples of the present disclosure Ex 12 (0.15 μM) and 54 (0.027 μM) are significantly improved.

TABLE 4

PK results for the compound having CF3-phenyl

| Ex # | Structure | IC50 (μM) | Cmax (mcg/ml) | Tmax (hour) | AUCpo (mcg hr ml-1) | $T_{1/2}$ (hour) |
|---|---|---|---|---|---|---|
| Comp Cpd F (Ex 18[a]) | [structure: MsHN-phenyl(vinyl)-CH2-NH-C(O)-CH=CH-phenyl-CF3] | 0.57 | 5.001 | 2.000 | 40.123 | 4.589 |
| Comp Cpd G | [structure: MsHN-(3,5-difluorophenyl)-CH(CH3)-NH-C(O)-CH=CH-phenyl-CF3] | >10 | <0.100 | —[b] | —[b] | —[b] |

[a]Example number in WO 06/101318
[b]could not be determined due to low plasma concentration (detection limit: 0.100 mcg/ml).

In summary, the presently disclosed compounds of formula (I) show a significantly improved "balance" between VR1 activity and PK properties compared to the compounds disclosed in the art.

Industrial Applicability

As explained above, the compound according to the present disclosure is useful to prevent or to treat pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastroesophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, and pancreatitis.

More specifically, the compound according to the present disclosure is useful to preventing and treating of pain, which is or which is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, and other types of headaches.

What is claimed is:

1. The compound, an isomer, or a pharmaceutically acceptable salt thereof, wherein the compound is selected from the group consisting of;
    (R)—N-[1-(3,5-Difluoro-4-methanesulfonylamino-phenyl)-ethyl]-3-(2-propylamino-4-trifluoromethyl-phenyl)-acrylamide,
    N-(3,5-Difluoro-4-methanesulfonylamino-benzyl)-3-(2-propylamino-4-trifluoromethyl-phenyl)-acrylamide,
    (R)-3-(2-Butylamino-4-trifluoromethyl-phenyl)-N-[1-(3,5-difluoro-4-methanesulfonylamino-phenyl)-ethyl]-acrylamide,
    (R)—N-[1-(3,5-Difluoro-4-methanesulfonylamino-phenyl)-ethyl]-3-(2-propoxy-4-trifluoromethyl-phenyl)-acrylamide,
    (R)—N-[1-(3,5-Difluoro-4-methanesulfonylamino-phenyl)-ethyl]-3-(2,6-dipropyl-4-trifluoromethyl-phenyl)-acrylamide,
    (R)—N-[1-(3,5-Difluoro-4-methanesulfonylamino-phenyl)-ethyl]-3-(2-ethoxy-4-trifluoromethyl-phenyl)-acrylamide,
    (R)—N-[1-(3,5-Difluoro-4-methanesulfonylamino-phenyl)-ethyl]-3-(2-ethylamino-4-trifluoromethyl-phenyl)-acrylamide,
    N-(3-Fluoro-4-methanesulfonylamino-5-methyl-benzyl)-3-(2-propylamino-4-trifluoromethyl-phenyl)-acrylamide,
    N-(3-Fluoro-4-methanesulfonylamino-5-vinyl-benzyl)-3-(2-propylamino-4-trifluoromethyl-phenyl)-acrylamide,
    N-(3-Cyano-5-fluoro-4-methanesulfonylamino-benzyl)-3-(2-propylamino-4-trifluoromethyl-phenyl)-acrylamide,
    N-(3-Ethynyl-5-fluoro-4-methanesulfonylamino-benzyl)-3-(2-propoxy-4-trifluoromethyl-phenyl)-acrylamide,
    (R)-3-(2,6-Dibutyl-4-trifluoromethyl-phenyl)-N-[1-(3,5-difluoro-4-methanesulfonylamino-phenyl)-ethyl]-acrylamide,
    (R)-3-(2,6-Diethyl-4-trifluoromethyl-phenyl)-N-[1-(3,5-difluoro-4-methanesulfonylamino-phenyl)-ethyl]-acrylamide,
    N-(3,5-Difluoro-4-methanesulfonylamino-benzyl)-3-(2-ethylamino-4-trifluoromethyl -phenyl)-acrylamide,
    3-(2-Ethylamino-4-trifluoromethyl-phenyl)-N-(3-fluoro-4-methanesulfonylamino-5-methyl-benzyl)-acrylamide,
    N-(3,5-Difluoro-4-methanesulfonylamino-benzyl)-3-(2-isopropoxy-4-trifluoromethyl -phenyl)-acrylamide,
    (R)—N-[1-(3,5-Difluoro-4-methanesulfonylamino-phenyl)-ethyl]-3-(2-propyl-4-trifluoromethyl-phenyl)-acrylamide,
    N-(3,5-Difluoro-4-methanesulfonylamino-benzyl)-3-(2-propyl-4-trifluoromethyl -phenyl)-acrylamide, N-(3-Fluoro-4-methanesulfonylamino-5-methyl-benzyl)-3-(2-propyl-4-trifluoromethyl -phenyl)-acrylamide, (R)-3-(2-Butyl-4-trifluoromethyl-phenyl)-N-[1-(3,5-difluoro-4-methanesulfonylamino -phenyl)-ethyl]-acrylamide, (R)—N-[1-(3,5-Difluoro-4-methanesulfonylamino-phenyl)-propyl]-3-(2-propyl-4-trifluoromethyl-phenyl)-acrylamide, (R)—N-[1-(3,5-Difluoro-4-methanesulfonylamino-phenyl)-ethyl]-3-(2-isopropoxy-4-trifluoromethyl-phenyl)-acrylamide, (R)-3-(2-Butoxy-4-trifluoromethyl-phenyl)-N-[1-(3,5-difluoro-4-methanesulfonylamino-phenyl)-ethyl]-acrylamide, N-(3-Ethynyl-5-fluoro-4-methanesulfonylamino-benzyl)-3-(2-propyl-4-trifluoromethyl -phenyl)-acrylamide, (R)-3-(2-Butyl-4-trifluoromethyl-phenyl)-N-[1-(3-fluoro-4-methanesulfonylamino -phenyl)-ethyl]-acrylamide, (R)-3-(2-sec-Butoxy-4-trifluoromethyl-phenyl)-N-[1-(3,5-difluoro-4-methanesulfonylamino-phenyl)-ethyl]-acrylamide, N-(3,5-Difluoro-4-methanesulfonylamino-benzyl)-3-(2-ethylamino-4-fluoro-phenyl) -acrylamide, (R)—N-(2-Fluoro-4-{1-[3-(2-propyl-4-trifluoromethyl-phenyl)-allylamino]-ethyl}-phenyl)-methanesulfonamide, (R)—N-[1-(3,5-Difluoro-4-methanesulfonylamino-phenyl)-ethyl]-3-(2-isobutyl-4-trifluoromethyl-phenyl)-acrylamide, (R)-3-(2-Cyclohexylmethoxy-4-trifluoromethyl-phenyl)-N-[1-(3,5-difluoro-4methanesulfonylamino-phenyl)-ethyl]-acrylamide, N-(3-Fluoro-4-methanesulfonylamino-5-vinyl-benzyl)-3-(2-isopropylamino-4-trifluoromethyl-phenyl)-acrylamide, and (R)—N-[1-(3,5-Difluoro-4-methanesulfonylamino-phenyl)-ethyl]-3-(2-propylamino-4-trifluoromethyl-phenyl)-propionamide.

2. The compound according to claim 1, an isomer, or a pharmaceutically acceptable salt thereof, wherein the compound is selected from the group consisting of;

(R)—N-[1-(3,5-Difluoro-4-methanesulfonylamino-phenyl)-ethyl]-3-(2-propylamino-4-trifluoromethyl-phenyl)-acrylamide, (R)-3-(2-Butylamino-4-trifluoromethyl-phenyl)-N-[1-(3,5-difluoro-4-methanesulfonylamino-phenyl)-ethyl]-acrylamide, (R)—N-[1-(3,5-Difluoro-4-methanesulfonylamino-phenyl)-ethyl]-3-(2-propoxy-4-trifluoromethyl-phenyl)-acrylamide, (R)—N-[1-(3,5-Difluoro-4-methanesulfonylamino-phenyl)-ethyl]-3-(2,6-dipropyl-4-trifluoromethyl-phenyl)-acrylamide, (R)—N -[1-(3,5-Difluoro-4-methanesulfonylamino-phenyl)-ethyl]-3-(2-ethoxy-4-trifluoromethyl-phenyl)-acrylamide, (R)—N-[1-(3,5-Difluoro-4-methanesulfonylamino-phenyl)-ethyl]-3-(2-ethylamino-4-trifluoromethyl-phenyl)-acrylamide, N-(3-Fluoro-4-methanesulfonylamino-5-methyl-benzyl)-3-(2-propylamino-4-trifluoromethyl-phenyl)-acrylamide, N-(3-Fluoro-4-methanesulfonylamino-5-vinyl-benzyl)-3-(2-propylamino-4-trifluoromethyl-phenyl)-acrylamide, N-(3-Cyano-5-fluoro-4-methanesulfonylamino-benzyl)-3-(2-propylamino-4-trifluoromethyl-phenyl)-acrylamide, (R)-3-(2,6-Diethyl-4-trifluoromethyl-phenyl)-N-[1-(3,5-difluoro-4-methanesulfonylamino-phenyl)-ethyl]-acrylamide, N-(3,5-Difluoro-4-methanesulfonylamino-benzyl)-3-(2-ethylamino-4-trifluoromethyl -phenyl)-acrylamide, N-(3,5-Difluoro-4-methanesulfonylamino-benzyl)-3-(2-isopropoxy-4-trifluoromethyl -phenyl)-acrylamide, (R)—N-[1-(3,5-Difluoro-4-methanesulfonylamino-phenyl)-ethyl]-3-(2-propyl-4-trifluoromethyl-phenyl)-acrylamide, (R)-3-(2-Butyl-4-trifluoromethyl-phenyl)-N-[1-(3,5-difluoro-4-methanesulfonylamino -phenyl)-ethyl]-acrylamide, (R)—N-[1-(3,5-Difluoro-4-methanesulfonylamino-phenyl)-ethyl]-3-(2-isopropoxy-4-trifluoromethyl-phenyl)-acrylamide, (R)-3-(2-Butoxy-4-trifluoromethyl-phenyl)-N-[1-(3,5-difluoro-4-methanesulfonylamino -phenyl)-ethyl]-acrylamide, N-(3-Ethynyl-5-fluoro-4-methanesulfonylamino-benzyl)-3-(2-propyl-4-trifluoromethyl -phenyl)-acrylamide, (R)-3-(2-Butyl-4-trifluoromethyl-phenyl)-N[1-(3-fluoro-4-methanesulfonylamino -phenyl)-ethyl]-acrylamide, (R)-3-(2-sec-Butoxy-4-trifluoromethyl-phenyl)-N[1-(3,5-difluoro-4-methanesulfonylamino-phenyl)-ethyl]-acrylamide, (R)—N-[1-(3,5-Difluoro-4-methanesulfonylamino-phenyl)-ethyl]-3-(2-ethylamino-4-fluoro-phenyl)-acrylamide, (R)-N-(2-Fluoro-4- {1-[3-(2-propyl-4-trifluoromethyl-phenyl)-allylamino]-ethyl}-phenyl)-methanesulfonamide, (R)—N-[1-(3,5-Difluoro-4-methanesulfonylamino-phenyl)-ethyl]-3-(2-isobutyl-4-trifluoromethyl-phenyl)-acrylamide, and N-(3-Fluoro-4-methanesulfonylamino-5-vinyl-benzyl)-3-(2-isopropylamino-4-trifluoromethyl-phenyl)-acrylamide.

3. A compound according to claim 1 for use as a medicament.

4. A pharmaceutical composition comprising the compound according to claim 1, an isomer, or a pharmaceutically acceptable salt thereof, as an active ingredient and a pharmaceutically acceptable carrier.

* * * * *